(12) United States Patent
Ståhl et al.

(10) Patent No.: US 12,215,379 B2
(45) Date of Patent: Feb. 4, 2025

(54) IN SITU ANALYSIS OF CHROMATIN INTERACTION

(71) Applicant: 10x Genomics, Inc., Pleasanton, CA (US)

(72) Inventors: Patrik Ståhl, Stockholm (SE); Pelin Sahlén, Uppsala (SE)

(73) Assignee: 10X GENOMICS, INC., Pleasanton, CA (US)

( * ) Notice: Subject to any disclaimer, the term of this patent is extended or adjusted under 35 U.S.C. 154(b) by 699 days.

(21) Appl. No.: 17/177,501

(22) Filed: Feb. 17, 2021

(65) Prior Publication Data

US 2021/0254140 A1    Aug. 19, 2021

Related U.S. Application Data

(60) Provisional application No. 62/977,512, filed on Feb. 17, 2020.

(51) Int. Cl.
   *C12Q 1/6818*      (2018.01)
   *C12Q 1/6837*      (2018.01)

(52) U.S. Cl.
   CPC .......... *C12Q 1/6818* (2013.01); *C12Q 1/6837* (2013.01)

(58) Field of Classification Search
   CPC ............................ C12Q 1/6818; C12Q 1/6837
   See application file for complete search history.

(56) References Cited

U.S. PATENT DOCUMENTS

| | | |
|---|---|---|
| 4,683,195 A | 7/1987 | Mullis et al. |
| 4,683,202 A | 7/1987 | Mullis |
| 4,800,159 A | 1/1989 | Mullis et al. |
| 4,965,188 A | 10/1990 | Mullis et al. |
| 5,512,462 A | 4/1996 | Cheng |
| 5,599,675 A | 2/1997 | Brenner |
| 5,635,352 A | 6/1997 | Urdea et al. |
| 5,695,940 A | 12/1997 | Drmanac et al. |
| 5,750,341 A | 5/1998 | Macevicz |
| 6,054,274 A | 4/2000 | Sampson et al. |
| 6,172,218 B1 | 1/2001 | Brenner |
| 6,291,187 B1 | 9/2001 | Kingsmore et al. |
| 6,306,597 B1 | 10/2001 | Macevicz |
| 6,323,009 B1 | 11/2001 | Lasken et al. |
| 6,344,329 B1 | 2/2002 | Lizardi et al. |
| 6,368,801 B1 | 4/2002 | Faruqi |
| 6,391,937 B1 | 5/2002 | Beuhler et al. |
| 6,534,266 B1 | 3/2003 | Singer |
| 6,969,488 B2 | 11/2005 | Bridgham et al. |
| 7,057,026 B2 | 6/2006 | Barnes et al. |
| 7,255,994 B2 | 8/2007 | Lao |
| 7,264,929 B2 | 9/2007 | Rothberg et al. |
| 7,473,767 B2 | 1/2009 | Dimitrov |
| 7,534,991 B2 | 5/2009 | Miller et al. |
| 7,555,155 B2 | 6/2009 | Levenson et al. |
| 7,655,898 B2 | 2/2010 | Miller |
| 7,910,304 B2 | 3/2011 | Drmanac |
| 7,941,279 B2 | 5/2011 | Hwang et al. |
| 7,989,166 B2 | 8/2011 | Koch et al. |
| 8,124,751 B2 | 2/2012 | Pierce et al. |
| 8,199,999 B2 | 6/2012 | Hoyt et al. |
| 8,268,554 B2 | 9/2012 | Schallmeiner |
| 8,330,087 B2 | 12/2012 | Domenicali |
| 8,415,102 B2 | 4/2013 | Geiss et al. |
| 8,431,691 B2 | 4/2013 | McKernan et al. |
| 8,460,865 B2 | 6/2013 | Chee et al. |
| 8,462,981 B2 | 6/2013 | Determan et al. |
| 8,481,258 B2 | 7/2013 | Church et al. |
| 8,519,115 B2 | 8/2013 | Webster et al. |
| 8,551,710 B2 | 10/2013 | Bernitz et al. |
| 8,658,361 B2 | 2/2014 | Wu et al. |
| 8,771,950 B2 | 7/2014 | Church et al. |
| 8,986,926 B2 | 3/2015 | Ferree et al. |
| 9,201,063 B2 | 12/2015 | Sood et al. |
| 9,273,349 B2 | 3/2016 | Nguyen et al. |
| 9,371,563 B2 | 6/2016 | Geiss et al. |
| 9,371,598 B2 | 6/2016 | Chee |
| 9,376,717 B2 | 6/2016 | Gao et al. |
| 9,512,422 B2 | 12/2016 | Barnard et al. |
| 9,541,504 B2 | 1/2017 | Hoyt |
| 9,551,032 B2 | 1/2017 | Landegren et al. |
| 9,624,538 B2 | 4/2017 | Church et al. |
| 9,714,446 B2 | 7/2017 | Webster et al. |
| 9,714,937 B2 | 7/2017 | Dunaway |
| 9,727,810 B2 | 8/2017 | Fodor et al. |
| 9,778,155 B2 | 10/2017 | Gradinaru et al. |
| 9,783,841 B2 | 10/2017 | Nolan et al. |
| 9,889,422 B2 | 2/2018 | Smith et al. |
| 9,909,167 B2 | 3/2018 | Samusik et al. |

(Continued)

FOREIGN PATENT DOCUMENTS

| | | |
|---|---|---|
| WO | WO 2005/065814 | 7/2005 |
| WO | WO 2006/064199 | 6/2006 |

(Continued)

OTHER PUBLICATIONS

Gao, H., et al., "Rolling circle amplification for single cell analysis and in situ sequencing," Trends in Analytical Chemistry 121: 115700. doi: 10.1016/j.trac.2019.115700. (Year: 2019).*

(Continued)

*Primary Examiner* — Tracy Vivlemore
*Assistant Examiner* — Eric J Rogers
(74) *Attorney, Agent, or Firm* — MORRISON & FOERSTER LLP

(57) ABSTRACT

In some embodiments described herein are methods performed in situ for analyzing chromatin interaction events in a cell or in cells of a sample such as a non-homogenized tissue sample. The methods can comprise the spatial analysis of chromatin interaction events across cell populations in a biological sample. The methods can further comprise obtaining a biological sample, hybridizing probes to target nucleic acid sequences involved in chromatin interaction events and producing a nucleic acid sequence comprising all or part of the target nucleic acid sequences, amplifying the nucleic acid sequence so produced and detecting the amplified nucleic acid sequence in situ.

20 Claims, 13 Drawing Sheets
Specification includes a Sequence Listing.

(56) References Cited

U.S. PATENT DOCUMENTS

| | | |
|---|---|---|
| 10,032,064 B2 | 7/2018 | Hoyt |
| 10,059,990 B2 | 8/2018 | Boyden et al. |
| 10,126,242 B2 | 11/2018 | Miller et al. |
| 10,179,932 B2 | 1/2019 | Church et al. |
| 10,227,639 B2 | 3/2019 | Levner et al. |
| 10,246,700 B2 | 4/2019 | Dunaway et al. |
| 10,266,888 B2 | 4/2019 | Daugharthy et al. |
| 10,267,808 B2 | 4/2019 | Cai |
| 10,309,879 B2 | 6/2019 | Chen et al. |
| 10,317,321 B2 | 6/2019 | Tillberg et al. |
| 10,364,457 B2 | 7/2019 | Wassie et al. |
| 10,370,698 B2 | 8/2019 | Nolan et al. |
| 10,415,080 B2 | 9/2019 | Dunaway et al. |
| 10,457,980 B2 | 10/2019 | Cai et al. |
| 10,465,235 B2 | 11/2019 | Gullberg et al. |
| 10,494,662 B2 | 12/2019 | Church et al. |
| 10,495,554 B2 | 12/2019 | Deisseroth et al. |
| 10,501,777 B2 | 12/2019 | Beechem et al. |
| 10,501,791 B2 | 12/2019 | Church et al. |
| 10,510,435 B2 | 12/2019 | Cai et al. |
| 10,526,639 B2 | 1/2020 | Pombo et al. |
| 10,526,649 B2 | 1/2020 | Chen et al. |
| 10,545,075 B2 | 1/2020 | Deisseroth et al. |
| 10,580,128 B2 | 3/2020 | Miller |
| 10,640,816 B2 | 5/2020 | Beechem et al. |
| 10,640,826 B2 | 5/2020 | Church et al. |
| 10,669,569 B2 | 6/2020 | Gullberg et al. |
| 10,746,981 B2 | 8/2020 | Tomer et al. |
| 10,774,372 B2 | 9/2020 | Chee et al. |
| 10,774,374 B2 | 9/2020 | Frisén et al. |
| 10,794,802 B2 | 10/2020 | Gradinaru et al. |
| 10,802,262 B2 | 10/2020 | Tomer et al. |
| 10,815,519 B2 | 10/2020 | Husain et al. |
| 10,829,814 B2 | 11/2020 | Fan et al. |
| 10,844,426 B2 | 11/2020 | Daugharthy et al. |
| 10,858,698 B2 | 12/2020 | Church et al. |
| 10,872,679 B2 | 12/2020 | Cai et al. |
| 10,964,001 B2 | 3/2021 | Miller |
| 11,459,603 B2 | 10/2022 | Tyagi et al. |
| 2002/0051986 A1 | 5/2002 | Baez et al. |
| 2003/0013091 A1 | 1/2003 | Dimitrov |
| 2005/0100900 A1 | 5/2005 | Kawashima et al. |
| 2006/0188901 A1 | 8/2006 | Barnes et al. |
| 2006/0240439 A1 | 10/2006 | Smith et al. |
| 2006/0281109 A1 | 12/2006 | Barr et al. |
| 2007/0166705 A1 | 7/2007 | Milton et al. |
| 2007/0166708 A1 | 7/2007 | Dimitrov et al. |
| 2010/0015607 A1 | 1/2010 | Geiss et al. |
| 2010/0047924 A1 | 2/2010 | Webster et al. |
| 2010/0055733 A1 | 3/2010 | Lutolf et al. |
| 2010/0112710 A1 | 5/2010 | Geiss et al. |
| 2010/0261026 A1 | 10/2010 | Ferree et al. |
| 2010/0262374 A1 | 10/2010 | Hwang et al. |
| 2011/0223585 A1 | 9/2011 | Gullberg et al. |
| 2012/0270305 A1 | 10/2012 | Reed et al. |
| 2013/0079232 A1 | 3/2013 | Kain et al. |
| 2013/0260372 A1 | 10/2013 | Buermann et al. |
| 2013/0288249 A1 | 10/2013 | Gullbert |
| 2013/0323729 A1 | 12/2013 | Landegren et al. |
| 2014/0194311 A1 | 6/2014 | Gullberg et al. |
| 2014/0371088 A1 | 12/2014 | Webster |
| 2016/0024555 A1 | 1/2016 | Church et al. |
| 2016/0108458 A1 | 4/2016 | Frei et al. |
| 2016/0208323 A1 | 7/2016 | Bernstein et al. |
| 2016/0305856 A1 | 10/2016 | Boyden et al. |
| 2016/0312213 A1 * | 10/2016 | Rokhsar ............... C12Q 1/6883 |
| 2016/0369329 A1 | 12/2016 | Cai et al. |
| 2016/0376642 A1 | 12/2016 | Landegren et al. |
| 2017/0009278 A1 | 1/2017 | Söderberg et al. |
| 2017/0081489 A1 | 3/2017 | Rodriques et al. |
| 2017/0101672 A1 | 4/2017 | Luo et al. |
| 2017/0219465 A1 | 8/2017 | Desseroth et al. |
| 2017/0220733 A1 | 8/2017 | Zhuang et al. |
| 2017/0253918 A1 | 9/2017 | Kohman |
| 2018/0010175 A1 | 1/2018 | Cheng |
| 2018/0052081 A1 | 2/2018 | Kohman |
| 2018/0080876 A1 | 3/2018 | Rockel et al. |
| 2018/0208967 A1 | 7/2018 | Larman et al. |
| 2018/0237864 A1 | 8/2018 | Imler et al. |
| 2018/0251833 A1 | 9/2018 | Daugharthy et al. |
| 2018/0320226 A1 | 11/2018 | Church et al. |
| 2019/0017106 A1 | 1/2019 | Frisen et al. |
| 2019/0032128 A1 | 1/2019 | Chen et al. |
| 2019/0055594 A1 | 2/2019 | Samusik et al. |
| 2019/0112599 A1 | 4/2019 | Church et al. |
| 2019/0119735 A1 | 4/2019 | Deisseroth et al. |
| 2019/0155835 A1 | 5/2019 | Daugharthy et al. |
| 2019/0161796 A1 | 5/2019 | Hauling et al. |
| 2019/0177718 A1 | 6/2019 | Church et al. |
| 2019/0194709 A1 | 6/2019 | Church et al. |
| 2019/0218608 A1 | 7/2019 | Daugharthy et al. |
| 2019/0249248 A1 | 8/2019 | Beechem et al. |
| 2019/0264270 A1 | 8/2019 | Zhuang et al. |
| 2019/0271028 A1 | 9/2019 | Khafizov et al. |
| 2019/0276881 A1 | 9/2019 | Zhuang et al. |
| 2019/0339203 A1 | 11/2019 | Miller et al. |
| 2020/0010891 A1 | 1/2020 | Beechem et al. |
| 2020/0071751 A1 | 3/2020 | Daugharthy et al. |
| 2020/0123597 A1 | 4/2020 | Daniel |
| 2020/0140920 A1 | 5/2020 | Pierce et al. |
| 2020/0224243 A1 | 7/2020 | Desai et al. |
| 2020/0224244 A1 | 7/2020 | Nilsson et al. |
| 2020/0239946 A1 | 7/2020 | Dewal |
| 2020/0354774 A1 | 11/2020 | Church et al. |
| 2020/0354782 A1 | 11/2020 | Dewal |
| 2020/0362398 A1 | 11/2020 | Kishi et al. |
| 2020/0393343 A1 | 12/2020 | Kennedy-Darling et al. |
| 2021/0017587 A1 | 1/2021 | Cai et al. |
| 2021/0115504 A1 | 4/2021 | Cai et al. |
| 2021/0238662 A1 | 8/2021 | Bava |
| 2021/0238674 A1 | 8/2021 | Bava |
| 2021/0254140 A1 | 8/2021 | Stahl et al. |
| 2021/0262018 A1 | 8/2021 | Bava et al. |
| 2021/0277460 A1 | 9/2021 | Bava |
| 2021/0340621 A1 | 11/2021 | Daugharthy et al. |
| 2021/0388423 A1 | 12/2021 | Bava et al. |
| 2021/0388424 A1 | 12/2021 | Bava |
| 2022/0049302 A1 | 2/2022 | Daugharthy et al. |
| 2022/0049303 A1 | 2/2022 | Busby et al. |
| 2022/0083832 A1 | 3/2022 | Shah |
| 2022/0084628 A1 | 3/2022 | Shah |
| 2022/0084629 A1 | 3/2022 | Shah |
| 2022/0136049 A1 | 5/2022 | Bava et al. |
| 2022/0186300 A1 | 6/2022 | Bava |
| 2022/0195498 A1 | 6/2022 | Kuhnemund et al. |
| 2022/0213529 A1 | 7/2022 | Kuhnemund et al. |
| 2022/0228200 A1 | 7/2022 | Bava |

FOREIGN PATENT DOCUMENTS

| | | | |
|---|---|---|---|
| WO | WO 2007/010251 | 1/2007 | |
| WO | WO 2012/152942 | 11/2012 | |
| WO | WO 2012/159025 | 11/2012 | |
| WO | WO 2012/160083 | 11/2012 | |
| WO | WO 2014/163886 | 10/2014 | |
| WO | WO 2017/079406 | 5/2017 | |
| WO | WO 2017/143155 | 8/2017 | |
| WO | WO 2018/026873 | 2/2018 | |
| WO | WO 2018/160397 | 9/2018 | |
| WO | WO-2018175779 A1 * | 9/2018 | ............ C12N 15/11 |
| WO | WO-2019165318 A9 * | 9/2019 | ......... C12N 15/1065 |
| WO | WO 2019/199579 | 10/2019 | |
| WO | WO 2020/076976 | 4/2020 | |
| WO | WO 2020/076979 | 4/2020 | |
| WO | WO 2020/096687 | 5/2020 | |
| WO | WO 2020/099640 | 5/2020 | |
| WO | WO 2020/117914 | 6/2020 | |
| WO | WO 2020/123316 | 6/2020 | |
| WO | WO 2020/123742 | 6/2020 | |
| WO | WO 2020/142490 | 7/2020 | |
| WO | WO 2020/240025 | 12/2020 | |
| WO | WO 2020/254519 | 12/2020 | |
| WO | WO 2021/123282 | 6/2021 | |

(56) References Cited

FOREIGN PATENT DOCUMENTS

| WO | WO 2021/123286 | 6/2021 |
|---|---|---|
| WO | WO 2021/155063 | 8/2021 |
| WO | WO 2021/168326 | 8/2021 |

OTHER PUBLICATIONS

Chen, X., et al., "Chromatin in situ proximity (ChrISP): single-cell analysis of chromatin proximities at a high resolution," Biotechniques 56(3):117-124. doi: 10.2144/000114145. (Year: 2014).*

Fontenete, S., et al., "Prediction of melting temperatures in fluorescence in situ hybridization (FISH) procedures using thermodynamic models," Critical Reviews in Biotechnology 36(3): 566-577. doi: 10.3109/07388551.2014.993589. Epub Jan. 14, 2015. (Year: 2015).*

Wei, X., et al., "pBACode: a random-barcode-based high-throughput approach for BAC paired-end sequencing and physical clone mapping," Nucleic Acids Research 45(7): e52. doi: 10.1093/nar/gkw1261. Published online Dec. 15, 2016 (Year: 2016).*

Kempfer, R., and Pombo, A., "Methods for mapping 3D chromosome architecture," Nat Rev Genet 21(4): 207-226. doi: 10.1038/s41576-019-0195-2. Epub Dec. 17, 2019. (Year: 2019).*

Ali et al. "Rolling circle amplification: a versatile tool for chemical biology, materials science and medicine." *Chemical Society Reviews* 43.10 (2014): 3324-3341.

Babaei et al. "Hi-C chromatin interaction networks predict co-expression in the mouse cortex." *PLoS computational biology* 11.5 (2015): e1004221.

Baner et al., "Signal amplification of padlock probes by rolling circle replication," Nucleic Acids Res. (1998) 26(22):5073-5078.

Belton et al. "HI-C: a comprehensive technique to capture the conformation of genomes." *Methods* 58.3 (2012): 268-276.

Bibikova et al., "Quantitative gene expression profiling in formalin-fixed, paraffin-embedded tissues using universal bead arrays," Am J Pathol. Nov. 2004;165(5):1799-807.

Bienko et al. "A versatile genome-scale PCR-based pipeline for high-definition DNA FISH." *nature methods* 10.2 (2013): 122-124.

Bolognesi et al., "Multiplex Staining by Sequential Immunostaining and Antibody Removal on Routine Tissue Sections," J. Histochem. Cytochem. (2017); 65(8): 431-444.

Brenner et al. "Gene expression analysis by massively parallel signature sequencing (MPSS) on microbead arrays." Nature biotechnology 18.6 (2000): 630-634. Abstract Only.

Broude et al. "PNA openers as a tool for direct quantification of specific targets in duplex DNA." Journal of Biomolecular Structure and Dynamics 17.2 (1999): 237-244.

Buenrostro et al., "Transposition of native chromatin for multimodal regulatory analysis and personal epigenomics," Nat Methods. (2013) 10(12): 1213-1218.

Capodieci et al., "Gene expression profiling in single cells within tissue," Nat Methods. (2005) 2(9): 663-5.

Chen et al., "Nanoscale imaging of RNA with expansion microscopy," Nat Methods. (2016) 13:679-684.

Chen et al., "Expansion Microscopy," Science (2015) 347(6221):543-548.

Chen et al., "RNA imaging. Spatially resolved, highly multiplexed RNA profiling in single cells," Science. (2015) 348(6233): aaa6090. 16 pgs.

Conze et al., "Single molecule analysis of combinatorial splicing," Nucleic Acids Res. (2010) 38(16): e163.

Dean et al., "Rapid Amplification of Plasmid and Phage DNA Using Phi29 DNA Polymerase and Multiply-Primed Rolling Circle Amplification," Genome Research (2001) 11:1095-1099.

De Bie et al. "Characterization of COMMD protein-protein interactions in NF-κB signalling." *Biochemical Journal* 398.1 (2006): 63-71.

Dekker et al. "Capturing chromosome conformation." *science* 295. 5558 (2002): 1306-1311.

Doty et al. "Strand separation and specific recombination in deoxyribonucleic acids: physical chemical studies." *Proceedings of the National Academy of Sciences of the United States of America* 46.4 (1960): 461.

Eng et al., "Transcriptome-scale super-resolved imaging in tissues by RNA seqFISH," Nature. (2019) 568(7751): 235-239.

Faruqi et al., "High-throughput genotyping of single nucleotide polymorphisms with rolling circle amplification," BMC Genomics. (2001) 2:4.

Femino et al., "Visualization of single RNA transcripts in situ," Science. (1998) 280(5363): 585-90.

Forcucci et al., "All-plastic miniature fluorescence microscope for point-of-care readout of bead-based bioassays," J Biomed Opt. (2015) 20(10): 105010.

Gavrilovic et al., "Automated classification of multicolored rolling circle products in dual-channel wide-field fluorescence microscopy," Cytometry A. (2011) 79(7): 518-27.

Geiss et al., "Direct multiplexed measurement of gene expression with color-coded probe pairs," Nat Biotechnol. (2008) 26(3): 317-25.

Ghavi-Helm et al. "Enhancer loops appear stable during development and are associated with paused polymerase." Nature 512.7512 (2014): 96-100.

Glass et al., "SIMPLE: a sequential immunoperoxidase labeling and erasing method," J Histochem Cytochem. (2009) 57(10); 899-905.

Goh, J.J.L. et al. (Jul. 2020, e-pub. Jun. 15, 2020). "Highly Specific Multiplexed RNA Imaging In Tissues With Split-FISH," Nat Methods 17(7):689-693. doi: 10.1038/s41592-020-0858-0. Epub Jun. 15, 2020.

Goransson et al., "A single molecule array for digital targeted molecular analyses," Nucleic Acids Res. 2009 37(1):e7. doi: 10.1093/nar/gkn921.

Grob et al. "Characterization of chromosomal architecture in *Arabidopsis* by chromosome conformation capture." *Genome biology* 14.11 (2013): 1-19.

Gunderson et al. "Decoding randomly ordered DNA arrays." Genome research 14.5 (2004): 870-877.

Gyllborg et al., "Hybridization-based in situ sequencing (HybISS) for spatially resolved transcriptomics in human and mouse brain tissue," Nucleic Acids Res. (2020) 48(19): e112.

Hagene et al. "Quantitative analysis of chromosome conformation capture assays (3C-qPCR)." *Nature protocols* 2.7 (2007): 1722-1733.

Hakhverdyan et al. "Rapid, optimized interactomic screening." *Nature methods* 12.6 (2015): 553-560.

Han et al., "Quantum-dot-tagged microbeads for multiplexed optical coding of biomolecules," Nat Biotechnol. (2001) 19(7): 631-5.

Hwang et al. "Glycoproteomics in neurodegenerative diseases." *Mass spectrometry reviews* 29.1 (2010): 79-125.

Itkovitz et al., "Validating Transcripts with Probes and Imaging Technology," Nat Methods. (2011) 8(4 Suppl): S12-S19.

Itkovitz et al., "Single-molecule transcript counting of stem-cell markers in the mouse intestine," Nat Cell Biol. (2011) 14(1): 106-14.

Jamur et al., "Permeabilization of cell membranes," Method Mol. Biol. (2010) 588: 63-66 (abstract only).

Jiang et al. "Brain iron metabolism dysfunction in Parkinson's disease." Molecular neurobiology 54.4 (2017): 3078.

Ke et al., "In situ sequencing for RNA analysis in preserved tissue and cells," Nat Methods. (2013) 10(9):857-60.

Klaesson et al. "Improved efficiency of in situ protein analysis by proximity ligation using UnFold probes." *Scientific reports* 8.1 (2018): 1-13.

Korlach et al. "Selective aluminum passivation for targeted immobilization of single DNA polymerase molecules in zero-mode waveguide nanostructures." *Proceedings of the National Academy of Sciences* 105.4 (2008): 1176-1181.

Kuhn et al. "Rolling-circle amplification under topological constraints." *Nucleic acids research* 30.2 (2002): 574-580.

Kulaeva et al. "Distant activation of transcription: mechanisms of enhancer action." *Molecular and cellular biology* 32.24 (2012): 4892-4897.

(56) References Cited

OTHER PUBLICATIONS

Lagunavicius et al., "Novel application of Phi29 DNA polymerase: RNA detection and analysis in vitro and in situ by target RNA-primed RCA," RNA. (2009) 15(5):765-71.
Larsson et al. "In situ detection and genotyping of individual mRNA molecules," Nat Methods. (2010) 7(5):395-397.
Lee et al. "Highly Multiplexed Subcellular RNA Sequencing In Situ", Science (2014) 343(6177):1360-1363.
Levene et al. "Zero-mode waveguides for single-molecule analysis at high concentrations." science 299.5607 (2003): 682-686.
Levsky et al., "Fluorescence in situ hybridization: past, present and future," J Cell Sci. (2003) 116(Pt 14): 2833-8.
Levsky et al., "Single-cell gene expression profiling," Science. (2002) 297(5582): 836-40.
Li et al., "Chromatin Interaction Analysis with Paired-End Tag (ChIA-PET) sequencing technology and application," BMC Genomics. (2014) 15 Suppl 12(Suppl 12):S11.
Lieberman-Aiden et al. "Comprehensive mapping of long-range interactions reveals folding principles of the human genome." science 326.5950 (2009): 289-293.
Lin et al., "Highly multiplexed imaging of single cells using a high-throughput cyclic immunofluorescence method," Nat Commun. (2015) 6:8390.
Liu et al. Barcoded oligonucleotides ligated on RNA amplified for multiplexed and parallel in situ analyses. Nucleic Acids Res. (2021) 49(10):e58, 15 pages. doi: 10.1093/nar/gkab120.
Lizardi et al., "Mutation detection and single-molecule counting using isothermal rolling-circle amplification," Nat Genet. (1998) 19(3): 225-232.
Lundquist et al. "Parallel confocal detection of single molecules in real time." Optics letters 33.9 (2008): 1026-1028.
Maierhorfer et al., "Multicolor deconvolution microscopy of thick biological specimens," Am J Pathol. (2003) 162(2): 373-9.
Marmur et al. "Strand separation and specific recombination in deoxyribonucleic acids: biological studies." *Proceedings of the National Academy of Sciences of the United States of America* 46.4 (1960): 453.
Maston et al. "Transcriptional regulatory elements in the human genome." *Annu. Rev. Genomics Hum. Genet.* 7 (2006): 29-59.
Maxwell et al. "Pitx3 regulates tyrosine hydroxylase expression in the substantia nigra and identifies a subgroup of mesencephalic dopaminergic progenitor neurons during mouse development." *Developmental biology* 282.2 (2005): 467-479.
McGinn et al., "New technologies for DNA analysis—a review of the READNA Project," N Biotechnol. (2016) 33(3): 311-30. doi: 10.1016/j.nbt.2015.10.003.
Meade et al. "Multiplexed DNA detection using spectrally encoded porous SiO2 photonic crystal particles," Anal Chem. (2009) 81(7): 2618-25.
Mitchell et al. "The genome in three dimensions: a new frontier in human brain research." *Biological psychiatry* 75.12 (2014): 961-969.
Mohsen et al., "The Discovery of Rolling Circle Amplification and Rolling Circle Transcription," Acc Chem Res. (2016) 49(11): 2540-2550.
Nallur et al., "Signal amplification by rolling circle amplification on DNA microarrays," Nucleic Acids Res. (2001) 29(23): e118.
Oeffinger et al. "Comprehensive analysis of diverse ribonucleoprotein complexes." *Nature methods* 4.11 (2007): 951-956.
Orphanides et al. "The general transcription factors of RNA polymerase II." *Genes & development* 10.21 (1996): 2657-2683.
Payne et al. "In situ genome sequencing resolves DNA sequence and structure in intact biological samples," Science. (2021) 371(6532): eaay3446. doi: 10.1126/science.aay3446. Epub Dec. 31, 2020.
Pennacchio et al. "Enhancers: five essential questions." *Nature Reviews Genetics* 14.4 (2013): 288-295.
Pirici et al., "Antibody elution method for multiple immunohistochemistry on primary antibodies raised in the same species and of the same subtype," J Histochem Cytochem. (2009) 57(6); 567-75.
Qian, Xiaoyan, et al. "A spatial atlas of inhibitory cell types in mouse hippocampus." *bioRxiv* (2018): 431957.
Raj et al., "Imaging individual mRNA molecules using multiple singly labeled probes," Nat Methods. (2008) 5(10): 877-879.
Rajeswari et al., "Multiple pathogen biomarker detection using an encoded bead array in droplet PCR," J Microbiol Methods. (2017) 139: 22-28.
Ronaghi et al., "A sequencing method based on real-time pyrophosphate," Science. (1998) 281(5375): 363, 365.
Rouhanifard et al. "ClampFISH detects individual nucleic acid molecules using click chemistry-based amplification," Nat Biotechnol. (2018) 17 pages. doi: 10.1038/nbt.4286.
Sahlen et al. "Genome-wide mapping of promoter-anchored interactions with close to single-enhancer resolution." *Genome biology* 16.1 (2015): 1-13.
Sanderson et al. "Fluorescence microscopy." *Cold Spring Harbor Protocols* Oct. 2014 (2014): pdb-top071795.
Schweitzer et al., "Multiplexed protein profiling on microarrays by rolling-circle amplification," Nature Biotech. (2002) 20:359-365.
Schweitzer et al. "Immunoassays with rolling circle DNA amplification: A versatile platform for ultrasensitive antigen detection," Proc. Natl Acad. Sci. USA (2000) 97:10113-119.
Shendure et al., "Accurate multiplex polony sequencing of an evolved bacterial genome," Science (2005) 309(5741); 1728-1732.
Skene et al. "Targeted in situ genome-wide profiling with high efficiency for low cell numbers." *Nature protocols* 13.5 (2018): 1006-1019.
Soderberg et al. "Characterizing proteins and their interactions in cells and tissues using the in situ proximity ligation assay." *Methods* 45.3 (2008): 227-232.
Splinter et al. "3C technology: analyzing the spatial organization of genomic loci in vivo." Methods in enzymology 375 (2004): 493-507.
Stougaard et al. "Strategies for highly sensitive biomarker detection by Rolling Circle Amplification of signals from nucleic acid composed sensors." *Integrative Biology* 3.10 (2011): 982-992.
Sun et al., "Composite organic-inorganic nanoparticles as Raman labels for tissue analysis," Nano Lett. (2007) 7(2): 351-6.
Takei et al., (Feb. 2021, e-pub Jan. 27, 2021). "Integrated Spatial Genomics Reveals Global Architecture of Single Nuclei," Nature 590(7845):344-350, 53 pages. doi: 10.1038/s41586-020-03126-2.
Toh et al. "Immune regulation by CD52-expressing CD4 T cells." *Cellular & molecular immunology* 10.5 (2013): 379-382.
Velazquez et al. "Chronic Dyrk1 inhibition delays the onset of AD-like pathology in 3xTg-AD mice." *Molecular neurobiology* 56.12 (2019): 8364-8375.
Wählby et al., "Sequential immunofluorescence staining and image analysis for detection of large numbers of antigens in individual cell nuclei," Cytometry. (2002) 47(1): 32-41.
Weibrecht et al., "Simultaneous visualization of both signaling cascade activity and end-point gene expression in single cells," PLoS One. (2011) 6(5): e20148.
Wilson et al., "Encoded microcarriers for high-throughput multiplexed detection," Angew Chem Int Ed Engl. (2006) 18;45(37): 6104-17.
Wu, C. et al. "RollFISH Achieves Robust Quantification of Single-Molecule RNA Biomarkers in Paraffin-Embedded Tumor Tissue Samples," Commun Biol. (2018) 1:(209):1-8. doi: 10.1038/s42003-018-0218-0.
Yaroslavsky et al., "Fluorescence imaging of single-copy DNA sequences within the human genome using PNA-directed padlock probe assembly," Chem Biol. (2013) 20(3): 445-453.
Zhao et al., "Advances of multiplex and high throughput biomolecular detection technologies based on encoding microparticles," Sci China Chem. (2011) 54(8):1185.

\* cited by examiner

SEQUENCE LISTING

<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: Synthetic Construct

<400> SEQUENCE: 1
accaaagtgt gcaaactgcc                                                     20

<210> SEQ ID NO 2
<211> LENGTH: 20
<212> TYPE: DNA
<213> ORGANISM: Artificial Sequence
<220> FEATURE:
<223> OTHER INFORMATION: Synthetic Construct

<400> SEQUENCE: 2
gaacccagtc tatgccccac                                                     20

<210> SEQ ID NO 3
<211> LENGTH: 20
<212> TYPE: DNA
<213> ORGANISM: Artificial Sequence
<220> FEATURE:
<223> OTHER INFORMATION: Synthetic Construct

<400> SEQUENCE: 3
agcctgaatc gagcagaacc                                                     20

<210> SEQ ID NO 4
<211> LENGTH: 20
<212> TYPE: DNA
<213> ORGANISM: Artificial Sequence
<220> FEATURE:
<223> OTHER INFORMATION: Synthetic Construct

<400> SEQUENCE: 4
cccagcatgt aggaggcaaa                                                     20

<210> SEQ ID NO 5
<211> LENGTH: 20
<212> TYPE: DNA
<213> ORGANISM: Artificial Sequence
<220> FEATURE:
<223> OTHER INFORMATION: Synthetic Construct

<400> SEQUENCE: 5
gtctcagcct tagccctgtg                                                     20

<210> SEQ ID NO 6
<211> LENGTH: 30
<212> TYPE: DNA
<213> ORGANISM: Artificial Sequence
<220> FEATURE:
<223> OTHER INFORMATION: Synthetic Construct

<400> SEQUENCE: 6
gcctcttctt agacgacctg tgacgaaccc                                           30

<210> SEQ ID NO 7
<211> LENGTH: 20
<212> TYPE: DNA
<213> ORGANISM: Artificial Sequence

```
<220> FEATURE:
<223> OTHER INFORMATION: Synthetic Construct

<400> SEQUENCE: 7
tcgtctttcc aactctgcgt                                               20

<210> SEQ ID NO 8
<211> LENGTH: 24
<212> TYPE: DNA
<213> ORGANISM: Artificial Sequence
<220> FEATURE:
<223> OTHER INFORMATION: Synthetic Construct

<400> SEQUENCE: 8 cacccoctga agttatgggg cgac                                          24
```

IN SITU ANALYSIS OF CHROMATIN INTERACTION

CROSS-REFERENCE TO RELATED APPLICATION

This application claims priority to U.S. Provisional Patent Application No. 62/977,512, filed Feb. 17, 2020, entitled "METHOD FOR SPATIAL ANALYSIS OF CHROMATIN INTERACTION EVENTS PERFORMED IN SITU," which is herein incorporated by reference in its entirety for all purposes.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 202412006400SEQLIST.TXT, date recorded: Feb. 12, 2021, size: 2 KB).

FIELD

The present disclosure relates in some aspects to methods for analyzing chromatin interaction events involving nucleic acid sequences within a cell or system.

BACKGROUND

Deoxyribonucleic acid (DNA) is usually viewed as a linear molecule with little attention paid to three-dimensional organization. But chromosomes are not rigid, and while the linear distance between two genomic loci may be great, when folded, the spatial distance may be small. For example, while regions of chromosomal DNA organized in three-dimensional chromatin structure, may be separated by many megabases, they also can be immediately adjacent in three-dimensional space.

Regulatory elements (e.g., gene enhancers, silencers, and insulator elements) are short fragments which may contain one or more binding sites for transcription factors that activate or repress genes. Regulatory elements are frequently located far from their target genes and, although they can be recognized by the binding of specific factors, it is often not clear with which genes they interact. However, in the spatial organization of the genome, they are proximate to their target genes.

Understanding how nucleic acids interact, and perhaps more importantly how this interaction, or lack thereof, regulates cellular processes, is a relatively new area of exploration. For example, understanding chromosomal folding and the patterns therein can provide insight into the complex relationships between chromatin structure, gene activity, and the functional state of the cell. In the case of oncogenes and other disease-associated genes, identification of long-range genetic regulators would be of great use in identifying the genomic variants responsible for the disease state and the process by which the disease state is brought about.

Chromatin interaction studies that examine how regulatory elements, such as promoters and enhancers, work across the genome to regulate functions such as transcription are known. But, to date, examining chromatin interaction events in situ with spatial resolution across a tissue section has not been performed. Such a strategy would reveal concerted activity across cell populations in a tissue sample across target regulatory element interactions in the genome. Thus, there is a need for an improved method for analyzing in situ the interaction of target regulatory regions in three-dimensional chromatin structure across cell populations in a tissue sample, and the present disclosure addresses this and other needs.

BRIEF SUMMARY

In some aspects, provided herein is a method for analyzing chromatin interaction, comprising: (a) contacting a sample with a first probe and a second probe simultaneously or sequentially in either order, wherein: the sample comprises a first chromatin region and a second chromatin region in proximity to each other, wherein the proximity is associated with a chromatin interaction event between the first and second chromatin regions in a cell, the first probe hybridizes to a first nucleic acid strand in the first chromatin region and the second probe hybridizes to a second nucleic acid strand in the second chromatin region, and the first and second probes are bridged by one another or by one or more bridging probes; and (b) connecting the ends of the first and/or second probes or the ends of the one or more bridging probes to form a circular probe, wherein the circular probe comprises a sequence of the first nucleic acid strand or complement thereof and/or a sequence of the second nucleic acid strand or complement thereof, wherein an amplification product of the circular probe is detected, thereby analyzing the chromatin interaction event.

In some embodiments, the first and second chromatin regions can be in the same molecule, e.g., the same chromosome in the cell. In some embodiments, the first and second chromatin regions may not overlap in nucleic acid sequence and may not be directly linked by a common phosphodiester bond in the cell. In some embodiments, the genomic distance between the first and second chromatin regions can be at least 0.5 kb, 1 kb, 2 kb, 5 kb, 10 kb, 15 kb, 20 kb, 25 kb, 30 kb, 35 kb, 40 kb, 45 kb, 50 kb, 100 kb, 150 kb, or 200 kb, or in any range in between, or more than 200 kb.

In some embodiments, the first and second chromatin regions can be in different molecules, e.g., different chromosomes in the cell.

In any of the preceding embodiments, the first and/or second chromatin regions can comprise chromosomal nucleic acid, e.g., chromosomal DNA in heterochromatin or euchromatin.

In any of the preceding embodiments, the first and/or second chromatin regions can be in a nucleosome region or a nucleosome-free region, e.g., in a cellular compartment such as a nucleus or mitochondrion.

In any of the preceding embodiments, the first and/or second chromatin regions can be in a 30 nm fiber, an interphase chromosome, a metaphase chromosome, a telomere, or a centromere.

In any of the preceding embodiments, the first and/or second chromatin regions can comprise a regulatory element.

In any of the preceding embodiments, the first and/or second chromatin regions can comprise a promoter or element thereof (e.g., a core promoter element or a proximal promoter element) and/or a long-range regulatory element (e.g., an enhancer, a silencer, an insulator, or a locus control region (LCR)). In any of the preceding embodiments, the first and second probes can hybridize to a promoter sequence and an enhancer sequence, respectively, or vice versa.

In any of the preceding embodiments, the chromatin interaction event can be mediated by one or more chromatin associated factors. In any of the preceding embodiments, the one or more chromatin associated factors can comprise a polynucleotide (e.g., a DNA or RNA), a polypeptide (e.g., a protein or peptide), a carbohydrate, a lipid, a small molecule, and/or a conjugate, derivative, metabolite, or analogue thereof. In any of the preceding embodiments, the one or more chromatin associated factors can comprise a transcription factor, an activator, a repressor, a chromatin-remodeler, a polymerase, a replication factor, a DNA repair factor, a histone (e.g., histones comprising post-translational modifications), a histone-modifying enzyme, a DNA-modifying enzyme (e.g., DNA methylases), and/or a cofactor or complex thereof.

In any of the preceding embodiments, the chromatin interaction event can occur prior to or during the contacting step. In any of the preceding embodiments, the chromatin interaction event can hold the first and second chromatin regions together in a chromatin conformation. In any of the preceding embodiments, the method can further comprise preserving or capturing the chromatin conformation.

In any of the preceding embodiments, the method can further comprise treating the sample with a cross-linking agent prior to the contacting step. In any of the preceding embodiments, nucleic acid in the first and/or second chromatin regions can be cross-linked to one another and/or to one or more chromatin associated factors by the cross-linking agent. In any of the preceding embodiments, the cross-linking agent can comprise formaldehyde, UV radiation, glutaraldehyde, bis(imido esters), bis(succinimidyl esters), diisocyanates, diacid chlorides, 1-Ethyl-3-(3-dimethylaminopropyl)carbodiimide, mitomycin C, nitrogen mustard, melphalan, 1,3-butadiene diepoxide, cis diaminedichloroplatinum (II), cyclophosphamide, disuccinimidyl-glutarate, or dithiobis-succinimidyl propionate, or any combination thereof.

In any of the preceding embodiments, the first nucleic acid strand can be a sense strand or antisense strand, and/or wherein the second nucleic acid strand can be a sense strand or antisense strand. For instance, the first and second nucleic acid strands can be both sense strands, or the first and second nucleic acid strands can be both antisense strands. In other examples, the first nucleic acid strand is a sense strand and the second nucleic acid strand is an antisense strand, or vice versa.

In any of the preceding embodiments, the first and/or second probes can be chromatin accessing probes, e.g., opening probes such as PNA probes that open up a DNA duplex in chromatin to provide single-stranded binding sites for further probes. In any of the preceding embodiments, the complementary strand to the first nucleic acid strand in the first chromatin region and/or the complementary strand to the second nucleic acid strand in the second chromatin region may be hybridized to one or more further probes, such as a detection probe with "handles" (e.g., 3' and/or 5' overhangs that do not hybridize to chromatin DNA) and/or a further chromatin accessing probe. In any of the preceding embodiments, the complementary strand to the first nucleic acid strand in the first chromatin region and/or the complementary strand to the second nucleic acid strand in the second chromatin region may not be hybridized to a further probe, e.g., a further chromatin accessing probe.

In any of the preceding embodiments, the complementary strand to the first nucleic acid strand in the first chromatin region can be hybridized to a first chromatin accessing probe, and/or wherein the complementary strand to the second nucleic acid strand in the second chromatin region can be hybridized to a second chromatin accessing probe.

In any of the preceding embodiments, the chromatin accessing probe (e.g., the first and/or second chromatin accessing probes that target the first and second chromatin regions, respectively) can comprise one or more natural nucleic acid residues and/or one or more residues of one or more synthetic nucleic acid analogues. In any of the preceding embodiments, the one or more synthetic nucleic acid analogues can comprise xeno nucleic acids (XNAs) and can optionally comprise 1,5-anhydrohexitol nucleic acid (HNA), cyclohexene nucleic acid (CeNA), threose nucleic acid (TNA), glycol nucleic acid (GNA), locked nucleic acid (LNA), peptide nucleic acid (PNA), or fluoro arabino nucleic acid (FANA), or any combination thereof.

In any of the preceding embodiments, the chromatin accessing probe (e.g., the first and/or second chromatin accessing probes) can comprise one or more peptide nucleic acid (PNA) residues. In any of the preceding embodiments, the first and/or second chromatin accessing probes can be PNA probes, and the method can further comprise a step of contacting the sample with the first and second chromatin accessing probes simultaneously or sequentially in either order. In any of the preceding embodiments, the sample can be contacted with the first and/or second chromatin accessing probes prior to contacting the sample with the first and/or second probes.

In any of the preceding embodiments, the melting temperature (Tm) of the hybridization between the first or second nucleic acid strand and the corresponding complementary strand can be lower than the $T_m$ of the hybridization between the first or second chromatin accessing probe and the corresponding complementary strand, e.g., by about 5° C., about 10° C., about 15° C., about 20° C., about 25° C., about 30° C., about 35° C., about 40° C., about 45° C., about 50° C., or by more than 50° C. In some embodiments, such differences in $T_m$ allow a chromatin accessing probe to separate the strands of a duplex in chromatin. The chromatin accessing probe can be stably hybridized to a nucleic acid strand in chromatin, rendering the other strand of the unwound duplex single-stranded and accessible to one or more further probes, such as a detection probe with 5' and/or 3' overhangs.

In any of the preceding embodiments, the sample can be contacted with the chromatin accessing probe (e.g., the first and/or second chromatin accessing probes) under conditions that allow probe access to single-stranded sequences in the first and/or second chromatin regions. Probe access may include access by the chromatin accessing probe and/or a further probe, such as a detection probe and/or a further chromatin accessing probe. Under such conditions, the chromatin accessing probe may not comprise XNA (e.g., PNA) residues and may consist of natural nucleic acid residues. In any of the preceding embodiments, the sample can be contacted with the chromatin accessing probe (e.g., a PNA probe or a probe of natural nucleic acid residues) at a chromatin accessing probe concentration of at least 100 nM, 200 nM, 500 nM, 1 µM, 2 µM, or more than 2 µM, which may facilitate the opening of duplexes in chromatin by the chromatin accessing probe to provide single-stranded binding sites for one or more further probes. In any of the preceding embodiments, the sample can be contacted with the chromatin accessing probe (e.g., a PNA probe or a probe of natural nucleic acid residues) at a temperature of at least 40° C., 45° C., 50° C., or more than 50° C., which may facilitate the opening of duplexes in chromatin to provide single-stranded binding sites for the chromatin accessing probe and/or a further probe. In any of the preceding embodiments, the sample can be incubated with the chromatin accessing probe for at least 30 minutes, 1 hours, 2 hours, 5 hours, or more than 5 hours, and the incubation may facilitate the opening of duplexes in chromatin to provide single-stranded binding sites for the chromatin accessing probe and/or a further probe.

The chromatin accessing probe may be a detection probe (e.g., a probe having 5' and/or 3' overhangs upon binding to a single-stranded region in chromatin). In some embodiments, the chromatin accessing probe itself is not a detection probe, and upon binding to a single-stranded region in chromatin, may comprise no overhang, or comprise only one overhang (3' or 5'), or comprise 3' and 5' overhangs, where the 3' and/or 5' overhangs may facilitate the formation of the circular probe but do not form part of the circular probe.

In any of the preceding embodiments, the method can further comprise removing molecules of the chromatin accessing probe that are not specifically hybridized, e.g., using one or more washes such as a stringency wash.

In any of the preceding embodiments, the method can further comprise removing molecules of the first and/or second probes and/or the one or more bridging probes that are not specifically hybridized, e.g., using one or more washes such as a stringency wash.

In any of the preceding embodiments, the first and/or second probes can comprise a 3' overhang and a 5' overhang flanking a sequence hybridized to the first and second nucleic acid strands, respectively.

In any of the preceding embodiments, the 3' overhang of the first probe can be at least partially complementary to the 5' overhang of the second probe, and/or the 5' overhang of the first probe can be at least partially complementary to the 3' overhang of the second probe.

In any of the preceding embodiments, the method can further comprise extending the 3' end of the first probe (e.g., using primer extension and/or ligation) using the second probe as a template, and connecting (e.g., using ligation) the extended 3' end of the first probe to the optionally extended 5' end of the first probe, thereby circularizing the first probe to form the circular probe.

In any of the preceding embodiments, the method can further comprise extending the 3' end of the second probe (e.g., using primer extension and/or ligation) using the first probe as a template, and connecting (e.g., using ligation) the extended 3' end of the second probe to the optionally extended 5' end of the second probe, thereby circularizing the second probe to form the circular probe.

In any of the preceding embodiments, the 3' overhang of the first probe and the 5' overhang of the second probe can be at least partially complementary to a first bridging probe sequence, and the 5' overhang of the first probe and the 3' overhang of the second probe can be at least partially complementary to a second bridging probe sequence, optionally wherein the first and second bridging probe sequences can be in the same bridging probe or in separate bridging probes.

In any of the preceding embodiments, the method can further comprise extending the 3' end of the first probe (e.g., using primer extension and/or ligation) using the bridging probe(s) as a template, and connecting (e.g., using ligation) the extended 3' end of the first probe to the optionally extended 5' end of the second probe.

In any of the preceding embodiments, the method can further comprise extending the 3' end of the second probe (e.g., using primer extension and/or ligation) using the bridging probe(s) as a template, and connecting (e.g., using ligation) the extended 3' end of the second probe to the optionally extended 5' end of the first probe, thereby connecting the first and second probes to form the circular probe.

In any of the preceding embodiments, the first and/or second bridging probe sequences can be in a probe (e.g., a chromatin accessing probe) hybridized to the complementary strand to the first nucleic acid strand in the first chromatin region and/or a probe (e.g., a chromatin accessing probe) hybridized to the complementary strand to the second nucleic acid strand in the second chromatin region.

In any of the preceding embodiments, the 3' overhang of the first probe and the 5' overhang of the second probe can be at least partially complementary to a first bridging probe, and the 5' overhang of the first probe and the 3' overhang of the second probe can be at least partially complementary to a second bridging probe.

In any of the preceding embodiments, the method can further comprise extending the 3' end of the first bridging probe (e.g., using primer extension and/or ligation) using the first probe as a template, and connecting (e.g., using ligation) the extended 3' end of the first bridging probe to the optionally extended 5' end of the second bridging probe.

In any of the preceding embodiments, the method can further comprise extending the 3' end of the second bridging probe (e.g., using primer extension and/or ligation) using the second probe as a template, and connecting (e.g., using ligation) the extended 3' end of the second bridging probe to the optionally extended 5' end of the first bridging probe, thereby connecting the first and second bridging probes to form the circular probe.

In any of the preceding embodiments, the circular probe can be formed in situ in the sample.

In any of the preceding embodiments, the first probe, the second probe, the bridging probe, the circular probe, and/or the chromatin accessing probe can comprise a barcode sequence. In any of the preceding embodiments, the circular probe can comprise one or more barcode sequences that correspond to a nucleic acid sequence of interest, e.g., in the first chromatin region and/or in the second chromatin region. In any of the preceding embodiments, the amplification product can comprise multiple copies of the one or more barcode sequences or a complement thereof, the sequence of the first nucleic acid strand or complement thereof, and the sequence of the second nucleic acid strand or complement thereof.

In any of the preceding embodiments, the amplification product can be formed in situ in the sample.

In any of the preceding embodiments, the amplification product can be formed using rolling circle amplification (RCA) of the circular probe, optionally wherein the RCA can be a linear RCA, a branched RCA, a dendritic RCA, or any combination thereof, and optionally wherein the amplification product can be formed using a Phi29 polymerase, wherein the amplification can be performed at a temperature between about 20° C. and about 60° C., optionally between about 30° C. and about 40° C.

In any of the preceding embodiments, the detecting of the amplification product can comprise labeling the amplification product with a fluorophore, an isotope, a mass tag, or a combination thereof.

In any of the preceding embodiments, the detecting of the amplification product can comprise directly or indirectly hybridizing one or more probes to the amplification product, optionally wherein a fluorescently labeled probe can be directly hybridized to the amplification product, or optionally wherein a fluorescently labeled probe can be directly hybridized to an intermediate probe which can be hybridized to the amplification product.

In any of the preceding embodiments, the amplification product can be detected in situ in the sample.

In any of the preceding embodiments, the detecting of the amplification product can comprise imaging the sample, e.g., using fluorescent microscopy.

In any of the preceding embodiments, the detecting of the amplification product can comprise determining a sequence of the amplification product, e.g., by sequencing all or a portion of the amplification product and/or in situ hybridization (e.g., sequential fluorescence in situ hybridization) to the amplification product.

In any of the preceding embodiments, the sequencing can comprise sequencing by hybridization, sequencing by ligation, sequencing by synthesis, and/or sequencing by binding.

In any of the preceding embodiments, the sample can be a tissue sample, e.g., a non-homogenized tissue sample, such as a tissue slice optionally between about 1 μm and about 50 μm in thickness, e.g., between about 5 μm and about 35 μm in thickness.

In any of the preceding embodiments, the sample can be a processed or cleared sample.

In any of the preceding embodiments, the sample can be fixed or not fixed, e.g., a formalin-fixed, paraffin-embedded (FFPE) sample, a frozen tissue sample, or a fresh tissue sample.

In any of the preceding embodiments, the sample can be on a substrate such as a slide.

In any of the preceding embodiments, the sample can be embedded in a matrix, e.g., a hydrogel functionalized for attaching biomolecules and/or products thereof from the sample.

In any of the preceding embodiments, the sample can be analyzed to detect a plurality of chromatin interaction events, e.g., in parallel or sequentially.

In any of the preceding embodiments, a first circular probe can be associated with a first chromatin interaction event and a second circular probe can be associated with a second chromatin interaction event, and the first and second circular probe each can comprise a barcode sequence or complement thereof that can correspond to the first and/or second probe or the chromatin interaction event.

In any of the preceding embodiments, the chromatin interaction event can involve one or more chromatin regions other than the first and second chromatin regions, and the circular probe can further comprise a sequence or complement thereof of a nucleic acid strand in the one or more other chromatin regions.

In some aspects, provided herein is a method for analyzing chromatin interaction, comprising: (a) contacting a sample with a first chromatin accessing probe and a second chromatin accessing probe simultaneously or sequentially in either order, wherein: the sample comprises a first chromatin region and a second chromatin region in proximity to each other, wherein the proximity is associated with a chromatin interaction event between the first and second chromatin regions in a cell, and the first chromatin accessing probe hybridizes to the complementary strand of a first nucleic acid strand in the first chromatin region and the second chromatin accessing probe hybridizes to the complementary strand of a second nucleic acid strand in the second chromatin region, thereby allowing access to the first and second nucleic acid strands for further probes (e.g., by providing single-stranded binding sites in the first and second nucleic acid strands for further probes); (b) contacting the sample with a first probe and a second probe simultaneously or sequentially in either order, wherein: the first probe hybridizes to the first nucleic acid strand and the second probe hybridizes to the second nucleic acid strand; (c) contacting the sample with a first bridging probe that bridges the 3' end of the first probe and the 5' end of the second probe, and a second bridging probe that bridges the 3' end of the second probe and the 5' end of the first probe; (d) circularizing the first and second bridging probes using the first and second probes as templates to form a circular probe, wherein the circular probe comprises a sequence of the first nucleic acid strand and a sequence of the second nucleic acid strand; (e) generating a rolling circle amplification (RCA) product of the circular probe in situ in the sample; and (f) detecting the RCA product, thereby analyzing the chromatin interaction event.

In any of the preceding embodiments, the chromatin interaction event can hold the first and second chromatin regions together in a chromatin conformation, and the method can further comprise preserving or capturing the chromatin conformation with a cross-linking agent prior to (a). In any of the preceding embodiments, the first and second chromatin accessing probes can be peptide nucleic acid (PNA) probes. In any of the preceding embodiments, the first and second probes may not displace the first and second chromatin accessing probes from the first and second chromatin regions, respectively. In some aspects, the sample is contacted with the first and second chromatin accessing probes prior to contact with the first and second probes. The chromatin accessing probes may stably bind to the complementary strands, such that the first and second nucleic acid strands in chromatin are rendered single-stranded, thereby providing binding sites for the first and second probes. In some aspects, the first and second probes bind to the first and second nucleic acid strands rather than the first and second chromatin accessing probes. In some embodiments, the affinity of the chromatin accessing probes binding to the complementary strands is greater than the affinity of the nucleic acid strands in chromatin binding to their complementary strands, whereby the chromatin accessing probes open up duplexes in chromatin. In some embodiments, the affinity of the chromatin accessing probes binding to the complementary strands is greater than the affinity of the detection probes (e.g., the first and second probes) to the chromatin accessing probes, such that the chromatin accessing probes and the first and second probes bind to strands in the chromatin instead of forming chromatin accessing probe/detection probe duplexes.

In any of the preceding embodiments, the method can be used for spatial analysis of chromatin interaction events in situ. In some embodiments, the chromatin interaction events are across cell populations in a biological sample.

In some aspects, provided herein is a kit, comprising: a first probe capable of hybridizing to a first nucleic acid strand in a first chromatin region, and a second probe capable of hybridizing to a second nucleic acid strand in a second chromatin region, wherein: the first chromatin region and the second chromatin region are known to engage or suspected of engaging in a chromatin interaction event in a cell; upon hybridization to the first and second nucleic acid strands in a sample in which a chromatin conformation associated with the chromatin interaction event is preserved or captured, the first and second probes are bridged by one another or by one or more bridging probes; and upon connection of the ends of the first and/or second probes or the ends of the one or more bridging probes, a circular probe is formed and the circular probe comprises a sequence of the first nucleic acid strand or complement thereof and/or a sequence of the second nucleic acid strand or complement thereof. In some embodiments, the kit further comprises the one or more bridging probes. In some aspects, provided herein is a kit for analyzing a plurality of chromatin interaction events, comprising multiple sets of the first probe, the second probe, and optionally the one or more bridging probes, wherein each set is for analyzing a different chromatin interaction event.

In some aspects, provided herein is a kit, comprising: (i) a first chromatin accessing probe and a second chromatin accessing probe, wherein: the first chromatin accessing probe is capable of hybridizing to the complementary strand of a first nucleic acid strand in a first chromatin region; the second chromatin accessing probe is capable of hybridizing to the complementary strand of a second nucleic acid strand in a second chromatin region; and the first chromatin region and the second chromatin region are known to engage or suspected of engaging in a chromatin interaction event in a cell; (ii) a first detection probe and a second detection probe, wherein: the first detection probe is capable of hybridizing to the first nucleic acid strand and the second detection probe is capable of hybridizing to the second nucleic acid strand; and (iii) a first bridging probe capable of bridging the 3' end of the first detection probe and the 5' end of the second detection probe, and a second bridging probe capable of bridging the 3' end of the second detection probe and the 5' end of the first detection probe; upon hybridization to the first and second nucleic acid strands in a sample in which a chromatin conformation associated with the chromatin interaction event is preserved or captured, the first and second detection probes are bridged by the first and second bridging probes; and upon connection of the ends of the first and second bridging probes using the first and second detection probes as templates, a circular probe is formed and the circular probe comprises a sequence of the first nucleic acid strand and a sequence of the second nucleic acid strand. In any of the preceding embodiments, the first and second chromatin accessing probes can be peptide nucleic acid (PNA) probes. In some aspects, provided herein is a kit for analyzing a plurality of chromatin interaction events, comprising multiple sets of the first and second chromatin accessing probes, the first and second detection probes, and/or the first and second bridging probes, wherein each set is for analyzing a different chromatin interaction event.

In any of the preceding embodiments, the kit can further comprise an enzyme which optionally comprises a polymerase (e.g., a Phi29 polymerase) and/or a ligase.

In some embodiments, the method comprises: a) obtaining a biological sample; b) hybridizing a first set of probes (e.g., one or more chromatin accessing probes) comprising at least two unique oligonucleotide sequences to a sense or antisense strand (e.g., the complementary strand of a first or second nucleic acid strand in chromatin) of at least two primary target nucleic acid sequences, wherein said at least two primary target nucleic acid sequences (e.g., first and second chromatin regions) are engaged in a chromatin interaction event; c) hybridizing a second set of probes (e.g., the first and second probes for the first and second chromatin regions, such as detection probes with overhangs) comprising at least two unique oligonucleotide sequences to a sense or antisense strand (e.g., the first or second nucleic acid strand) of said at least two primary target nucleic acid sequences; d) hybridizing a third set of probes (e.g., one or more bridging probes or circularizing probes) to said second probe set, wherein said second probes are spatially proximate to one another due to being hybridized to at least two primary target nucleic acid sequences engaged in a chromatin interaction event and wherein said third probes (e.g., one or more bridging probes or circularizing probes) bridge the ends of said second probes; e) extending the third set of probes (e.g., one or more bridging probes or circularizing probes) with a polymerase to form a circularized nucleic acid comprising at least a portion of the at least two primary target nucleic acid sequences engaged in a chromatin interaction event; f) amplifying said circular nucleic acid to generate a population of amplicons comprising signal producing tags detectable in situ; and g) detecting said population of tagged amplicons in situ by said signal producing tags.

In some embodiments, the method can be multiplexed and comprise the steps of quenching the signal generated from said signal producing tags; and repeating steps b)-g) wherein said first and second sets of probes each comprise at least two unique oligonucleotide sequences that hybridize to a sense or antisense strand of at least two secondary target nucleic acid sequences engaged in a chromatin interaction event. In some embodiments, the method comprises quenching the signal from said signal producing tags. In some embodiments, the method comprises repeating steps b)-g) for a number of successive rounds wherein each successive round comprises a first and second set of probes with different oligonucleotide sequences than the first and second set of probes used in other rounds and wherein the first and second set of probes hybridize to different target nucleic acid sequences than the target nucleic acid sequences in other rounds.

In one embodiment, the chromatin is chemically cross-linked within said biological sample to chromatin associated factors with a cross-linking agent. In some embodiments, chromatin DNA is cross-linked to chromatin associated factors. In one embodiment, the cross-linking agent can be selected from the group comprising formaldehyde, UV radiation, glutaraldehyde, bis(imido esters), bis(succinimidyl esters), diisocyanates, diacid chlorides, and 1-Ethyl-3-(3-dimethylaminopropyl)carbodiimide. In an alternative embodiment, the chromatin is not cross-linked to chromatin associated factors.

In one embodiment, the primary target nucleic acid sequences comprise genomic DNA. In some embodiments, the primary target nucleic acid sequences comprise a target promoter DNA sequence and a target enhancer DNA sequence.

In some embodiments, one of said first set of probes (e.g., a chromatin accessing probe for a first chromatin region) and one of said second set of probes (e.g., a first probe such as a detection probe for a first chromatin region) hybridize to the target promoter DNA sequence and wherein one of said first set of probes (e.g., a chromatin accessing probe for a second chromatin region) and one of said second set of probes (e.g., a second probe such as a detection probe for a second chromatin region) hybridize to the target enhancer DNA sequence. For example, the first chromatin region comprises the target promoter sequence or a portion thereof, whereas the second chromatin region comprises the target enhancer sequence or a portion thereof, or vice versa. In one embodiment, the first set of probes (e.g., a chromatin accessing probe) comprise peptide nucleic acid probes or PNAs. In another embodiment, the second set of probes comprise detection probes comprising 3' and 5' overhangs. In another embodiment, the third set of probes (e.g., one or more bridging probes or circularizing probes) comprise complementary sequences to said 3' and 5' overhangs of said second set of probes and hybridize to the same to form said bridge.

In some embodiments, said amplifying step is carried out by rolling circle amplification and said amplicon is chemically labeled. In one embodiment, the amplicon is chemically labeled with fluorescently labeled probes. In another embodiment, the detection step comprises fluorescence in situ hybridization.

In some embodiments, the method involves preparing a carrier substrate comprising the biological sample. In one embodiment, the carrier substrate a slide having said biological sample thereon. In one embodiment, the biological sample is fixed by a fixative. In an alternative embodiment, the biological sample is not fixed.

In some embodiments, chromatin associated factors can comprise proteins, DNA, RNA, small molecules, and metabolites. In one embodiment, the chromatin associated factor is a transcription factor.

In some embodiments, the method further comprises the step of sequencing said one or more populations of amplicons by in situ sequencing.

In another embodiment the method for spatial analysis of chromatin interaction events in situ comprises the steps of preparing a tissue sample on a suitable carrier substrate; cross-linking chromatin within said tissue sample to chromatin associated factors by a cross-linking agent; hybridizing a first oligonucleotide set (e.g., one or more probes that hybridizes to a nucleic acid strand in a chromatin region, e.g., detection probes) comprising at least two unique oligonucleotide sequences to a first strand of at least two target nucleic acid sequences, wherein said at least two target nucleic acid sequences are engaged in a chromatin interaction event; hybridizing a second oligonucleotide set (e.g., one or more bridging probes or circularizing probes) to said first oligonucleotide set, wherein said first oligonucleotides are proximate to one another due to being hybridized to at least two target nucleic acid sequences engaged in a chromatin interaction event and wherein said second oligonucleotides bridge the ends of said first oligonucleotides; extending the second oligonucleotides to form a circular oligonucleotide comprising at least a portion of the at least two target nucleic acid sequences engaged in a chromatin interaction event; amplifying said circular oligonucleotide to generate a population of amplicons detectable in situ; and detecting said amplicon in situ.

In yet another embodiment, the method for spatial analysis of chromatin interaction events in situ comprises the steps of: a) obtaining a biological sample from at least one subject; b) preparing a carrier substrate comprising said biological sample; c) cross-linking chromatin within said biological sample to chromatin associated factors with a cross-linking agent; d) hybridizing a plurality of probes to a plurality of primary target nucleic acid sequences in situ engaged in a chromatin interaction events, wherein said plurality of probes comprise at least detection probes that hybridize to circularizing probes; e) extending the circularizing probes with a polymerase to form circularized nucleic acids comprising at least a portion of the primary target nucleic acid sequences engaged in a chromatin interaction event; f) amplifying said circular nucleic acids to generate one or more populations of amplicons, each said population of amplicons comprising a signal producing tag detectable in situ; and g) detecting said populations of tagged amplicons in situ by said signal producing tags.

In some embodiments, signal producing tags are unique to one or more populations of amplicons and capable of distinguishing one population from another.

BRIEF DESCRIPTION OF THE DRAWINGS

Representative embodiments of the invention are disclosed by reference to the following figures.

DETAILED DESCRIPTION

Figure 1:
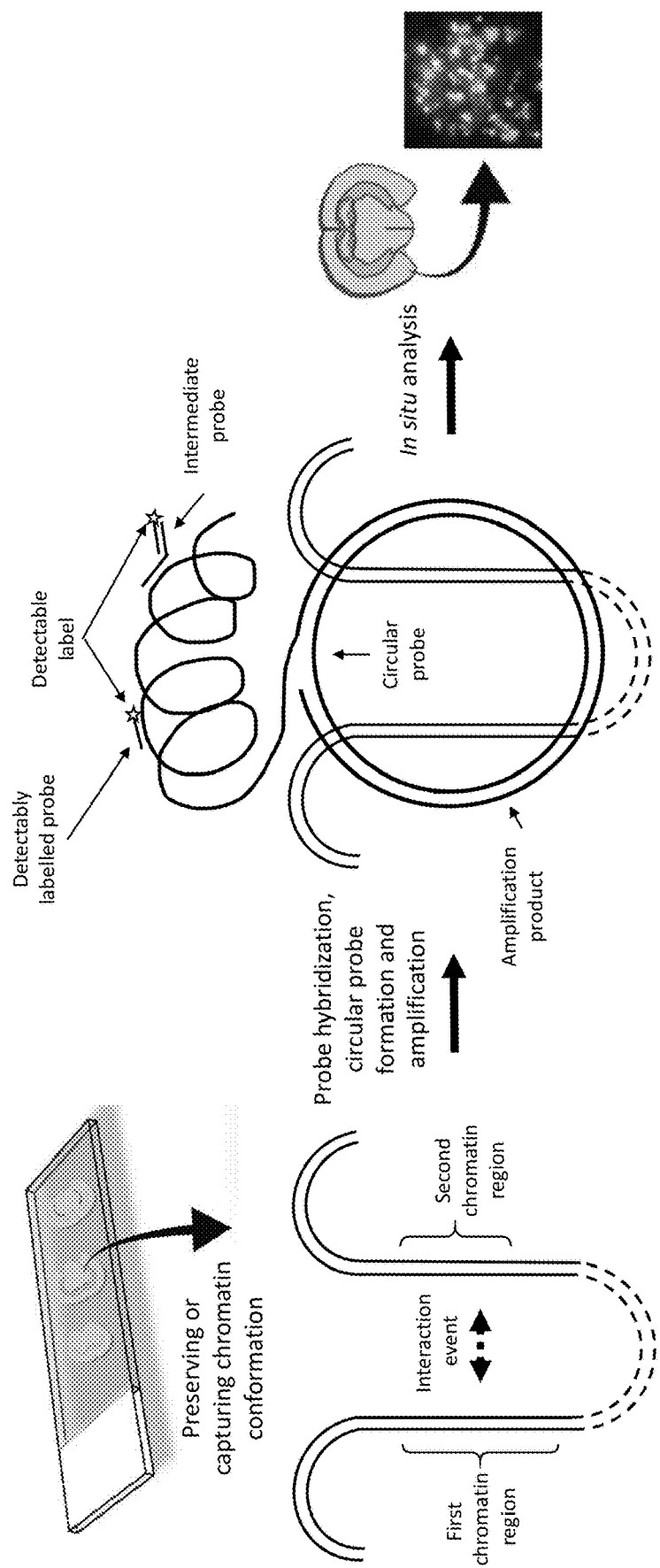
FIG. 1 shows an exemplary method for analysis of chromatin interaction events between a first and second chromatin region in situ in a biological tissue sample. Dashed lines indicate the first and second chromatin regions may be in the same molecule or in different molecules (e.g., different chromosomes).

All publications, comprising patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The section headings used herein are for organizational purposes only and are not to be construed as limiting the subject matter described.

I. SAMPLES AND ANALYTES

A. Samples and Sample Processing

A sample disclosed herein can be or derived from any biological sample in which analysis of chromatin interaction is desirable. Methods and compositions disclosed herein may be used for analyzing a biological sample, which may be obtained from a subject using any of a variety of techniques including, but not limited to, biopsy, surgery, and laser capture microscopy (LCM), and generally includes cells and/or other biological material from the subject. A biological sample can also be obtained from non-mammalian organisms (e.g., a plant, an insect, an arachnid, a nematode, a fungus, or an amphibian). A biological sample can also be obtained from a eukaryote, such as a tissue sample, a patient derived organoid (PDO) or patient derived xenograft (PDX). A biological sample from an organism may comprise one or more other organisms or components therefrom. For example, a mammalian tissue section may comprise a prion, a viroid, a virus, a bacterium, a fungus, or components from other organisms, in addition to mammalian cells and non-cellular tissue components. Subjects from which biological samples can be obtained can be healthy or asymptomatic individuals, individuals that have or are suspected of having a disease (e.g., a patient with a disease such as cancer) or a predisposition to a disease, and/or individuals in need of therapy or suspected of needing therapy.

The biological sample can include any number of macromolecules, for example, cellular macromolecules and organelles (e.g., mitochondria and nuclei). The biological sample can be obtained as a tissue sample, such as a tissue section, biopsy, a core biopsy, needle aspirate, or fine needle aspirate. The sample can be a fluid sample, such as a blood sample, urine sample, or saliva sample, and cells and cellular components therein such as chromatin may be analyzed after placing the cells or cellular components on a substrate. The sample can be a skin sample, a colon sample, a cheek swab, a histology sample, a histopathology sample, a plasma or serum sample, a tumor sample, living cells, cultured cells, a clinical sample such as, for example, whole blood or blood-derived products, blood cells, or cultured tissues or cells, including cell suspensions. In some embodiments, the biological sample may comprise cells which are deposited on a surface and the cells can be isolated from a bodily sample, e.g., blood, plasma, serum, urine, saliva, mucosal excretions, sputum, stool, and tears.

Biological samples can be derived from a homogeneous culture or population of the subjects or organisms mentioned herein or alternatively from a collection of several different organisms, for example, in a community or ecosystem.

Biological samples can include one or more diseased cells. A diseased cell can have altered metabolic properties, gene expression, protein expression, and/or morphologic features. Examples of diseases include inflammatory disorders, metabolic disorders, nervous system disorders, and cancer. Cancer cells can be derived from solid tumors, hematological malignancies, cell lines, or obtained as circulating tumor cells. Biological samples can also include fetal cells and immune cells.

Biological samples can include analytes (e.g., protein, RNA, and/or DNA) in a 3D matrix. In some embodiments, amplicons (e.g., rolling circle amplification products) derived from or associated with analytes (e.g., protein, RNA, and/or DNA) can be embedded in a 3D matrix. In some embodiments, a 3D matrix may comprise a network of natural molecules and/or synthetic molecules that are chemically and/or enzymatically linked, e.g., by crosslinking. In some embodiments, a 3D matrix may comprise a synthetic polymer. In some embodiments, a 3D matrix comprises a hydrogel.

In some embodiments, a substrate herein can be any support that is insoluble in aqueous liquid and which allows for positioning of biological samples, analytes, features, and/or reagents (e.g., probes) on the support. In some embodiments, a biological sample can be attached to a substrate. Attachment of the biological sample can be irreversible or reversible, depending upon the nature of the sample and subsequent steps in the analytical method. In certain embodiments, the sample can be attached to the substrate reversibly by applying a suitable polymer coating to the substrate, and contacting the sample to the polymer coating. The sample can then be detached from the substrate, e.g., using an organic solvent that at least partially dissolves the polymer coating. Hydrogels are examples of polymers that are suitable for this purpose.

In some embodiments, the substrate can be coated or functionalized with one or more substances to facilitate attachment of the sample to the substrate. Suitable substances that can be used to coat or functionalize the substrate include, but are not limited to, lectins, poly-lysine, antibodies, and polysaccharides.

A variety of steps can be performed to prepare or process a biological sample for and/or during an assay. Except where indicated otherwise, the preparative or processing steps described below can generally be combined in any manner and in any order to appropriately prepare or process a particular sample for and/or analysis.

(i) Tissue Sectioning

A biological sample can be harvested from a subject (e.g., via surgical biopsy, whole subject sectioning) or grown in vitro on a growth substrate or culture dish as a population of cells, and prepared for analysis as a tissue slice or tissue section. Grown samples may be sufficiently thin for analysis without further processing steps. Alternatively, grown samples, and samples obtained via biopsy or sectioning, can be prepared as thin tissue sections using a mechanical cutting apparatus such as a vibrating blade microtome. As another alternative, in some embodiments, a thin tissue section can be prepared by applying a touch imprint of a biological sample to a suitable substrate material.

The thickness of the tissue section can be a fraction of (e.g., less than 0.9, 0.8, 0.7, 0.6, 0.5, 0.4, 0.3, 0.2, or 0.1) the maximum cross-sectional dimension of a cell. However, tissue sections having a thickness that is larger than the maximum cross-section cell dimension can also be used. For example, cryostat sections can be used, which can be, e.g., 10-20 µm thick.

More generally, the thickness of a tissue section typically depends on the method used to prepare the section and the physical characteristics of the tissue, and therefore sections having a wide variety of different thicknesses can be prepared and used. For example, the thickness of the tissue section can be at least 0.1, 0.2, 0.3, 0.4, 0.5, 0.7, 1.0, 1.5, 2, 3, 4, 5, 6, 7, 8, 9, 10, 12, 13, 14, 15, 20, 30, 40, or 50 µm. Thicker sections can also be used if desired or convenient, e.g., at least 70, 80, 90, or 100 µm or more. Typically, the thickness of a tissue section is between 1-100 µm, 1-50 µm, 1-30 µm, 1-25 µm, 1-20 µm, 1-15 µm, 1-10 µm, 2-8 µm, 3-7 µm, or 4-6 µm, but as mentioned above, sections with thicknesses larger or smaller than these ranges can also be analysed.

Multiple sections can also be obtained from a single biological sample. For example, multiple tissue sections can be obtained from a surgical biopsy sample by performing serial sectioning of the biopsy sample using a sectioning blade. Spatial information among the serial sections can be preserved in this manner, and the sections can be analysed successively to obtain three-dimensional information about the biological sample.

(ii) Freezing

In some embodiments, the biological sample (e.g., a tissue section as described above) can be prepared by deep freezing at a temperature suitable to maintain or preserve the integrity (e.g., the physical characteristics) of the tissue structure. The frozen tissue sample can be sectioned, e.g., thinly sliced, onto a substrate surface using any number of suitable methods. For example, a tissue sample can be prepared using a chilled microtome (e.g., a cryostat) set at a temperature suitable to maintain both the structural integrity of the tissue sample and the chemical properties of the nucleic acids in the sample. Such a temperature can be, e.g., less than −15° C., less than −20° C., or less than −25° C.

(iii) Fixation and Postfixation

In some embodiments, the biological sample can be prepared using formalin-fixation and paraffin-embedding (FFPE), which are established methods. In some embodiments, cell suspensions and other non-tissue samples can be prepared using formalin-fixation and paraffin-embedding. Following fixation of the sample and embedding in a paraffin or resin block, the sample can be sectioned as described above. Prior to analysis, the paraffin-embedding material can be removed from the tissue section (e.g., deparaffinization) by incubating the tissue section in an appropriate solvent (e.g., xylene) followed by a rinse (e.g., 99.5% ethanol for 2 minutes, 96% ethanol for 2 minutes, and 70% ethanol for 2 minutes).

As an alternative to formalin fixation described above, a biological sample can be fixed in any of a variety of other fixatives to preserve the biological structure of the sample prior to analysis. For example, a sample can be fixed via immersion in ethanol, methanol, acetone, paraformaldehyde (PFA)-Triton, and combinations thereof.

In some embodiments, acetone fixation is used with fresh frozen samples, which can include, but are not limited to, cortex tissue, mouse olfactory bulb, human brain tumor, human post-mortem brain, and breast cancer samples. When acetone fixation is performed, pre-permeabilization steps (described below) may not be performed. Alternatively, acetone fixation can be performed in conjunction with permeabilization steps.

In some embodiments, the methods provided herein comprises one or more post-fixing (also referred to as postfixation) steps. In some embodiments, one or more post-fixing step is performed after contacting a sample with a polynucleotide disclosed herein, e.g., one or more probes such as a circular or padlock probe. In some embodiments, one or more post-fixing step is performed after a hybridization complex comprising a probe and a target is formed in a sample. In some embodiments, one or more post-fixing step is performed prior to a ligation reaction disclosed herein, such as the ligation to circularize a padlock probe.

In some embodiments, one or more post-fixing step is performed after contacting a sample with a binding or labelling agent (e.g., an antibody or antigen binding fragment thereof) for a non-nucleic acid analyte such as a protein analyte. The labelling agent can comprise a nucleic acid molecule (e.g., reporter oligonucleotide) comprising a sequence corresponding to the labelling agent and therefore corresponds to (e.g., uniquely identifies) the analyte. In some embodiments, the labelling agent can comprise a reporter oligonucleotide comprising one or more barcode sequences.

A post-fixing step may be performed using any suitable fixation reagent disclosed herein, for example, 3% (w/v) paraformaldehyde in DEPC-PBS.

(iv) Embedding

As an alternative to paraffin embedding described above, a biological sample can be embedded in any of a variety of other embedding materials to provide structural substrate to the sample prior to sectioning and other handling steps. In some cases, the embedding material can be remove, e.g., prior to analysis of tissue sections obtained from the sample. Suitable embedding materials include, but are not limited to, waxes, resins (e.g., methacrylate resins), epoxies, and agar.

In some embodiments, the biological sample can be embedded in a matrix (e.g., a hydrogel matrix). In some aspects, the embedding material can be applied to the sample one or more times. Embedding the sample in this manner typically involves contacting the biological sample with a hydrogel such that the biological sample becomes surrounded by the hydrogel. For example, the sample can be embedded by contacting the sample with a suitable polymer material, and activating the polymer material to form a hydrogel. In some embodiments, the hydrogel is formed such that the hydrogel is internalized within the biological sample.

In some embodiments, the biological sample is immobilized in the hydrogel via cross-linking of the polymer material that forms the hydrogel. Cross-linking can be performed chemically and/or photochemically, or alternatively by any other hydrogel-formation method known in the art.

The composition and application of the hydrogel-matrix to a biological sample typically depends on the nature and preparation of the biological sample (e.g., sectioned, non-sectioned, type of fixation). As one example, where the biological sample is a tissue section, the hydrogel-matrix can include a monomer solution and an ammonium persulfate (APS) initiator/tetramethylethylenediamine (TEMED) accelerator solution. As another example, where the biological sample consists of cells (e.g., cultured cells or cells disassociated from a tissue sample), the cells can be incubated with the monomer solution and APS/TEMED solutions. For cells, hydrogel-matrix gels are formed in compartments, including but not limited to devices used to culture, maintain, or transport the cells. For example, hydrogel-matrices can be formed with monomer solution plus APS/TEMED added to the compartment to a depth ranging from about 0.1 m to about 2 mm.

Additional methods and aspects of hydrogel embedding of biological samples are described for example in Chen et al., *Science* 347(6221):543-548, 2015, the entire contents of which are incorporated herein by reference.

(v) Staining

To facilitate visualization, biological samples can be stained using a wide variety of stains and staining techniques. In some embodiments, for example, a sample can be stained using any number of stains, including but not limited to, acridine orange, Bismarck brown, carmine, coomassie blue, cresyl violet, DAPI, eosin, ethidium bromide, acid fuchsine, haematoxylin, Hoechst stains, iodine, methyl green, methylene blue, neutral red, Nile blue, Nile red, osmium tetroxide, propidium iodide, rhodamine, or safranine.

The sample can be stained using hematoxylin and eosin (H&E) staining techniques, using Papanicolaou staining techniques, Masson's trichrome staining techniques, silver staining techniques, Sudan staining techniques, and/or using Periodic Acid Schiff (PAS) staining techniques. PAS staining is typically performed after formalin or acetone fixation. In some embodiments, the sample can be stained using Romanowsky stain, including Wright's stain, Jenner's stain, Can-Grunwald stain, Leishman stain, and Giemsa stain.

In some embodiments, biological samples can be destained. Methods of destaining or discoloring a biological sample are known in the art, and generally depend on the nature of the stain(s) applied to the sample. For example, in some embodiments, one or more immunofluorescent stains are applied to the sample via antibody coupling. Such stains can be removed using techniques such as cleavage of disulfide linkages via treatment with a reducing agent and detergent washing, chaotropic salt treatment, treatment with antigen retrieval solution, and treatment with an acidic glycine buffer. Methods for multiplexed staining and destaining are described, for example, in Bolognesi et al., *J. Histochem. Cytochem.* 2017; 65(8): 431-444, Lin et al., *Nat Commun.* 2015; 6:8390, Pirici et al., *J. Histochem. Cytochem.* 2009; 57:567-75, and Glass et al., *J. Histochem. Cytochem.* 2009; 57:899-905, the entire contents of each of which are incorporated herein by reference.

(vi) Isometric Expansion

In some embodiments, a biological sample embedded in a matrix (e.g., a hydrogel) can be isometrically expanded. Isometric expansion methods that can be used include hydration, a preparative step in expansion microscopy, as described in Chen et al., *Science* 347(6221):543-548, 2015.

Isometric expansion can be performed by anchoring one or more components of a biological sample to a gel, followed by gel formation, proteolysis, and swelling. In some embodiments, analytes in the sample, products of the analytes, and/or probes associated with analytes in the sample can be anchored to the matrix (e.g., hydrogel). Isometric expansion of the biological sample can occur prior to immobilization of the biological sample on a substrate, or after the biological sample is immobilized to a substrate. In some embodiments, the isometrically expanded biological sample can be removed from the substrate prior to contacting the substrate with probes disclosed herein.

In general, the steps used to perform isometric expansion of the biological sample can depend on the characteristics of the sample (e.g., thickness of tissue section, fixation, cross-linking), and/or the analyte of interest (e.g., different conditions to anchor RNA, DNA, and protein to a gel).

In some embodiments, proteins in the biological sample are anchored to a swellable gel such as a polyelectrolyte gel. An antibody can be directed to the protein before, after, or in conjunction with being anchored to the swellable gel. DNA and/or RNA in a biological sample can also be anchored to the swellable gel via a suitable linker. Examples of such linkers include, but are not limited to, 6-((Acryloyl) amino) hexanoic acid (Acryloyl-X SE) (available from ThermoFisher, Waltham, Mass.), Label-IT Amine (available from MirusBio, Madison, Wis.) and Label X (described for example in Chen et al., Nat. Methods 13:679-684, 2016, the entire contents of which are incorporated herein by reference).

Isometric expansion of the sample can increase the spatial resolution of the subsequent analysis of the sample. The increased resolution in spatial profiling can be determined by comparison of an isometrically expanded sample with a sample that has not been isometrically expanded.

In some embodiments, a biological sample is isometrically expanded to a size at least 2×, 2.1×, 2.2×, 2.3×, 2.4×, 2.5×, 2.6×, 2.7×, 2.8×, 2.9×, 3×, 3.1×, 3.2×, 3.3×, 3.4×, 3.5×, 3.6×, 3.7×, 3.8×, 3.9×, 4×, 4.1×, 4.2×, 4.3×, 4.4×, 4.5×, 4.6×, 4.7×, 4.8×, or 4.9× its non-expanded size. In some embodiments, the sample is isometrically expanded to at least 2× and less than 20× of its non-expanded size.

(vii) Crosslinking and De-Crosslinking

In some embodiments, the biological sample is reversibly or irreversibly cross-linked prior to, during, or after an assay step disclosed herein. A cross-linking agent includes a chemical agent or even light, that facilitates the attachment of one molecule to another molecule. Cross-linking agents can be protein-nucleic acid cross-linking agents, nucleic acid-nucleic acid cross-linking agents, and/or protein-protein cross-linking agents. Examples of such agents are known in the art. In some embodiments, a cross-linking agent is a reversible cross-linking agent. In some embodiments, a cross-linking agent is a non-reversible cross-linking agent.

In some examples, chromatin is cross-linked to hold chromatin-associated factor(s) in complex with chromatin DNA for analyzing the chromatin interaction event disclosed herein. In some embodiments, the sample to be analyzed is contacted with a protein-nucleic acid cross-linking agent, a nucleic acid-nucleic acid cross-linking agent, a protein-protein cross-linking agent or any combination thereof. In some embodiments, proteins and/or nucleic acids that interact with chromatin DNA become cross-linked to the chromatin DNA, such that analysis of the cross-linked proteins and/or nucleic acids can be performed in combination (e.g., in parallel or sequentially) with analysis of chromatin DNA to which they are bound. In some embodiments, primary, secondary and tertiary interactions between chromatin associated factors and chromatin DNA can be discerned. In some examples, a cross-linker is a reversible cross-linker, such that the cross-linked molecules can be easily separated. In some examples, a cross-linker is a non-reversible cross-linker, such that the cross-linked molecules cannot be easily separated. In some examples, a cross-linker is light, such as UV light. In some examples, a cross linker is light activated. These cross-linkers include formaldehyde, disuccinimidyl glutarate, UV-254, psoralens and their derivatives such as aminomethyltrioxsalen, glutaraldehyde, ethylene glycol bis [succinimidylsuccinate], and other compounds known to those skilled in the art, including those described in the Thermo Scientific Pierce Cross-linking Technical Handbook, Thermo Scientific (2009) as available on the world wide web at piercenet.com/files/1601673_Cross-link_HB_Intl.pdf.

In some aspects, the analytes, polynucleotides and/or amplification product (e.g., amplicon) of an analyte or a probe bound thereto can be anchored to a polymer matrix. For example, the polymer matrix can be a hydrogel. In some embodiments, one or more of the polynucleotide probe(s) and/or amplification product (e.g., amplicon) thereof can be modified to contain functional groups that can be used as an anchoring site to attach the polynucleotide probes and/or amplification product to a polymer matrix.

In some embodiments, the biological sample is immobilized in a hydrogel via cross-linking of the polymer material that forms the hydrogel. Cross-linking can be performed chemically and/or photochemically, or alternatively by any other hydrogel-formation method known in the art. A hydrogel may include a macromolecular polymer gel including a network. Within the network, some polymer chains can optionally be cross-linked, although cross-linking does not always occur.

In some embodiments, a hydrogel can include hydrogel subunits, such as, but not limited to, acrylamide, bis-acrylamide, polyacrylamide and derivatives thereof, poly(ethylene glycol) and derivatives thereof (e.g. PEG-acrylate (PEG-DA), PEG-RGD), gelatin-methacryloyl (GelMA), methacrylated hyaluronic acid (MeHA), polyaliphatic polyurethanes, polyether polyurethanes, polyester polyurethanes, polyethylene copolymers, polyamides, polyvinyl alcohols, polypropylene glycol, polytetramethylene oxide, polyvinyl pyrrolidone, polyacrylamide, poly(hydroxyethyl acrylate), and poly(hydroxyethyl methacrylate), collagen, hyaluronic acid, chitosan, dextran, agarose, gelatin, alginate, protein polymers, methylcellulose, and the like, and combinations thereof.

In some embodiments, a hydrogel includes a hybrid material, e.g., the hydrogel material includes elements of both synthetic and natural polymers. Examples of suitable hydrogels are described, for example, in U.S. Pat. Nos. 6,391,937, 9,512,422, and 9,889,422, and in U.S. Patent Application Publication Nos. 2017/0253918, 2018/0052081 and 2010/0055733, the entire contents of each of which are incorporated herein by reference.

In some embodiments, the hydrogel can form the substrate. In some embodiments, the substrate includes a hydrogel and one or more second materials. In some embodiments, the hydrogel is placed on top of one or more second materials. For example, the hydrogel can be pre-formed and then placed on top of, underneath, or in any other configuration with one or more second materials. In some embodiments, hydrogel formation occurs after contacting one or more second materials during formation of the substrate. Hydrogel formation can also occur within a structure (e.g., wells, ridges, projections, and/or markings) located on a substrate.

In some embodiments, hydrogel formation on a substrate occurs before, contemporaneously with, or after probes are provided to the sample. For example, hydrogel formation can be performed on the substrate already containing the probes.

In some embodiments, hydrogel formation occurs within a biological sample. In some embodiments, a biological sample (e.g., tissue section) is embedded in a hydrogel. In some embodiments, hydrogel subunits are infused into the biological sample, and polymerization of the hydrogel is initiated by an external or internal stimulus.

In embodiments in which a hydrogel is formed within a biological sample, functionalization chemistry can be used. In some embodiments, functionalization chemistry includes hydrogel-tissue chemistry (HTC). Any hydrogel-tissue backbone (e.g., synthetic or native) suitable for HTC can be used for anchoring biological macromolecules and modulating functionalization. Non-limiting examples of methods using HTC backbone variants include CLARITY, PACT, ExM, SWITCH and ePACT. In some embodiments, hydrogel formation within a biological sample is permanent. For example, biological macromolecules can permanently adhere to the hydrogel allowing multiple rounds of interrogation. In some embodiments, hydrogel formation within a biological sample is reversible.

In some embodiments, additional reagents are added to the hydrogel subunits before, contemporaneously with, and/or after polymerization. For example, additional reagents can include but are not limited to oligonucleotides (e.g., probes), endonucleases to fragment DNA, fragmentation buffer for DNA, DNA polymerase enzymes, dNTPs used to amplify the nucleic acid and to attach the barcode to the amplified fragments. Other enzymes can be used, including without limitation, RNA polymerase, transposase, ligase, proteinase K, and DNAse. Additional reagents can also include reverse transcriptase enzymes, including enzymes with terminal transferase activity, primers, and switch oligonucleotides. In some embodiments, optical labels are added to the hydrogel subunits before, contemporaneously with, and/or after polymerization.

In some embodiments, HTC reagents are added to the hydrogel before, contemporaneously with, and/or after polymerization. In some embodiments, a cell labelling agent is added to the hydrogel before, contemporaneously with, and/or after polymerization. In some embodiments, a cell-penetrating agent is added to the hydrogel before, contemporaneously with, and/or after polymerization.

Hydrogels embedded within biological samples can be cleared using any suitable method. For example, electrophoretic tissue clearing methods can be used to remove biological macromolecules from the hydrogel-embedded sample. In some embodiments, a hydrogel-embedded sample is stored before or after clearing of hydrogel, in a medium (e.g., a mounting medium, methylcellulose, or other semi-solid mediums).

In some embodiments, a method disclosed herein comprises de-crosslinking the reversibly cross-linked biological sample. The de-crosslinking does not need to be complete. In some embodiments, only a portion of crosslinked molecules in the reversibly cross-linked biological sample are de-crosslinked and allowed to migrate.

(viii) Tissue Permeabilization and Treatment

In some embodiments, a biological sample can be permeabilized to facilitate transfer of analytes out of the sample, and/or to facilitate transfer of species (such as probes) into the sample. If a sample is not permeabilized sufficiently, the amount of analyte captured from the sample may be too low to enable adequate analysis. Conversely, if the tissue sample is too permeable, the relative spatial relationship of the analytes within the tissue sample can be lost. Hence, a balance between permeabilizing the tissue sample enough to obtain good signal intensity while still maintaining the spatial resolution of the analyte distribution in the sample is desirable.

In general, a biological sample can be permeabilized by exposing the sample to one or more permeabilizing agents. Suitable agents for this purpose include, but are not limited to, organic solvents (e.g., acetone, ethanol, and methanol), cross-linking agents (e.g., paraformaldehyde), detergents (e.g., saponin, Triton X-100™ or Tween-20™), and enzymes (e.g., trypsin, proteases). In some embodiments, the biological sample can be incubated with a cellular permeabilizing agent to facilitate permeabilization of the sample. Additional methods for sample permeabilization are described, for example, in Jamur et al., Method Mol. Biol. 588:63-66, 2010, the entire contents of which are incorporated herein by reference. Any suitable method for sample permeabilization can generally be used in connection with the samples described herein.

In some embodiments, the biological sample can be permeabilized by adding one or more lysis reagents to the sample. Examples of suitable lysis agents include, but are not limited to, bioactive reagents such as lysis enzymes that are used for lysis of different cell types, e.g., gram positive or negative bacteria, plants, yeast, mammalian, such as lysozymes, achromopeptidase, lysostaphin, labiase, kitalase, lyticase, and a variety of other commercially available lysis enzymes.

Other lysis agents can additionally or alternatively be added to the biological sample to facilitate permeabilization. For example, surfactant-based lysis solutions can be used to lyse sample cells. Lysis solutions can include ionic surfactants such as, for example, sarcosyl and sodium dodecyl sulfate (SDS). More generally, chemical lysis agents can include, without limitation, organic solvents, chelating agents, detergents, surfactants, and chaotropic agents.

In some embodiments, the biological sample can be permeabilized by non-chemical permeabilization methods. Non-chemical permeabilization methods are known in the art. For example, non-chemical permeabilization methods that can be used include, but are not limited to, physical lysis techniques such as electroporation, mechanical permeabilization methods (e.g., bead beating using a homogenizer and grinding balls to mechanically disrupt sample tissue structures), acoustic permeabilization (e.g., sonication), and thermal lysis techniques such as heating to induce thermal permeabilization of the sample.

Additional reagents can be added to a biological sample to perform various functions prior to analysis of the sample. In some embodiments, DNase and RNase inactivating agents or inhibitors such as proteinase K, and/or chelating agents such as EDTA, can be added to the sample. For example, a method disclosed herein may comprise a step for increasing accessibility of a nucleic acid for binding, e.g., a denaturation step to opening up DNA in a cell for hybridization by a probe. For example, proteinase K treatment may be used to free up DNA with proteins bound thereto.

B. Analytes

The methods and compositions disclosed herein can be used to detect and analyze a wide variety of different analytes involved in chromatin interaction. A target or analyte can be directly or indirectly detected.

Analytes can be derived from a specific type of cell and/or a specific subcellular region, e.g., from cell nuclei or from mitochondria. Permeabilizing agents that specifically target certain cell compartments and organelles can be used to selectively release analytes from cells for analysis, and/or allow access of one or more reagents (e.g., probes for analyte detection) to the analytes in the cell or cell compartment or organelle.

The analyte may include any biomolecule, macromolecule, or chemical compound, including a protein or peptide, a lipid or a nucleic acid molecule, or a small molecule, including organic or inorganic molecules, that may be involved in chromatin interaction. An analyte can be any substance or entity for which a specific binding partner (e.g., an affinity binding partner) can be developed. Such a specific binding partner may be a nucleic acid probe (for a nucleic acid analyte) and may lead directly to the generation of a RCA template (e.g. a padlock or other circularizable probe). Alternatively, the specific binding partner may be coupled to a nucleic acid, which may be detected using an RCA strategy, e.g. in an assay which uses or generates a circular nucleic acid molecule which can be the RCA template.

Analytes of particular interest may include nucleic acid molecules, such as DNA (e.g. genomic DNA, mitochondrial DNA, plastid DNA, viral DNA, etc.) and RNA (e.g. mRNA, microRNA, rRNA, snRNA, viral RNA, etc.), and synthetic and/or modified nucleic acid molecules, (e.g. including nucleic acid domains comprising or consisting of synthetic or modified nucleotides such as LNA, PNA, morpholino, etc.), proteinaceous molecules such as peptides, polypeptides, proteins or prions or any molecule which includes a protein or polypeptide component, etc., or fragments thereof, or a lipid or carbohydrate molecule, or any molecule which comprise a lipid or carbohydrate component. The analyte may be a single molecule or a complex that contains two or more molecular subunits, e.g. including but not limited to protein-DNA complexes, which may or may not be covalently bound to one another, and which may be the same or different. Thus in addition to cells or microorganisms, such a complex analyte may also be a protein complex or protein interaction. Such a complex or interaction may thus be a homo- or hetero-multimer. Aggregates of molecules, e.g. proteins may also be target analytes, for example aggregates of the same protein or different proteins. The analyte may also be a complex between proteins or peptides and nucleic acid molecules such as DNA or RNA, e.g., interactions between proteins and nucleic acids, e.g. chromatin associated factors, regulatory factors, such as transcription factors, and DNA or RNA.

Methods and compositions disclosed herein can be used to analyze any number of analytes. For example, the number of analytes that are analyzed can be at least about 2, at least about 3, at least about 4, at least about 5, at least about 6, at least about 7, at least about 8, at least about 9, at least about 10, at least about 11, at least about 12, at least about 13, at least about 14, at least about 15, at least about 20, at least about 25, at least about 30, at least about 40, at least about 50, at least about 100, at least about 1,000, at least about 10,000, at least about 100,000 or more different analytes present in a region of the sample or within an individual feature of the substrate.

In any embodiment described herein, the analyte comprises a target sequence. In some embodiments, the target sequence may be endogenous to the sample, e.g., associated with or in the chromatin of a cell. A biological sample may comprise one or a plurality of analytes of interest, e.g., a plurality of chromatin interaction events each involving two or more chromatin regions in the same molecule or in different molecules. Methods for performing multiplexed assays to analyze two or more different chromatin interaction events in cells in a single biological sample are provided.

II. ANALYSIS OF CHROMATIN INTERACTIONS

In eukaryotic genomes, chromosomal DNA winds itself around histone proteins (i.e., "nucleosomes"), thereby forming a complex known as chromatin. The tight or loose packaging of chromatin contributes to the control of gene expression. Tightly packed chromatin ("closed chromatin") is usually not permissive for gene expression while more loosely packaged, accessible regions of chromatin ("open chromatin") is associated with the active transcription of gene products. Methods for probing genome—wide DNA accessibility have proven extremely effective in identifying regulatory elements across a variety of cell types and quantifying changes that lead to both activation or repression of gene expression. Exemplary genome architecture mapping techniques are described in U.S. Pat. No. 10,526,639 B2, which is incorporated by reference in its entirety.

The initiation of gene transcription in eukaryotes begins when RNA polymerase along with general transcription factors bind to a promoter region to form a preinitiation complex (closed complex). Transition of the complex from a closed to an open state results in separation of the two DNA strands and presentation of the template strand to the active site of the RNA polymerase. Promoters are regions usually in the immediate vicinity of the transcription start site (TSS) that bind and position the preinitiation complex. The TATA box binding protein (TBP) binds to the highly conserved TATA box to initiate transcription complex assembly. Eukaryotic genes also contain other regulatory sequences called cis-acting control elements which bind transcriptional activators or repressors to increase or decrease transcription from the core promoter. These regulatory elements include enhancers, silencers, and insulators. In many cases regulatory elements can be located at distances up to several megabases from their target genes. Evidence shows that long-range control of gene expression can be mediated through direct physical interactions between genes and these regulatory elements. Transcription factors are a group of proteins involved in transcription initiation and regulation that bind specific sequence elements of the promoter and recruit RNA polymerase to the transcriptional start site. Examples of these factors for RNA polymerase II include TFIID, TFIIA, TFIIB, TFIIF, TFIIE, and TFIIH. Orphanides, G., Lagrange, T., Reinberg, D. (1996). The general transcription factors of RNA polymerase II, Genes & Development, 10(21): 2657-83. doi:10.1101/gad.10.21.2657. Enhancers are relatively short regions of DNA that can be bound by transcription factors to affect gene transcription. There are hundreds of thousands of enhancers in the human genome and they are found in both prokaryotes and eukaryotes. Pennacchio, L. A, Bickmore, W., Dean, A., Nobrega, M. A., Bejerano, G. (2013). Enhancers: five essential questions, Nature Reviews. Genetics, 14(4): 288-95. doi:10.1038/nrg3458; Kulaeva O. I., Nizovtseva, E. V., Polikanov, Y. S., Ulianov, S. V., Studitsky, V. M. (2012). Distant activation of transcription: mechanisms of enhancer action, Molecular and Cellular Biology, 32(24): 4892-7. doi:10.1128/MCB.01127-12. Silencers are DNA sequences that bind transcription regulation factors called repressors which prevents RNA polymerase from transcribing the DNA sequence into RNA. The most common position is found upstream of the target gene. Maston, G., Sarah, E., Michael, G., (2006). Transcriptional regulatory elements in the Human Genome, Annual Review of Genomics and Human Genetics, 7: 29-59. doi:10.1146/annurev.genom.7.080505.115623.

In one aspect, disclosed herein is a method of analyzing a biological sample, comprising: a) obtaining a biological sample; b) hybridizing a first set of probes (e.g., one or more probes that hybridize to a nucleic acid strand in a chromatin region) comprising at least two unique oligonucleotide sequences to a sense or antisense strand (e.g., a first or second nucleic acid strand) of at least two primary target nucleic acid sequences, wherein said at least two primary target nucleic acid sequences are engaged in a chromatin interaction event; c) hybridizing a second set of probes (e.g., one or more probes that hybridize to a nucleic acid strand in a chromatin region) comprising at least two unique oligonucleotide sequences to a sense or antisense strand (e.g., a first or second nucleic acid strand) of said at least two primary target nucleic acid sequences; d) hybridizing a third set of probes (e.g., one or more bridging probes or circularizing probes) to said second probe set, wherein said second probes (e.g., one or more probes that hybridize to a nucleic acid strand in a chromatin region) are spatially proximate to one another due to being hybridized to at least two primary target nucleic acid sequences engaged in a chromatin interaction event and wherein said third probes (e.g., one or more bridging probes or circularizing probes) bridge the ends of said second probes; e) extending the third set of probes (e.g., one or more bridging probes or circularizing probes) with a polymerase to form a circularized nucleic acid comprising at least a portion of the at least two primary target nucleic acid sequences engaged in a chromatin interaction event; f) amplifying said circular nucleic acid to generate a population of amplicons comprising signal producing tags detectable in situ; and g) detecting said population of tagged amplicons in situ by said signal producing tags.

In some embodiments, a method described herein is exemplified in FIG. 1. The sample can be fixed or not fixed, e.g., a formalin-fixed, paraffin-embedded (FFPE) sample, a frozen tissue sample, or a fresh tissue sample. As shown in FIG. 1, a sample may be a sample on a substrate (e.g., a tissue on a slide). Samples and sample preparation techniques amenable to the methods provided herein are outlined in Section I.A. In some embodiments, the subcellular structure and chromatin confirmation of a sample is perservered during sample preparation (e.g., by crosslinking). In some embodiments, chromatin interaction events involving a first and second chromatin region are analyzed by the provided methods. In some embodiments, an amplification product is generated (e.g., by generating a rolling circle amplification (RCA) product of the circular probe) and detected using detected labeled probes. In some embodiments, the sample is analyzed to detect a plurality of chromatin interaction events, e.g., in parallel or sequentially, in situ.

As used herein, the term "sample," generally refers to a biological sample of a subject. The biological sample may comprise any number of macromolecules, for example, cellular macromolecules. The sample may be a cell sample. The sample may be a cell line or cell culture sample. The sample can include one or more cells. The sample can include one or more microbes. The biological sample may be a nucleic acid sample or protein sample. The biological sample may also be a carbohydrate sample or a lipid sample. The biological sample may be derived from another sample. The sample may be a tissue sample, such as a biopsy, core biopsy, needle aspirate, or fine needle aspirate. The sample may be a fluid sample, such as a blood sample, urine sample, or saliva sample. The sample may be a skin sample. The sample may be a cheek swab. The sample may be a plasma or serum sample. The sample may be a cell-free or cell free sample. A cell-free sample may include extracellular polynucleotides. Extracellular polynucleotides may be isolated from a bodily sample that may be selected from the group consisting of blood, plasma, serum, urine, saliva, mucosal excretions, sputum, stool and tears.

As used herein, the term "genome," generally refers to genomic information from a subject, which may be, for example, at least a portion or an entirety of a subject's hereditary information. A genome can be encoded either in DNA or in RNA. A genome can comprise coding regions (e.g., that code for proteins) as well as non-coding regions. A genome can include the sequence of all chromosomes together in an organism. For example, the human genome ordinarily has a total of 46 chromosomes. The sequence of all of these together may constitute a human genome.

As used herein, the term "chromatin interaction event(s)," generally refers to long-range interactions between different chromatin sites, thereby forming a high-level conformation of chromatin to maintain chromatin structure or to promote gene expression.

As used herein, the term "transcriptional regulatory region," or regulatory region, generally refers to a region within the genomic DNA that is located upstream or downstream of the gene, for example, 10 kb-1 Mb, 50 kb-500 kb, 100 kb-200 kb, including promoters, enhancers. A region of a site where a trans-acting factor (e.g., a transcription factor) binds.

As used herein, the term "binding motif," generally refers to an element which is present on genomic DNA and which can be bound by a trans-acting factor such as a transcription factor to regulate a target gene, for example, to regulate expression of an effector gene in the present invention.

As used herein, the term "chromatin interaction frequency," also referred to herein as "Hi-C interaction frequency" or Hi-C contact frequency, generally refers to the different regions found in chromatin interactions when performing chromatin conformational analysis. The signal of the interaction is expressed as the number of reads in the Hi-C data where the two ends fall within a specific area.

As used herein, the term "chromatin open region sequence" generally refers to a DNA sequence that is exposed in chromatin due to nucleosome binding or the like and can be bound by a trans-acting factor such as a transcription factor.

As used herein, the term "chromosome conformation capture" or "chromatin conformation capture technology" generally refers to all techniques used to analyze spatial organization of chromatin in a cell. Such techniques enable the relationship between different spatial positions of chromatin to establish chromatin three-dimensional structure information which also includes high-throughput sequencing chromatin conformation capture technology. Such interactions may result from biological functions, including but not limited to promoter-enhancer interactions. Examples of suitable chromosome conformation capture technology processes include but are not limited to 3C and Hi-C. These processes have been described in the following publications: Dekker, J., et al. (2002). Capturing chromosome conformation, Science, 295, 1306-1311; Belton, J., et al. (2012). Hi-C: A comprehensive technique to capture the conformation of genomes, *Methods,* 58, 3. Additional methods of shearing and tagging chromatin DNA using transposases are described in US 2016/0208323 A1, which is incorporated by reference in its entirety.

As used herein, the term "high-throughput chromatin conformation capture technology" generally refers to the combination of high-throughput sequencing technology and bioinformatics analysis methods to efficiently analyze the spatial position of the entire chromatin DNA in the genome-wide range and achieve high resolution. A method for chromatin three-dimensional structure and chromatin interaction information. The technique includes at least Hi-C, Hi-C based improved technology in situ Hi-C, and BL-Hi-C obtained after further introduction of bridge-linker based on the in situ Hi-C method. In addition, the ChIA-PET method is also a high-throughput chromatin conformation capture technique.

In some embodiments, available techniques can be used to confirm the data generated through the methods described herein. For example, as used herein, the term "Assay for Transposase Accessible Chromatin with high-throughput sequencing" or "ATAC-seq" generally refers to a technique for studying chromatin accessibility in molecular biology. It consists of two parts, the ATAC experiment and high-throughput sequencing. The ATAC-seq method probes DNA accessibility with an artificial transposon, which inserts specific sequences into accessible regions of chromatin. Because the transposase can only insert sequences into accessible regions of chromatin not bound by transcription factors and/or nucleosomes, sequencing reads can be used to infer regions of increased chromatin accessibility. Therefore, the enrichment of certain locus sequences in the genome indicates that there are no nucleosomes in the region and is in a loosely exposed state in which nuclear machinery such as DNA-binding proteins can enter, providing information on the transcriptional active state of the chromatin segment.

In some embodiments, target nucleic acid sequences engaged in chromatin interaction events will be sequenced. In one embodiment, amplification products ("amplicons") comprising all or part of the nucleic acid sequences engaged in chromatin interaction events will be sequenced. As used herein, the term "sequencing," generally refers to methods and technologies for determining the sequence of nucleotide bases in one or more polynucleotides. The polynucleotides can be, for example, nucleic acid molecules such as deoxyribonucleic acid (DNA) or ribonucleic acid (RNA), including variants or derivatives thereof (e.g., single stranded DNA). Sequencing can be performed by various systems currently available, such as, without limitation, a sequencing system by Illumina®, Pacific Biosciences (PacBio®), Oxford Nanopore®, or Life Technologies (Ion Torrent®). Alternatively, or in addition, sequencing may be performed using nucleic acid amplification, polymerase chain reaction (PCR) (e.g., digital PCR, quantitative PCR, or real time PCR), or isothermal amplification. Such systems may provide a plurality of raw genetic data corresponding to the genetic information of a subject (e.g., human), as generated by the systems from a sample provided by the subject. In some examples, such systems provide sequencing reads (also "reads" herein). A read may include a string of nucleic acid bases corresponding to a sequence of a nucleic acid molecule that has been sequenced. In some situations, systems and methods provided herein may be used with proteomic information. Other sequencing methods known in the art, such as sequencing by extension with reversible terminators, in situ sequencing, fluorescent in situ sequencing (FISSEQ), pyrosequencing, massively parallel signature sequencing (MPSS) and the like are suitable for use in the methods of the invention. Reversible termination methods use step-wise sequencing-by-synthesis biochemistry that coupled with reversible termination and removable fluorescence.

In situ sequencing techniques are described in Ke, R. et al., (2013). In situ sequencing for RNA analysis in preserved tissue and cells, *Nat. Methods*, 10, 857-860.

FISSEQ is a method whereby DNA is extended by adding a single type of fluorescently-labelled nucleotide triphosphate to the reaction; washing away unincorporated nucleotide, detecting incorporation of the nucleotide by measuring fluorescence, and repeating the cycle. At each cycle, the fluorescence from previous cycles is bleached or digitally subtracted or the fluorophore is cleaved from the nucleotide and washed away. FISSEQ is described, for example in, (Lee et al. (2014). *Science.* 343, 1360-3.)

Pyrosequencing is a method in which the pyrophosphate (PPi) released during each nucleotide incorporation event (i.e., when a nucleotide is added to a growing polynucleotide sequence). The PPi released in the DNA polymerase-catalyzed reaction is detected by ATP sulfurylase and luciferase in a coupled reaction which can be visibly detected. The added nucleotides are continuously degraded by a nucleotide-degrading enzyme. After the first added nucleotide has been degraded, the next nucleotide can be added. As this procedure is repeated, longer stretches of the template sequence are deduced. Pyrosequencing is described further in Ronaghi et al. (1998) *Science* 281, 363.

MPSS utilizes ligation-based DNA sequencing simultaneously. A mixture of labelled adaptors comprising all possible overhangs is annealed to a target sequence of four nucleotides. The label is detected upon successful ligation of an adaptor. A restriction enzyme is then used to cleave the DNA template to expose the next four bases. MPSS is described further in Brenner et al. (2000) *Nat. Biotech.* 18, 630.

In one embodiment, the biological sample can be labeled or tagged with a detectable label or signal producing tag. Typically, the label or tag will bind chemically (e.g., covalently, hydrogen bonding or ionic bonding) to the sample, or a component thereof. The detectable label can be selective for a specific target (e.g., a biomarker or class of molecule), as can be accomplished with an antibody or other target specific binder. The detectable label can comprise a visible component, as is typical of a dye or fluorescent molecule (e.g., fluorophore); however, any signaling means used by the label is also contemplated. A fluorescently labeled biological sample, for example, is a biological sample labeled through techniques such as, but not limited to, immunofluorescence, immunohistochemical or immunocytochemical staining to assist in microscopic analysis, for example, fluorescence microscopy. Examples, of suitable fluorescence microscopy techniques are described in Sanderson, M. J. et al. (2014). Fluorescence Microscopy, *Cold Spring Harbor Protocols*, 2014(10), doi:10.1101/pdb.top071795. Thus, the detectable label can be chemically attached to the biological sample, or a targeted component thereof. The detectable label can be an antibody and/or fluorescent dye wherein the antibody and/or fluorescent dye, further comprises a physical, biological, or chemical anchor or moiety that attaches or crosslinks the sample to the composition, hydrogel or other swellable material. The detectable label can be attached to the nucleic acid adaptor. The labeled sample may furthermore include more than one label. For example, each label can have a specific or distinguishable fluorescent property, e.g., distinguishable excitation and emission wavelengths. Further, each label can have a different target specific binder that is selective for a specific and distinguishable target in, or component of the sample.

As used herein, the term "oligonucleotide," generally refers to a molecule comprised of two or more deoxyribonucleotides or ribonucleotides. The exact size will depend on many factors, which in turn depends on the ultimate function or use of the oligonucleotide. The oligonucleotide may be generated in any manner, including chemical synthesis, DNA replication, reverse transcription, or a combination thereof.

The term "primer" refers to an oligonucleotide that can act as a point of initiation of synthesis when placed under conditions in which primer extension is initiated. An oligonucleotide "primer" may occur naturally, as in a purified restriction digest or may be produced synthetically. A primer is selected to have on its 3' end a region that is "substantially" complementary to a strand of specific sequence of the template. A primer must be sufficiently complementary to hybridize with a template strand for primer elongation to occur. A primer sequence need not reflect the exact sequence of the template. For example, a non-complementary nucleotide fragment may be attached to the 5' end of the primer, with the remainder of the primer sequence being substantially complementary to the strand. Non-complementary bases or longer sequences can be interspersed into the primer, provided that the primer sequence has sufficient complementarity with the sequence of the template to hybridize and thereby form a template primer complex for synthesis of the extension product of the primer.

In eukaryotic genomes, chromosomal DNA winds itself around histone proteins (i.e., nucleosomes"), thereby forming a complex known as chromatin. The tight or loose packaging of chromatin contributes to the control of gene expression. Tightly packed chromatin ("closed chromatin") is usually not permissive for gene expression while more loosely packaged, accessible regions of chromatin ("open chromatin") is associated with the active transcription of gene products. Methods for probing genome—wide DNA accessibility have proven extremely effective in identifying regulatory elements across a variety of cell types and quantifying changes that lead to both activation or repression of gene expression.

The present invention finds use in diagnostic applications. For example, in some embodiments, the methods described herein are used to determine the status of chromosome conformation of a gene of interest and identify/characterize cis- and trans chromatin interactions it is involved in. Certain disease states are characterized by aberrant (e.g., increased or decreased) gene expression that correlates at some states of development or in some cell types with distinct pattern of chromatin interactions. The methods thus find use in the diagnosis of such disease states by detecting these patterns of chromatin interaction events. In some embodiments, the methods are used to compare the interaction profiles of genes in the activated or inactivated states with test samples in order to determine the activation status of a gene.

In still other embodiments, the methods described herein can be used in the detection of variant (e.g., polymorphic) genes that have altered expression. For example, in some genes the presence of certain single nucleotide polymorphisms (SNPs) are associated with disease states or altered gene function (e.g., drug metabolism). In some embodiments, the disclosed methods are used to compare the interaction profile of known SNPs with test samples in order to determine the chromatin interactions of the variant gene, which can in some case be correlated with the activation status of a gene at some stage of development or in some cell types.

In yet other embodiments, the methods described herein can be used to detect patterns of chromatin interactions that are indicative of genomic rearrangements including, but not limited to, translocation, deletion, fusion, and inversion. In some embodiments, the present invention is used to compare the interaction profile of known gene rearrangements with test samples in order to determine the chromatin interactions of the variant gene, which can in some case be correlated with the activation status of a gene at some stage of development or in some cell types. In some embodiments, interaction profiles to be used as controls are experimentally generated using, for example, the methods of the present invention.

In additional embodiments, diagnostic signatures can be utilized. In some embodiments, diagnostic signatures give information about diagnostic predisposition and prognosis regarding specific diseases. For example, in some embodiments, diagnostic signatures predict future genomic rearrangements or detect chromosome conformation features (e.g., looping or trans-interactions) associated with specific disease states or prognosis. In some embodiments, diagnostic signatures to be used as controls (e.g., indicative of a given disease state or prognosis) are experimentally generated using, for example, the methods of the present invention.

In yet other embodiments, the methods of the present invention find use in research applications. Such applications include, but are not limited to, the study of gene regulation in development and differentiation, the study of gene regulation in disease, the study of gene regulation in drug metabolism, and the study of regulation of variant genes. In some embodiments, research applications utilize samples from human subjects. In other embodiments, research applications utilize test samples from non-human animals (e.g., non-human mammals). In some embodiments, the non-human animals are transgenic animals.

A biological sample may be any physical entity comprising DNA that is or is capable of being cross-linked. However, in some embodiments the methods do not use cross-linking. The sample may be or may be derived from biological material. The sample may be or may be derived from one or more cells, one or more nuclei, or one or more tissue samples. The entities may be or may be derivable from any entities in which DNA—such as chromatin—is present. The sample may be or may be derived from one or more isolated cells or one or more isolated tissue samples, or one or more isolated nuclei. The sample may be or may be derived from living cells and/or dead cells and/or nuclear lysates and/or isolated chromatin. The sample may be derived from a subject that is to be tested for the likelihood that they will suffer from a disease in the future. The sample may be derived from viable or non-viable patient material.

Cells can be derived from cell culture or analyzed ex vivo from a specific tissue from a living organism or a dead organism, i.e., post-mortem, or from a whole experimental organism (e.g., a whole *D. melanogaster* embryo or *C. elegans* embryo), or from a mixture of microorganisms. Cells used in the analysis can be selected, e.g., by synchronizing the cells in a particular stage of the cell cycle, or sorting the cells e.g. by fluorescence activated cell sorting to capture a cell type expressing a specific marker, e.g., using an antibody specific for a protein uniquely expressed in the cell type or cell stage of interest, or detected by in situ hybridization e.g. with a nucleic acid probe that detects a specific e.g. mRNA, or other RNA, expressed specifically in the cell type of interest, or a fluorescent marker such as GFP showing expression of a specific gene or characteristic of a specific stage. For example, a GFP transgene under the control of the promoter of the Pitx3 transcription factor can be used to mark dopamine-expressing neurons (Maxwell S., et al. (2005). Pitx3 regulates tyrosine hydroxylase expression in the substantia nigra and identifies a subgroup of mesencephalic dopaminergic progenitor neurons during mouse development. *Dev. Biol.* 282(2): 467-479). Cells can be pre-treated with an agent, e.g., to test the effect of drugs on co-segregation or positioning of loci or be studied during the lifetime of an organism to understand development, ageing and degeneration.

Optionally, a suspension of single cells is prepared depending on the species and type of tissue, e.g., a single cell suspension of mammalian solid tissues may be prepared. Preparation of a single cell suspension may be carried out by any procedure that is also compatible with 3C-techonologies. Detailed description of several single cell preparations compatible with the production of a chromatin sample that preserves crosslinked chromatin contacts can be found in e.g. Hagege, H. et al. (2007). Quantitative analysis of chromosome conformation capture assays (3C-qPCR), *Nature Protocols,* 2: 1722. In the case of multicellular organisms, the preparation of a single cell suspension may start by tissue dissection, followed by treatment with collagenase, or, for soft tissues (e.g. mouse thymus or fetal liver), by passage of tissue through a cell strainer (e.g. 40 micrometer mesh), or in the case of cells grown in in vitro culture or microorganism cultures, through centrifugation of the culture at appropriate force for the cell type, followed by resuspension at appropriate strength to yield a single cell suspension with minimal cell damage or death. Application to post-mortem samples is also possible using published protocols or developments thereafter (Mitchell, A. C. et al. (2014). The genome in three dimensions: a new frontier in human brain disease. *Biol. Psychiatry,* 75: 961). Methods to produce chromatin containing crosslinked DNA fragments that reflect chromatin contacts has also been possible using plant materials (Grab, S. et al. (2013). Characterization of chromosomal architecture in *Arabidopsis* by chromosome conformation capture. *Genome Biology,* 14: R129) and insect tissues (Ghavi-Helm, Y. et al. (2014). Enhancer loops appear stable during development and are associated with paused polymerase, *Nature,* 512: 96).

In some embodiments, nuclei, cells, tissues or whole organisms can be treated with a crosslinking agent, e.g. a chemical crosslinking agent. In some embodiments, the biological can be treated with a crosslinking agent prior to hybridizing probes to the biological sample. The crosslinking agent induces linkage of proteins with each other and between nucleic acids (DNA and/or RNA) and proteins. The method of the invention is compatible with cross-linking conditions that are also compatible with current 3C-based methods. In one embodiment, the cross-linking agent is formaldehyde. For example, formaldehyde can be used at a concentration of 0.5-4% or about 1%-2% (all w/w) in a buffered solution, e.g., of PBS pH 7.0-8.0, or directly by addition of concentrated solution of the cross-linking agent directly to cell medium for 5-120 min or, in one embodiment, between about 10-20 min. Cross-linking agents other than formaldehyde can also be used in accordance with the present invention, such as UV light, mitomycin C, nitrogen mustard, melphalan, 1,3-butadiene diepoxide, cis diaminedichloroplatinum (II) and cyclophosphamide, disuccinimidylglutarate, dithiobis-succinimidyl propionate, and glutaraldehyde.

In another embodiment, the method is also possible without a cross-linking step. For example, cryomilling of vitrified cells may be used (Oeffinger, M. et al. (2007). Comprehensive analysis of diverse ribonucleoprotein complexes, *Nature Methods,* 4: 951-6; Hakhverdyan, et al. (2015). Rapid, optimized interatomic screening, *Nature Methods,* 12: 553). In an alternative embodiment, protocols such as CUT&RUN are suitable which have been used successfully to profile insoluble chromatin and detect long-range 3D contacts without cross-linking. Skene, P. J., Henikoff, J. G., Henikoff, S. (2018). Targeted in Situ Genome—Wide Profiling With High Efficiency for Low Cell Number, *Nature Protocols,* 13(5), 1006-1019, doi: 10.1038/nprot.2018.015.

In some embodiments, a sample to be assayed can be placed on a substrate or an array, which is an arrangement of molecules, such as biological macromolecules (such as peptides or nucleic acid molecules) or biological samples (such as tissue sections), in addressable locations on or in a substrate. Tissues in a tissue section (such as a paraffin, fixed, unfixed, frozen section, including a FFPE section) on a microscope slide.

Within an array, each arrayed sample is addressable, in that its location can be reliably and consistently determined within at least two dimensions of the array. The feature application location on an array can assume different shapes. For example, the array can be regular (such as arranged in uniform rows and columns) or irregular. Thus, in ordered arrays the location of each sample is assigned to the sample at the time when it is applied to the array, and a key may be provided in order to correlate each location with the appropriate target or feature position. Often, ordered arrays are arranged in a symmetrical grid pattern, but samples could be arranged in other patterns (such as in radially distributed lines, spiral lines, or ordered clusters). Addressable arrays may be computer readable, in that a computer can be programmed to correlate an address on the array with information about the sample at that position (such as hybridization or binding data, including for instance signal intensity). In some examples of computer readable formats, the individual features in the array are arranged regularly, for instance in a Cartesian grid pattern, which can be correlated to address information by a computer.

Tissue arrays, also called tissue microarrays or TMAs, include a plurality of sections of normal and/or diseased tissue (such as cancerous tissue with or without associated normal adjacent tissue) on a single microscope slide. For example, a tissue microarray allows for the analysis of expression of one or more markers on a large number of tumors in a single experiment.

In some embodiments, a chromatin is genomic chromatin. In exemplary embodiments, a chromatin is genomic chromatin of a eukaryotic cell. Primary functions of genomic chromatin of a eukaryotic cell may be DNA packaging into a smaller volume to fit in the cell, strengthening of the DNA to allow mitosis, prevent DNA damage, and to control gene expression and DNA replication. The structure of chromatin depends on several factors. The overall structure depends on the stage of the cell cycle: during interphase the chromatin is structurally loose to allow access to RNA and DNA polymerases that transcribe and replicate the DNA. The local structure of chromatin during interphase depends on the genes present on the DNA: DNA coding genes that are actively transcribed are more loosely packaged and are found associated with RNA polymerases (referred to as euchromatin) while DNA coding inactive genes are found associated with structural proteins and are more tightly packaged (heterochromatin). Epigenetic chemical modification of the structural proteins in chromatin also alter the local chromatin structure, in specific chemical modifications of histone proteins by methylation and acetylation. As the cell prepares to divide, i.e., enters mitosis or meiosis, the chromatin packages more tightly to facilitate segregation of the chromosomes during anaphase.

As described above, genomic chromatin of a eukaryotic cell may comprise DNA sequences and a plurality of DNA-binding proteins, as well as certain RNA sequences, assembled into higher order structural or functional regions. As used herein, a "structural or functional feature of a chromatin", refers to a chromatin feature characterized by, or encoding, a function such as a regulatory function of a promoter, terminator, translation initiation, enhancer, etc., or a structural feature such as heterochromatin, euchromatin, a nucleosome, a telomere, or a centromere. A physical feature of a nucleic acid sequence may comprise a functional role and vice versa. As described below, a chromatin of the invention may be a chromatin fragment, and as such may comprise a fragment of a physical or functional feature of a chromatin, or no physical or functional features or known physical or functional features.

The primary protein components of genomic eukaryotic chromatin are histones that compact the DNA into a nucleosome. The nucleosome comprises an octet of histone proteins around which is wound a stretch of double stranded DNA sequence of about 150 to about 250 bp in length. Histones H2A, H2B, H3 and H4 are part of the nucleosome while histone H1 may act to link adjacent nucleosomes together into a higher order structure. Histones are subject to post translational modification which may affect their function in regulating chromatin function. Such modifications may include methylation, citrullination, acetylation, phosphorylation, SUMOylation, ubiquitination, and ADP-ribosylation.

Many further polypeptides and protein complexes interact with the nucleosome and the histones to regulate chromatin function. A "polypeptide complex" as used herein, is intended to describe proteins and polypeptides that assemble together to form a unitary association of factors. The members of a polypeptide complex may interact with each other via non-covalent or covalent bonds. Typically, members of a polypeptide complex will cooperate to enable binding either to a nucleic acid sequence or to polypeptides and proteins already associated with or bound to a nucleic acid sequence in chromatin. Chromatin associated polypeptide complexes may comprise a plurality of proteins and/or polypeptides which each serve to interact with other polypeptides that may be permanently associated with the complex or which may associate transiently, dependent upon cellular conditions and position within the cell cycle. Hence, specific polypeptide complexes may vary in their constituent members at different stages of development, in response to varying physiological conditions or as a factor of the cell cycle. By way of example, in animals, polypeptide complexes with known chromatin remodeling activities include Polycomb group gene silencing complexes, as well as Trithorax group gene activating complexes.

Additionally, a protein associated with a chromatin of the invention may be a protein normally expressed in a cell or may be an exogenous heterologous protein expressed in a cell. In some embodiments, a protein associated with a chromatin of the invention is a protein normally expressed in a cell. In other embodiments, a protein associated with a chromatin of the invention is a protein normally expressed in a cell.

In some embodiments, the methods described herein analyze interactions between nucleotide sequence(s) in a region of interest or target nucleic acid sequences with other sequences. The target nucleic acid sequences may be a genomic region of interest within one (or more) chromosomes and may include regulatory elements. In some embodiments, the regulatory elements are selected from a group comprising promoters, enhancers, silencers, or insulators. The target nucleic acid sequence may comprise a specific genetic locus of interest. A genetic locus is the specific location of a gene or DNA sequence or position on a chromosome. The genomic region of interest may comprise a specific locus, such as the sequence of a gene, together with one or both flanking regions.

The "other nucleotide sequences" i.e., the nucleotide sequences with which the nucleotide sequences within the region of interest interact, may themselves be located in the region of interest, or they may be from other regions, such as other parts of the same chromosome(s) of from a different chromosome. Interactions with such regions may change in case of disease when the regulation of genes has changed or when genes are lost.

As described previously, the methods of the invention may utilize Chromosome Conformation Capture (3C) which is described in Dekker et al., (2002) *Science* 295:1306 or Hi-C described in Belton, J. et al. (2012). Hi-C: A comprehensive technique to capture the conformation of genomes, *Methods*, 58(3). A 3C-like template may be prepared using known methods, such as the method described by Splinter et al., (2004) *Methods Enzymol*. 375, 493-507. Briefly, in one embodiment, a sample-such as cells, tissues or nuclei—is fixed using a cross-linking agent-such as formaldehyde. The primary restriction enzyme digestion is then performed such that the DNA is digested in the context of the cross-linked nucleus. Intramolecular ligation is then performed at low DNA concentrations, which favors ligation between cross-linked DNA fragments (i.e., intramolecular ligation) over ligation between non-cross-linked DNA fragments (i.e., intermolecular or random ligation). Next, the cross links are reversed and the DNA can be purified. The 3C template that is yielded contains restriction fragments that are ligated because they were originally close in the nuclear space.

In one embodiment, the biological sample can be labeled or tagged with a detectable label. The term "label" as used herein refers to any atom or molecule which can be used to provide a detectable signal, and which can be attached to a nucleic acid or protein. Labels may provide signals detectable by fluorescence, radioactivity, colorimetry, gravimetry, X-ray diffraction or absorption, magnetism, enzymatic activity, and the like.

As used herein, the terms "hybridize" and "hybridization" refer to the annealing of a complementary sequence to the target nucleic acid (the sequence to be detected) through base pairing interaction (Marmur and Lane, Proc. Natl. Acad. Sci. USA 46:453 [1960] and Doty et al., Proc. Natl. Acad. Sci. USA 46:461 [1960]). The terms "annealed" and "hybridized" are used interchangeably throughout, and are intended to encompass any specific and reproducible interaction between an oligonucleotide and a target nucleic acid, including binding of regions having only partial complementarity and binding interactions that make use of non-canonical interactions for stability and/or specificity. Nucleotide sequences capable of selective hybridization will be generally be at least 75%, 85%, 90%, 95% or 98% homologous to the corresponding complementary nucleotide sequence over the length of the oligonucleotide probe. Selectivity is determined by the salt and temperature conditions during the hybridization. "Specific hybridization" refers to the binding, duplexing, or hybridizing of a molecule only to a nucleotide sequence under stringent conditions (e.g., 65° C. and 0.1×SSC {1×SSC=0.15 M NaCl, 0.015 M Na-citrate pH 7.0}). Stringent conditions are conditions under which an oligonucleotide probe will hybridize to its target sequence, but to no other sequences. Stringent conditions are sequence-dependent and are different in different circumstances. Longer sequences hybridize specifically at higher temperatures. Generally, very stringent conditions are selected to be about 5° C. lower than the thermal melting point (Tm) for the specific sequence at a defined ionic strength and pH. The hybridization temperature is the temperature below the melting temperature (Tm) and the closer the hybridization temperature is to the Tm the more stringent the hybridization is, meaning that mismatched DNA sequences will not hybridize to each other. In some embodiments, the oligonucleotide sequences are in excess over the genomic DNA to ensure efficient (and quantifiable) hybridization. Typically, stringent conditions include a salt concentration of at least about 0.01 to 1.0 M Na ion concentration (or other salts) at pH 7.0 to 8.3. Stringent conditions can also be achieved with the addition of destabilizing agents-such as formamide or tetraalkyl ammonium salts. The stability of a nucleic acid duplex is measured by the melting temperature, or "$T_m$." The $T_m$ of a nucleic acid duplex under specified conditions is the temperature at which on average half of the base pairs have disassociated.

The term "probe" as used herein refers to an oligonucleotide which forms a duplex structure or other complex with a sequence in another nucleic acid, due to complementarity or other means of reproducible attractive interaction, of at least one sequence in the probe with a sequence in the other nucleic acid. Suitably, the oligonucleotide probes will be at least 15, 20, 25, 30 or 40 nucleotides in length.

With reference to the drawings, FIG. 1 shows an exemplary method for analysis of chromatin interaction events between a first and second chromatin region in situ in a biological tissue sample. As shown in FIG. 1, a biological sample such as a tissue sample can be first treated to preserve or capture a chromatin conformation that is associated with a chromatin interaction event, such as between a first and a second chromatin region. The sample can then be contacted with a first probe and a second probe simultaneously or sequentially in either order. The first chromatin region and the second chromatin region remain in proximity to each other due to the preservation or capture of the chromatin conformation, even after the chromatin interaction event (and/or chromatin associated factor(s) involved in the interaction) is no longer present. In some embodiments, the first probe hybridizes to a first nucleic acid strand in the first chromatin region and the second probe hybridizes to a second nucleic acid strand in the second chromatin region, and the first and second probes are bridged by one another or by one or more bridging probes. In some embodiments, the method comprises connecting the ends of the first and/or second probes or the ends of the one or more bridging probes to form a circular probe, wherein the circular probe comprises a sequence of the first nucleic acid strand or complement thereof and/or a sequence of the second nucleic acid strand or complement thereof, wherein an amplification product of the circular probe is detected, thereby analyzing the chromatin interaction event, e.g., using in situ analysis.

In some embodiments, the method can comprise connecting (e.g., using ligation) the first and the second probes which are for the first and second chromatin regions, respectively. In some embodiments, the method can comprise connecting (e.g., using ligation) the first probe and the second probes via two bridging probes. In some embodiments, the method can comprise connecting (e.g., using ligation) two bridging probes to form the circular probe. In some aspects, a suitable combination of first and/or second probe (e.g., detection probe), bridging probes, and chromatin accessibility probe can be designed to form the circular probe.

In some embodiments, the sample is contacted with a probe that is a chromatin accessing probe. In some embodiments, the first and/or second probes are chromatin accessing probes, e.g., the first and/or second chromatin accessing probe. In some embodiments, the complementary strand to the first nucleic acid strand in the first chromatin region and/or the complementary strand to the second nucleic acid strand in the second chromatin region is not hybridized to a probe, e.g., a chromatin accessing probe. In some embodiments, the complementary strand to the first nucleic acid strand in the first chromatin region is hybridized to a first chromatin accessing probe. In some embodiments, the complementary strand to the second nucleic acid strand in the second chromatin region is hybridized to a second chromatin accessing probe. In some embodiments, the sample is contacted with the first and second chromatin accessing probes simultaneously. In some embodiments, the sample is contacted with the first and second chromatin accessing probes sequentially. In some embodiments, the sample is contacted with the first chromatin accessing probes prior to being contacted with the second chromatin accessing probes. In some embodiments, the sample is contacted with the second chromatin accessing probes prior to being contacted with the first chromatin accessing probes.

Figure 2A:
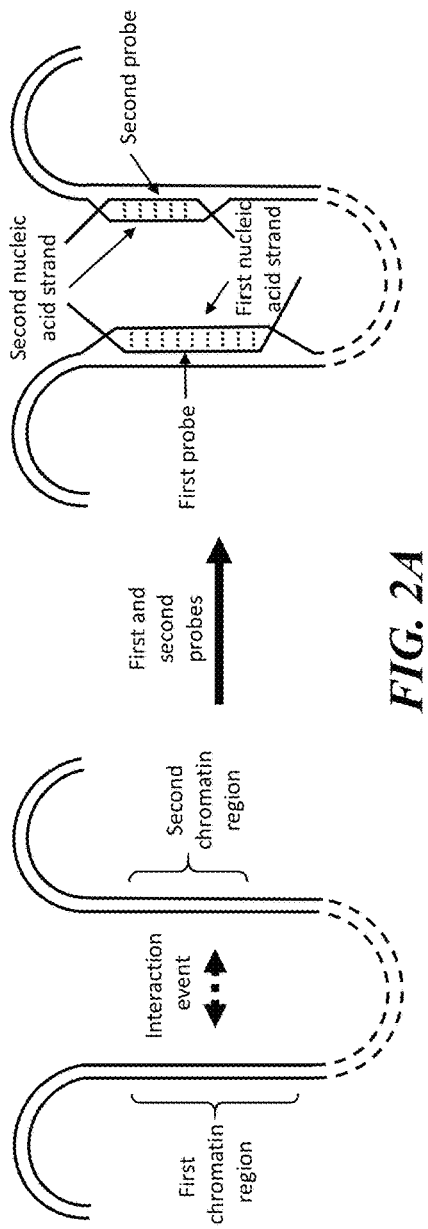
FIG. 2A shows an exemplary embodiment of the hybridization of one or more probes to a nucleic acid strand in a chromatin region, wherein the first and second probes are chromatin accessing probes. The complementary strand to the first nucleic acid strand in the first chromatin region and/or the complementary strand to the second nucleic acid strand in the second chromatin region may but do not need to bind to a chromatin accessing probe. The complementary strands are rendered single-stranded to provide binding sites for further probes such as detection probes with overhangs that can be connected to form a circular probe.

FIG. 2A shows an exemplary embodiment of the hybridization of one or more probes to a nucleic acid strand in a chromatin region, wherein the first and second probes are chromatin accessing probes. The complementary strand to the first nucleic acid strand in the first chromatin region and/or the complementary strand to the second nucleic acid strand in the second chromatin region may but do not need to bind to a chromatin accessing probe. The complementary strands are rendered single-stranded to provide binding sites for further probes such as detection probes with overhangs that can be connected to form a circular probe.

Figure 2B:
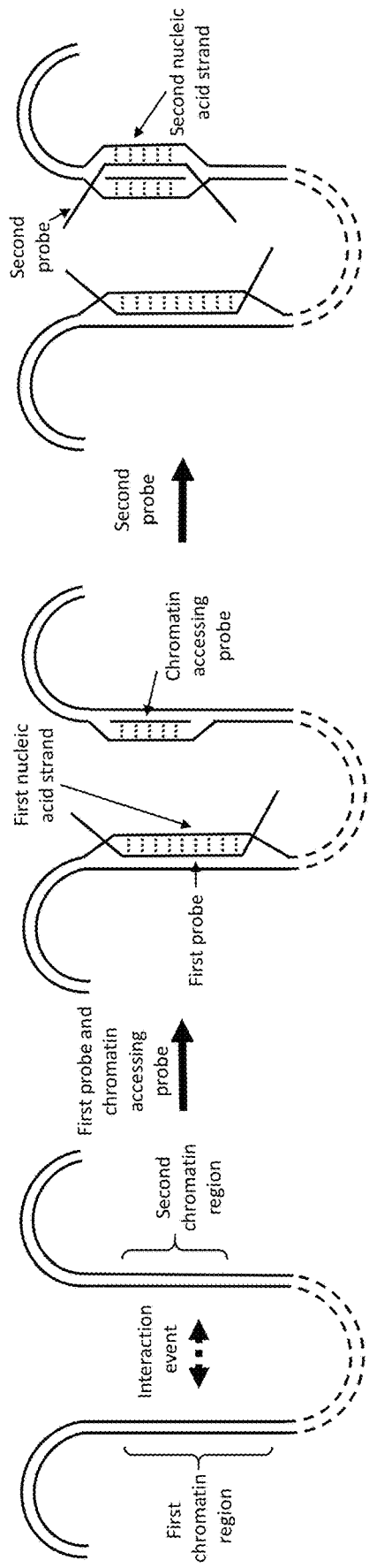
FIG. 2B shows an exemplary embodiment of the hybridization of one or more probes to a nucleic acid strand in a chromatin region, wherein the first probe is a chromatin accessing/detection probe that hybridizes to a first chromatin region, and the second probe is a detection probe that hybridizes to a second nucleic acid strand in the second chromatin region. A separate chromatin accessing probe is provided to open up the duplex in the second chromatin region such that the second probe can bind.

FIG. 2B shows an exemplary embodiment of the hybridization of one or more probes to a nucleic acid strand in a chromatin region, wherein the first probe is a chromatin accessing/detection probe that hybridizes to a first chromatin region, and the second probe is a detection probe that hybridizes to a second nucleic acid strand in the second chromatin region. A separate chromatin accessing probe is provided to open up the duplex in the second chromatin region such that the second probe can bind.

Figure 3A:
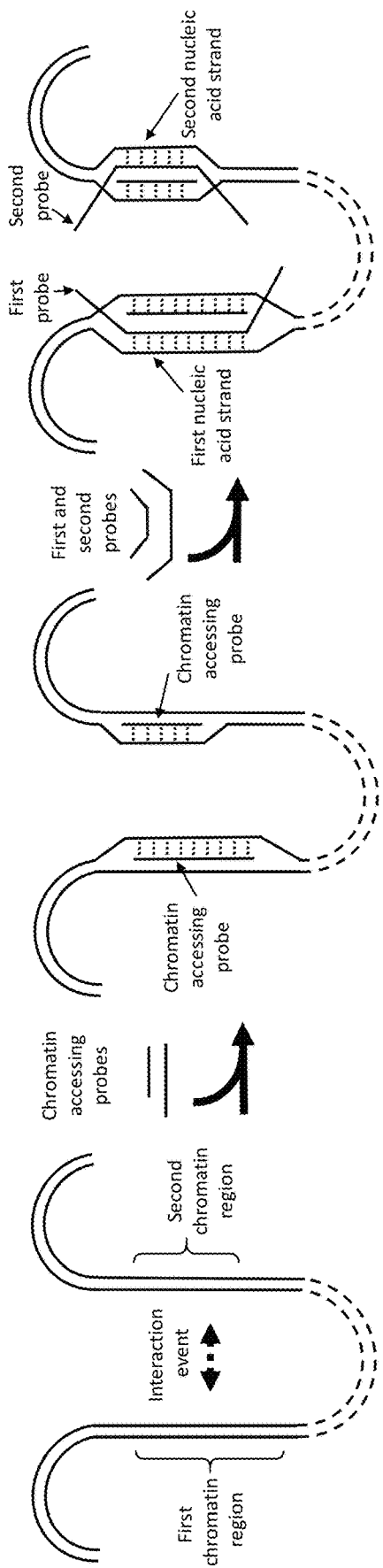
FIG. 3A shows an exemplary embodiment of the hybridization of one or more probes to a nucleic acid strand in a chromatin region, wherein chromatin accessing probes are provided to open up the duplexes in the first and second chromatin regions such that the first and second probes (detection probes with overhangs) can bind.

FIG. 3A shows an exemplary embodiment of the hybridization of one or more probes to a nucleic acid strand in a chromatin region, wherein a first and a second chromatin accessing probes are provided to open up the duplexes in the first and second chromatin regions such that the first and second probes (detection probes with overhangs) can bind.

Figure 3B:
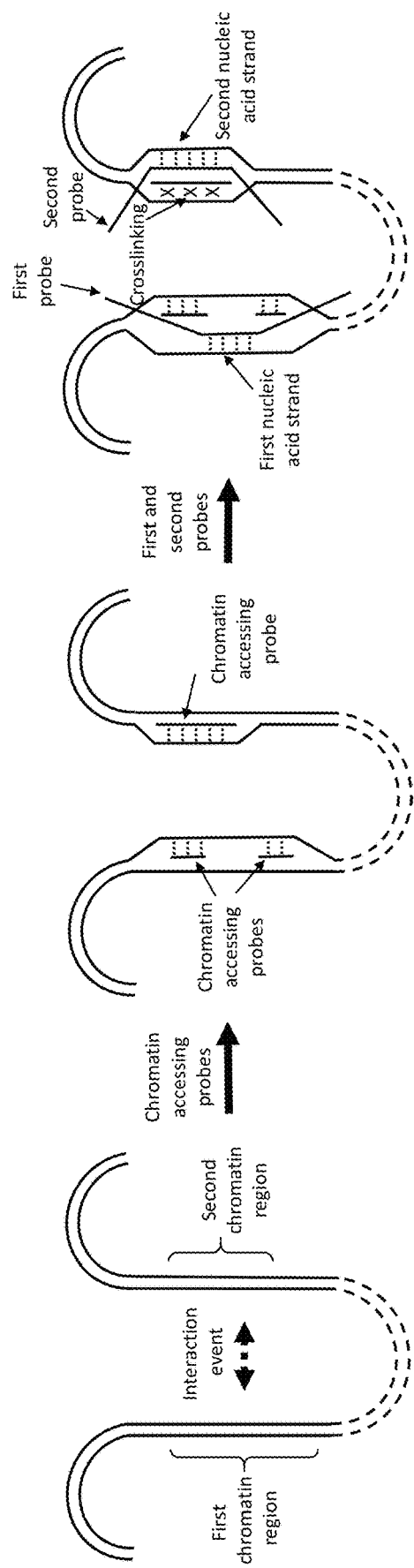
FIG. 3B shows an exemplary embodiment of the hybridization of one or more probes to a nucleic acid strand in a chromatin region. A plurality of chromatin accessing probes can be used to open up a duplex in chromatin. In the first chromatin region, two chromatin accessing probes hybridizing to adjacent sequences on the complementary strand render the first nucleic acid strand single-stranded. The target-binding sequence of the first probe may not be complementary to the two chromatin accessing probes in order to reduce duplex formation between the probes. Upon chromatin accessing probe/complementary chromatin strand hybridization, the chromatin accessing probe may be cross-linked to the complementary strand (e.g., in the second chromatin region) to reduce probe duplex formation and favor detection probe/chromatin strand duplex formation.

FIG. 3B shows an exemplary embodiment of the hybridization of one or more probes to a nucleic acid strand in a chromatin region. The first chromatin accessing probe can comprise a plurality of chromatin accessing probes for use to open up a duplex in chromatin. In the first chromatin region, two chromatin accessing probes hybridizing to adjacent sequences on the complementary strand render the first nucleic acid strand single-stranded. The target-binding sequence of the first probe may not be complementary to the two chromatin accessing probes in order to reduce duplex formation between the probes. Upon chromatin accessing probe/complementary chromatin strand hybridization, the second chromatin accessing probe may be cross-linked to the complementary strand (e.g., in the second chromatin region) to reduce probe duplex formation and favor detection probe/chromatin strand duplex formation.

In some embodiments, the first chromatin accessing probe comprises peptide nucleic acid (PNA). In some embodiments, the second chromatin accessing probe comprises peptide nucleic acid (PNA). In some embodiments, both the first and the second chromatin accessing probe comprise peptide nucleic acid (PNA). In some embodiments, the first and/or second chromatin accessing probes are PNA probes. In some embodiments, the samples is contacted with the first and second chromatin accessing probes that are PNA probes (e.g., the first chromatin accessing probes are PNA probes and/or the second chromatin accessing probes are PNA probes) simultaneously or sequentially in either order.

In some embodiments, the first chromatin accessing probe comprises one or more natural nucleic acid and/or one or more modified or synthetic nucleic acid analogues, such as peptide nucleic acids (PNAs). In some embodiments, the second chromatin accessing probe comprises one or more natural nucleic acids and/or one or more synthetic nucleic acid analogues. In some embodiments, both the first and the second chromatin accessing probe comprises one or more natural nucleic acids, one or more modified nucleic acids, and/or one or more synthetic nucleic acid analogues.

In some embodiments, the one or more synthetic nucleic acid analogues are xeno nucleic acids (XNAs), optionally selected from the group consisting of 1,5-anhydrohexitol nucleic acid (HNA), cyclohexene nucleic acid (CeNA), threose nucleic acid (TNA), glycol nucleic acid (GNA), locked nucleic acid (LNA), peptide nucleic acid (PNA), and fluoro arabino nucleic acid (FANA), and combinations thereof.

In some embodiments, the melting temperature ($T_m$) of the hybridization between the first or second nucleic acid strand and the corresponding complementary strand is lower than the $T_m$ of the hybridization between the first or second chromatin accessing probe and the corresponding complementary strand, e.g., by about 5° C., about 10° C., about 15° C., about 20° C., about 25° C., about 30° C., about 35° C., about 40° C., about 45° C., about 50° C., or by more than 50° C.

In some embodiments, the sample is contacted with the chromatin accessing probe (e.g., the first and/or second chromatin accessing probes) under conditions that allow probe access to single-stranded sequences in the first and/or second chromatin regions. In some embodiments, the conditions that allow probe access to single-stranded sequences in the first and/or second chromatin regions comprises high concentration of chromatin accessing probes. In some embodiments, the sample is contacted with the chromatin accessing probe at a probe concentration of at least about 100 nM, 200 nM, 500 nM, 1 µM, 2 µM, or more than about 2 µM. In some embodiments, the sample is contacted with the chromatin accessing probe at a probe concentration between about 100 nM and about 5 µM, such as between any of about 100 nM to about 1 µM, about 500 nM to about 2 µM, about 1 µM to about 3 µM, and about 2 µM to about 5 µM.

In some embodiments, the sample is contacted with the chromatin accessing probe at a temperature of at least about 40° C., 45° C., 50° C., or more than about 50° C. In some embodiments, the sample is contacted with the chromatin accessing probe at a temperature of between about 40° C. and about 100° C., such as between any of about 40° C. to about 45° C., about 45° C. to about 50° C., about 50° C. to about 55° C., about 55° C. to about 60° C., or about 60° C. to about 100° C. In some embodiments, the sample is incubated with the chromatin accessing probe for at least 30 minutes, 1 hours, 2 hours, 5 hours, or more than 5 hours.

In some embodiments, the molecules of chromatin accessing probes are removed. In some embodiments, the method comprises removing molecules of the chromatin accessing probe that are not specifically hybridized, e.g., using one or more washes such as a stringency wash.

Figure 4:
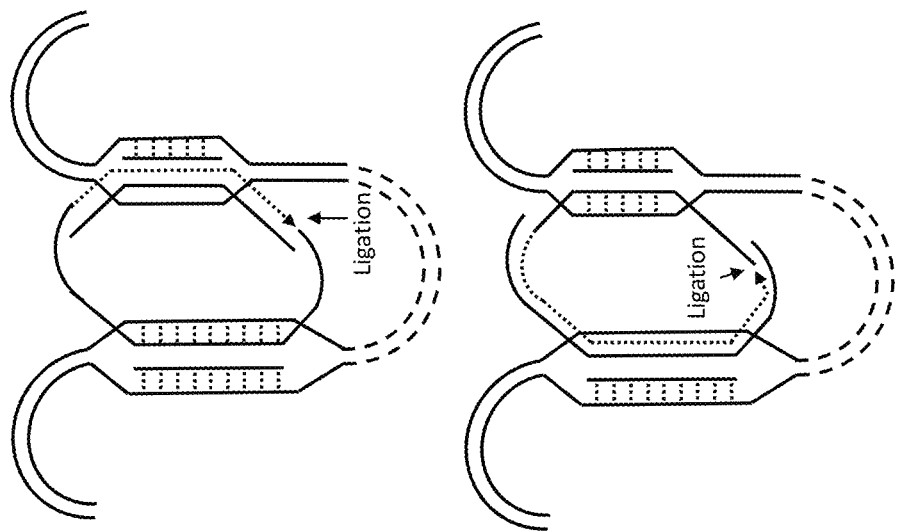
FIG. 4 shows an exemplary embodiment where the first and second probes are bridged by one another, and connecting of the ends of the first probes or the ends of the second probe to form a circular probe. A probe may be extended using the other probe as a template, e.g., using 5' to 3' primer extension (e.g., using a DNA polymerase) followed by ligation (e.g., using a ligase), and/or using hybridization of probes to the template and ligation of the hybridized probes.
Figure 4:
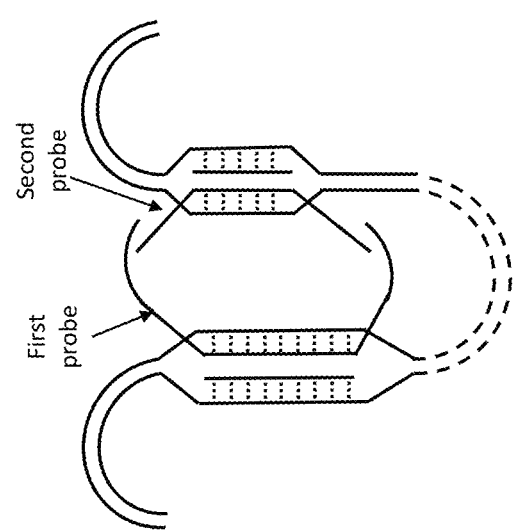

In some embodiments, the ends first and/or second probes, optionally wherein the first and/or second probes are chromatin accessing probes, are connected to form a circular probe. In some embodiments, the ends of the first and/or second probes can be connected directly to form a circular probe. In some embodiments, the first and/or second probes are bridged by one another. In some embodiments, the first and/or second probes comprise a 3' overhang and a 5' overhang flanking a sequence hybridized to the first and second nucleic acid strands, respectively. FIG. 4 illustrates that the 3' overhang of the first probe can be at least partially complementary to the 5' overhang of the second probe, and/or the 5' overhang of the first probe can be at least partially complementary to the 3' overhang of the second probe. In some embodiments, the 3' end of the first probe is extended (e.g., using primer extension and/or ligation) using the second probe as a template, and connecting (e.g., using ligation) the extended 3' end of the first probe to the optionally extended 5' end of the first probe, thereby circularizing the first probe to form the circular probe, wherein the circular probe comprises a sequence of the first nucleic acid strand or complement thereof and/or a sequence of the second nucleic acid strand or complement thereof (FIG. 4).

Figure 5A:
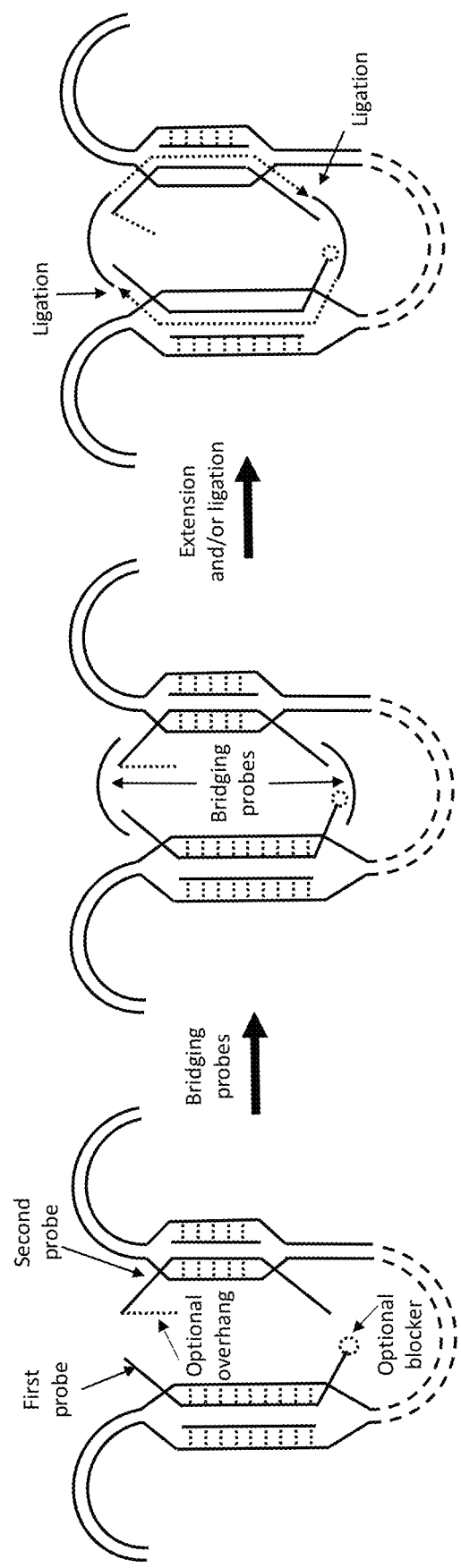
FIG. 5A shows an exemplary embodiment where the first and second probes are bridged by bridging probes. The ends of the bridging probes are extended and then ligated using the first or second probe as a template, thereby forming a circular probe comprising a sequence of the bridging probes, a sequence complementary to the first probe (e.g., a sequence in the first nucleic acid strand in chromatin) and a sequence complementary to the second probe (e.g., a sequence in the second nucleic acid strand in chromatin). Since the first and second probes do not form part of the circular probe, the 5' and/or 3' ends of the first and/or second probes can be blocked for ligation. The 5' and/or 3' ends of the first and/or second probes can optionally comprise one or more additional sequences that do not hybridize to the bridging probes.
Figure 5B:
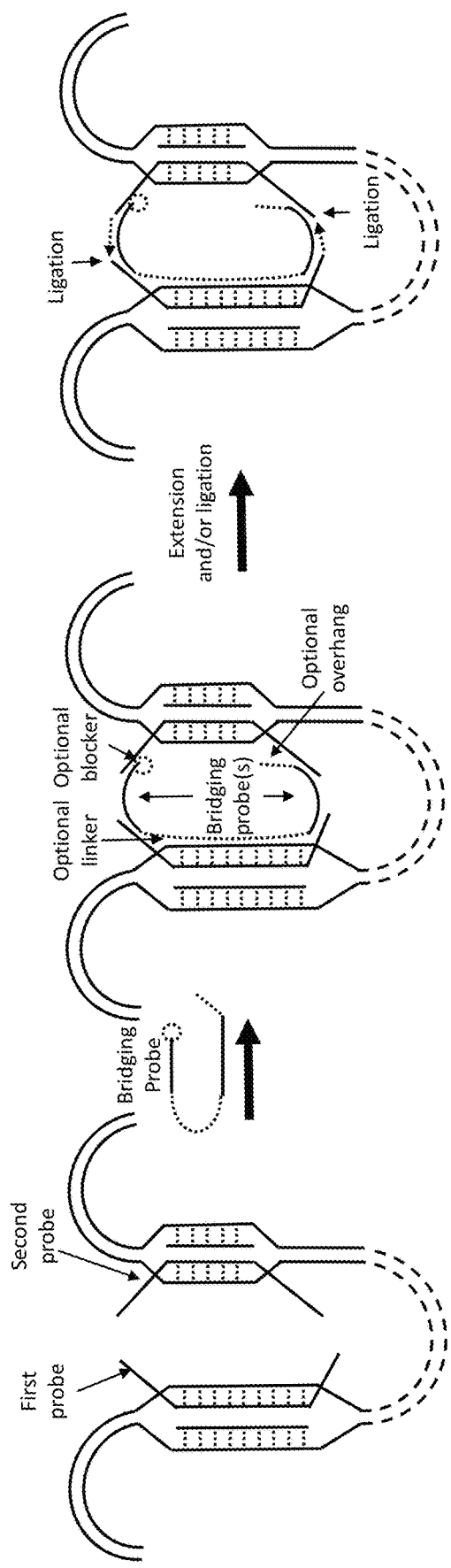
FIG. 5B shows an exemplary embodiment where the first and second probes are bridged by bridging probe(s). The bridging probe sequences bridging the ends of the first and second probes may be linked by a linker or spacer which may comprise a nucleic acid or a non-nucleic acid moiety. Since the bridging probe(s) do not form part of the circular probe, the 5' and/or 3' ends of the bridging probe(s) can be blocked for ligation. The 5' and/or 3' ends of the bridging probe(s) can optionally comprise one or more additional sequences that do not hybridize to the first or second probe. The ends of the first and second probes can be optionally extended and then ligated using the bridging probe(s) as a template, thereby forming a circular probe comprising a sequence of the first probe (which is complementary to the first nucleic acid strand in chromatin) and a sequence of the second probe (which is complementary to the second nucleic acid strand in chromatin).

In some embodiments, the first and second probes, optionally wherein the first and second probes are chromatin accessing probes, are bridged by one or more bridging probes (FIGS. 5A-5B). In some embodiments, the ends of the one or more bridging probes are connected to form a circular probe, wherein the circular probe comprises a sequence of the first nucleic acid strand or complement thereof and/or a sequence of the second nucleic acid strand or complement thereof. In FIG. 5A, the 3' overhang of the first probe and the 5' overhang of the second probe are at least partially complementary to a first bridging probe sequence, and the 5' overhang of the first probe and the 3' overhang of the second probe are at least partially complementary to a second bridging probe sequence. In some embodiments, the first and second bridging probe sequences are in the same bridging probe or in separate bridging probes. Optionally, the bridging probes may comprise a linker/spacer sequence (FIG. 5B; dotted line within the bridging probe). In some embodiments, the 3' overhang of the first probe and the 5' overhang of the second probe can be at least partially complementary to a first bridging probe, and the 5' overhang of the first probe and the 3' overhang of the second probe can be at least partially complementary to a second bridging probe. In some embodiments, the first and/or second probe comprises an additional 3' overhang that is not complementary to a first and/or second bridging probe. In some embodiments, the first and/or second probe do not comprise an additional 3' overhang that is not complementary to a first and/or second bridging probe.

In some embodiments, the 3' end of the first bridging probe can be extended (e.g., using primer extension and/or ligation) using the first probe as a template. In some embodiments, the method comprises connecting (e.g., using ligation) the extended 3' end of the first bridging probe to the optionally extended 5' end of the second bridging probe. In some embodiments, the method comprises extending the 3' end of the second bridging probe (e.g., using primer extension and/or ligation) using the second probe as a template, and connecting (e.g., using ligation) the extended 3' end of the second bridging probe to the optionally extended 5' end of the first bridging probe, thereby connecting the first and second bridging probes to form the circular probe.

Figure 6A:
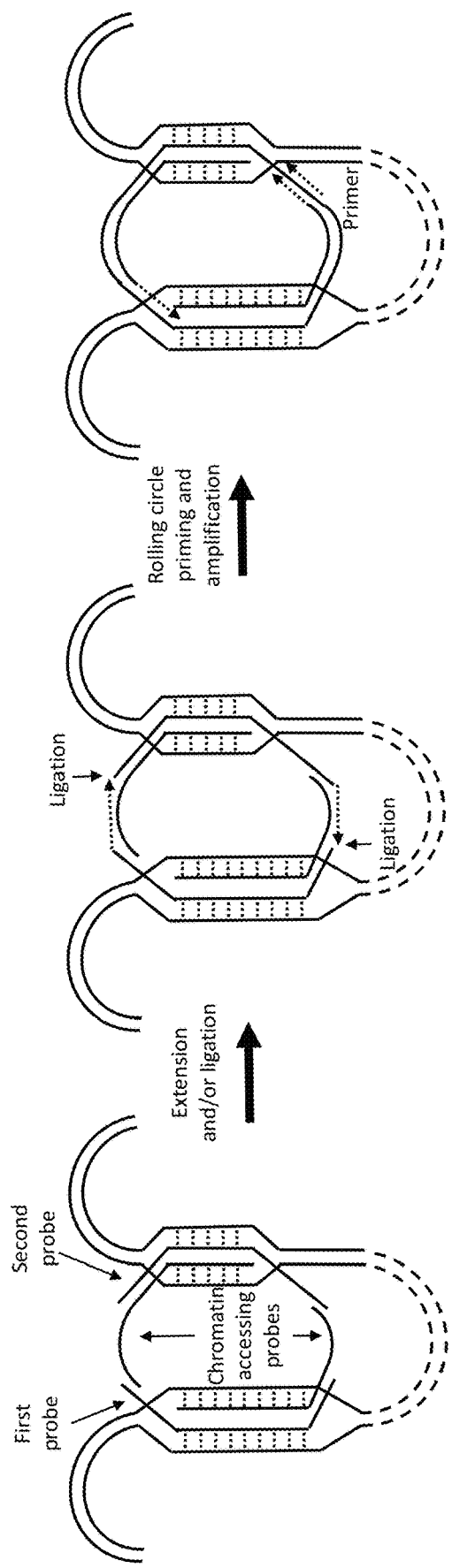
FIG. 6A shows an exemplary embodiment where the first and/or second bridging probe sequences are in a probe (e.g., a chromatin accessing probe) hybridized to the complementary strand to the first nucleic acid strand in the first chromatin region, or in a probe hybridized to the complementary strand to the second nucleic acid strand in the second chromatin region. The ends of the first and second probes can be optionally extended and then ligated using the overhang sequence of a chromatin accessing probe as a template, thereby forming a circular probe comprising a sequence of the first probe (which is complementary to the first nucleic acid strand in chromatin) and a sequence of the second probe (which is complementary to the second nucleic acid strand in chromatin). The overhang sequence of a chromatin accessing probe can be 5' or 3' end blocked or comprise an additional sequence that does not hybridize to the first or second probe. In some instance, after formation of the circular probe, the overhang sequence of a chromatin accessing probe can serve as a rolling circle amplification (RCA) primer for the circular probe. A separate RCA primer may be provided.
Figure 6B:
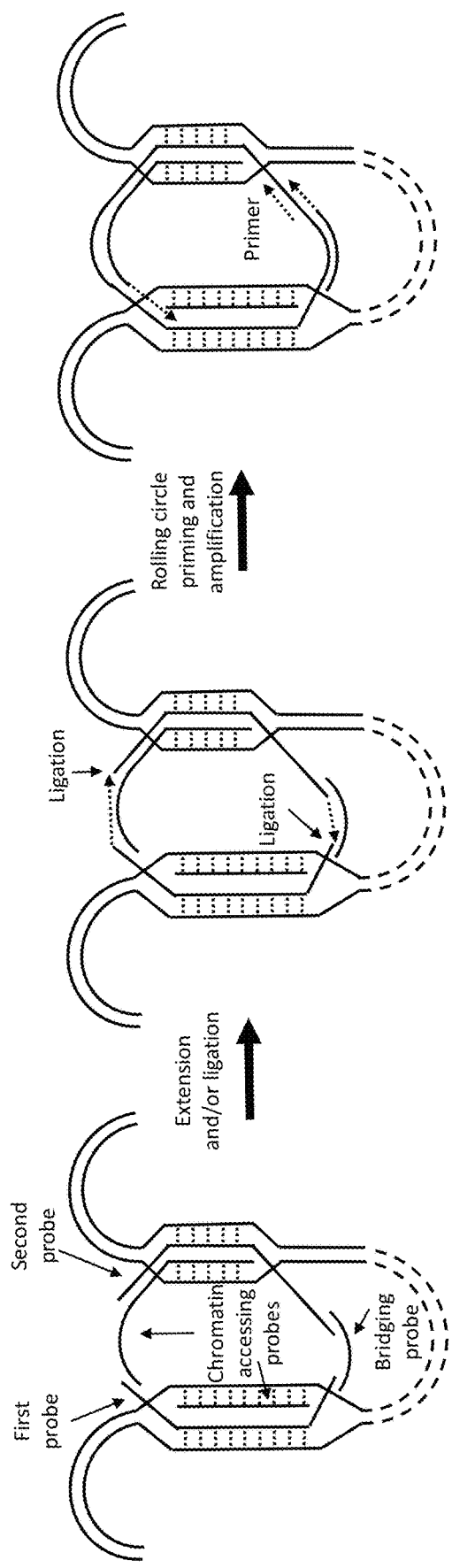
FIG. 6B shows an exemplary embodiment where a bridging probe sequence is in a chromatin accessing probe and another bridging probe sequence is in a bridging probe provided separately from a chromatin accessing probe.
Figure 7:
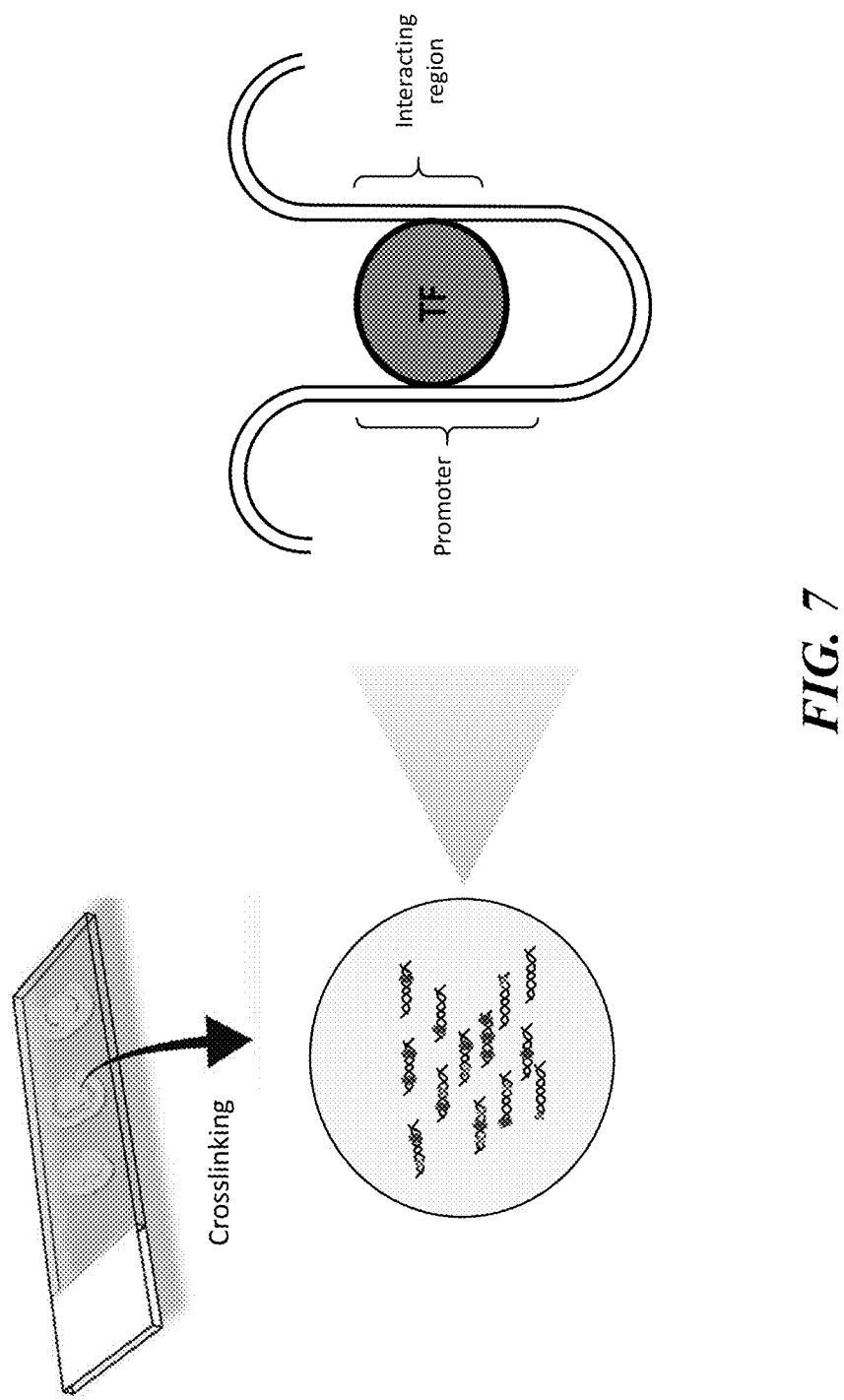
FIG. 7 shows an example of spatial analysis of chromatin interaction events in situ across cell populations in a tissue sample. The chromatin interaction mediated by a transcription factor (TF) between a promoter region and an interacting region (e.g., enhancer) in chromatin is shown as a non-limiting example in FIGS. 7-10.

FIGS. 6A-6B shows a method wherein the first and/or second bridging probe sequences are in a probe (e.g., a chromatin accessing probe) hybridized to the complementary strand to the first nucleic acid strand in the first chromatin region and/or a probe (e.g., a chromatin accessing probe) hybridized to the complementary strand to the second nucleic acid strand in the second chromatin region. In some embodiments, the first and second bridging probe sequences are in a probe (e.g., a chromatin accessing probe) hybridized to the complementary strand to the first nucleic acid strand in the first chromatin region and/or a probe (e.g., a chromatin accessing probe) hybridized to the complementary strand to the second nucleic acid strand in the second chromatin region (e.g., FIG. 6A). In some embodiments, the first bridging probe sequence are in a probe (e.g., a chromatin accessing probe) hybridized to the complementary strand to the first nucleic acid strand in the first chromatin region and/or a probe (e.g., a chromatin accessing probe) hybridized to the complementary strand to the second nucleic acid strand in the second chromatin region. In some embodiments, the second bridging probe is not in a probe (e.g., a chromatin accessing probe) hybridized to the complementary strand to the first nucleic acid strand in the first chromatin region and/or a probe (e.g., a chromatin accessing probe) hybridized to the complementary strand to the second nucleic acid strand in the second chromatin region (e.g., FIG. 6B).

In some embodiments, the 3' end of the first probe is connected to the 5' of end of the second probe by one bridging probe, and the 5' end of the first probe is connected to the 3' end of the second probe by each other (e.g., via the first bridging probe sequence in a probe (e.g., a chromatin accessing probe) hybridized to the complementary strand to the first nucleic acid strand in the first chromatin region and/or a probe (e.g., a chromatin accessing probe) hybridized to the complementary strand to the second nucleic acid strand in the second chromatin region). In some embodiments, the 5' end of the first probe is connected to the 3' of end of the second probe by one bridging probe, and the 3' end of the first probe is connected to the 5' end of the second probe by each other (e.g., via the first bridging probe sequence in a probe (e.g., a chromatin accessing probe) hybridized to the complementary strand to the first nucleic acid strand in the first chromatin region and/or a probe (e.g., a chromatin accessing probe) hybridized to the complementary strand to the second nucleic acid strand in the second chromatin region).

In some embodiments, the circular probe is formed in situ in the sample.

In some embodiments, gaps between the probe oligonucleotides may first be filled prior to ligation, using, for example, Mu polymerase, DNA polymerase, RNA polymerase, reverse transcriptase, VENT polymerase, Taq polymerase, and/or any combinations, derivatives, and variants (e.g., engineered mutants) thereof. In some embodiments, the assay can further include amplification of the ligation products.

In some embodiments, the molecules of the first and/or second probes and/or the one or more bridging probes that are not specifically hybridized are removed, e.g., using one or more washes such as a stringency wash. In some embodiments, the molecules of the first and/or second probes and/or the one or more bridging probes that are not specifically hybridized are removed, e.g., using one or more washes such as a stringency wash.

In some embodiments, the first probe, the second probe, the bridging probe, the circular probe, and/or the chromatin accessing probe comprises a barcode sequence. In some embodiments, the circular probe comprises one or more barcode sequences that correspond to a nucleic acid sequence of interest, e.g., in the first chromatin region and/or in the second chromatin region.

In some embodiments, the barcode sequences of the first probe, the second probe, the bridging probe, the circular probe, and/or the chromatin accessing probe can be the same or different. These nucleic acid barcodes can be used to tag the fragmented DNA, for example by sample, organism, or the like, for example so that multiple samples can be analyzed simultaneously while preserving information about the sample origin. Generally, a barcode can include one or more nucleotide sequences that can be used to identify one or more particular nucleic acids. The barcode can be an artificial sequence, or can be a naturally occurring sequence. A barcode can comprise at least about 1, 2, 3, 4, 5, 6, 7, 8, 9, 10, 11, 12, 13, 14, 15, 16, 17, 18, 19, 20 or more consecutive nucleotides. In some embodiments, a barcode comprises at least about 10, 20, 30, 40, 50, 60, 70 80, 90, 100 or more consecutive nucleotides. In some embodiments, at least a portion of the barcodes in a population of nucleic acids comprising barcodes is different. In some embodiments, at least about 10%, 20%, 30%, 40%, 50%, 60%, 70%, 80%, 90%, 95%, 99% of the barcodes are different. In some such embodiments, all of the barcodes are different. The diversity of different barcodes in a population of nucleic acids comprising barcodes can be randomly generated or non-randomly generated. In some embodiments, a transposon sequence comprises at least one barcode. In some embodiments, a transposon sequence comprises a barcode comprising a first barcode sequence and a second barcode sequence. In some such embodiments, the first barcode sequence can be identified or designated to be paired with the second barcode sequence. For example, a known first barcode sequence can be known to be paired with a known second barcode sequence using a reference table comprising a plurality of first and second barcode sequences known to be paired to one another. In another example, the first barcode sequence can comprise the same sequence as the second barcode sequence. In another example, the first barcode sequence can comprise the reverse complement of the second barcode sequence. In some embodiments, the first barcode sequence and the second barcode sequence are different ("bi-codes"). It will be understood that in some embodiments, the vast number of available barcodes permits each barcoded nucleic acid molecule to comprise a unique identification. Unique identification of each molecule in a mixture of template nucleic acids can be used in several applications to identify individual nucleic acid molecules, in samples having multiple chromosomes, genomes, cells, cell types, cell disease states, and species, for example in haplotype sequencing, parental allele discrimination, metagenomic sequencing, and sample sequencing of a genome.

In some embodiments, the methods provided herein can be multiplexed (e.g., the sample is analyzed to detect a plurality of chromatin interaction events). In some embodiments, the detection of a plurality of chromatin interaction events occurs in parallel. In some embodiments, the detection of a plurality of chromatin interaction events occurs sequentially. In some embodiments, the first circular probe is associated with a first chromatin interaction event and a second circular probe is associated with a second chromatin interaction event, and the first and second circular probe each comprises a barcode sequence or complement thereof that corresponds to the first and/or second probe or the chromatin interaction event.

In some embodiments, the chromatin interaction event involves one or more chromatin regions other than the first and second chromatin regions, and the circular probe further comprises a sequence or complement thereof of a nucleic acid strand in the one or more other chromatin regions.

Figure 8:
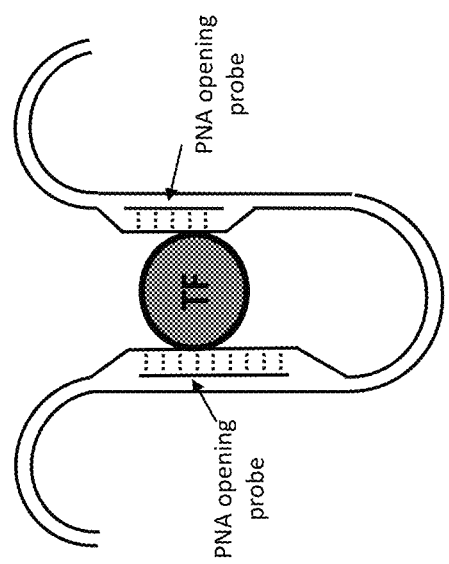
FIG. 8 shows an exemplary embodiment where PNA opening probes and detection probe are hybridized to the target sequences involved in a chromatin interaction event.
Figure 8:
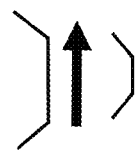
Figure 8:
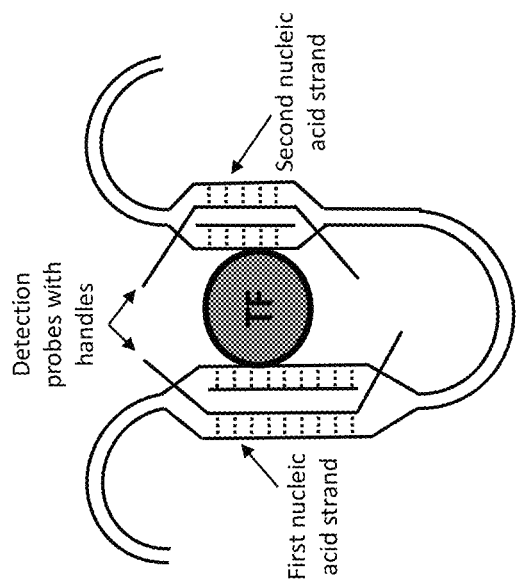
Figure 9:
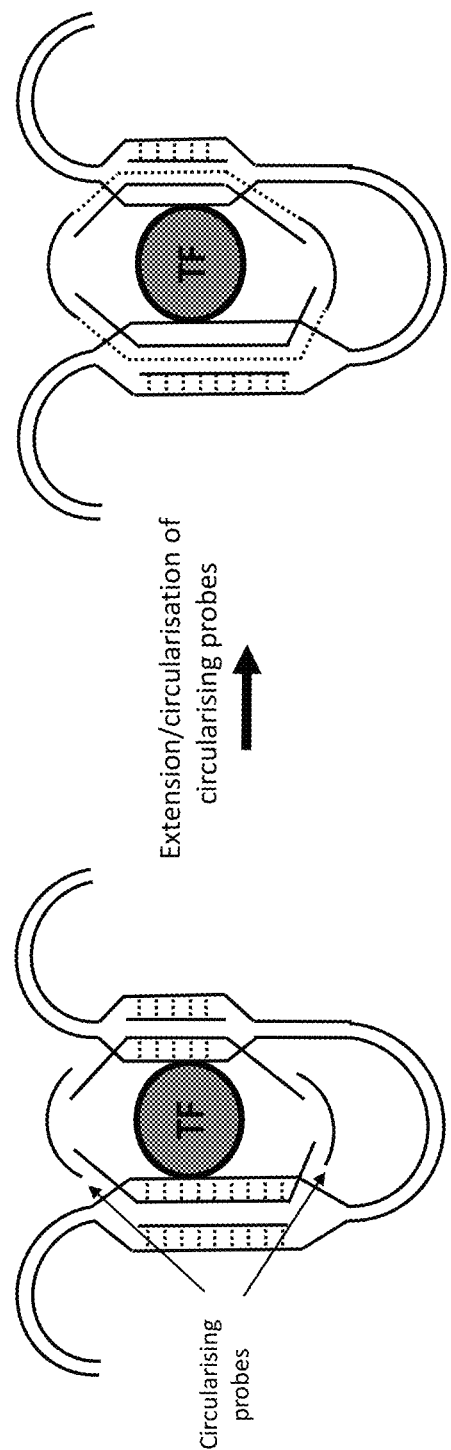
FIG. 9 shows a method comprising exemplary steps of hybridizing circularizing probes to bridge the ends of detection probes and extending the circularizing probes using the detection probes (either detection probe can be extended in the 5' to 3' or the 3' to 5' direction) as a template. The ends of the extended circularizing probes can be connected (e.g., ligated) to form a circular probe.

With reference to the embodiment depicted in FIGS. 7-10, in steps 1 and 2, a slide is prepared with a biological sample (e.g., tissue sample) and subjected to formaldehyde cross-linking agent to chemically cross-link chromatin to associated factors. In FIG. 8, peptide nucleic acid (PNA) probes comprising oligonucleotide sequences that specifically target interacting genomic regions of interest (e.g., interacting promoter and enhancer nucleic acid sequences in close spatial proximity to one another) are introduced and hybridized to the genomic sequences. Also, as shown in FIG. 8, detection probes comprising oligonucleotide sequences that specifically target the same interacting genomic regions of interest are introduced. In one embodiment, detection probes hybridize to one strand and the PNA probes hybridize to the other strand of the double stranded genomic sequence. The detection probes can further comprise 3' and 5' overhangs or extensions. In FIG. 9, circularizing probes are introduced and hybridized to the 3' and 5' overhangs of the detection probes, thus forming a bridge between detection probes hybridized to the enhancer regions and detection probes hybridized to the promoter regions engaged in a chromatin interaction event. As shown in FIG. 9, the circularizing probes are extended with a DNA polymerase to form a unified circular nucleic acid molecule comprising all or part of the target interacting sequences of interest.

Figure 10:
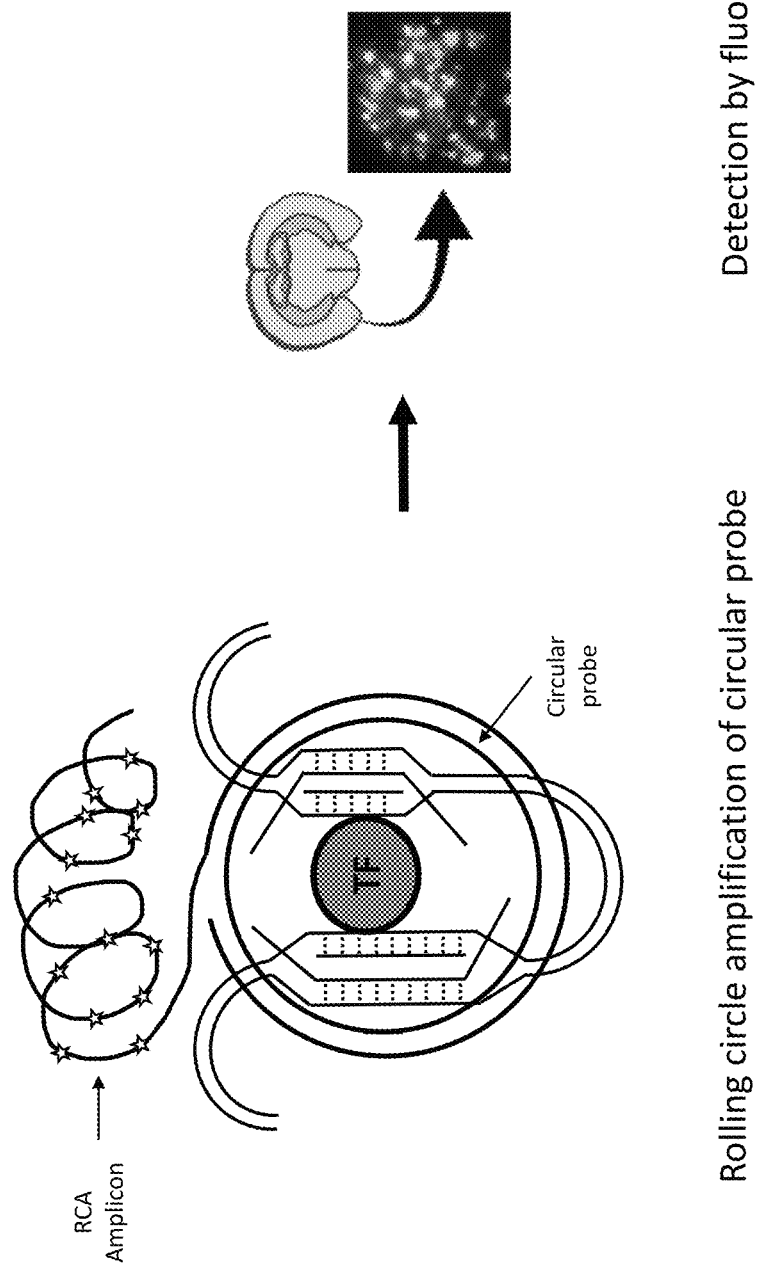
FIG. 10 shows a method comprising exemplary steps of rolling circle amplification and detection of fluorescent signals. Detectably labeled RCA amplicon is exemplified. However, the amplicon per se may not be detectably labeled and may be detected by a detectably-labeled probe (not shown). Alternatively, the amplicon may be recognized by an intermediate probe (which may not be detectably labeled per se; not shown), and the intermediate probe may be detected by a detectably-labeled probe.

In FIG. 10, the unified circular nucleic acid is amplified in situ via rolling circle amplification (RCA) and fluorophore labeled for detection by fluorescence in situ hybridization (FISH). Suitable strategies utilizing padlock probes and rolling circle amplification are described in Qian, X., et al. (2018). A spatial atlas of inhibitory cell types in mouse hippocampus, bioRxiv doi: https://doi.org/10.1101/431957. In FIG. 10, detectably labeled RCA amplicon is exemplified. However, the ampliconper se may not be detectably labeled and may be detected by a detectably-labeled probe (not shown). Alternatively, the amplicon may be recognized by an intermediate probe (which may not be detectably labeled per se; not shown), and the intermediate probe may be detected by a detectably-labeled probe. As used herein, a detectably labeled oligonucleotide (e.g., detection probe) is labeled with a detectable moiety. In some embodiments, a detectably labeled oligonucleotide comprises one detectable moiety. In some embodiments, a detectably labeled oligonucleotide comprises two or more detectable moieties. In some embodiments, a detectably labeled oligonucleotide has one detectable moiety. In some embodiments, a detectably labeled oligonucleotide has two or more detectable moiety. Probes and methods for binding and identifying a target nucleic acid have been described in, e.g., US2003/0013091, US2007/0166708, US2010/0015607, US2010/0261026, US2010/0262374, US2010/0112710, US2010/0047924, and US2014/0371088, each of which is incorporated herein by reference in its entirety. In some embodiments, a detectable moiety is or comprises a nanomaterial. In some embodiments, a detectable moiety is or compresses a nanoparticle. In some embodiments, a detectable moiety is or comprises a quantum dot. In some embodiments, a detectable moiety is a quantum dot. In some embodiments, a detectable moiety comprises a quantum dot. In some embodiments, a detectable moiety is or comprises a gold nanoparticle. In some embodiments, a detectable moiety is a gold nanoparticle. In some embodiments, a detectable moiety comprises a gold nanoparticle. One of skill in the art understands that, in some embodiments, selection of label for a particular probe may be determined based on a variety of factors, including, for example, size, types of signals generated, manners attached to or incorporated into a probe, properties of the cellular constituents including their locations within the cell, properties of the cells, types of interactions being analyzed, and etc. For example, in some embodiments, probes are labeled with either Cy3 or Cy5 that has been synthesized to carry an N-hydroxysuccinimidyl ester (NHS-ester) reactive group. Since NHS-esters react readily with aliphatic amine groups, nucleotides can be modified with aminoalkyl groups. This can be done through incorporating aminoalkyl-modified nucleotides during synthesis reactions. In some embodiments, a label is used in every 60 bases to avoid quenching effects.

In some embodiments, one or two sets of probes may be used, for example, excluding the detection or the PNA probes. Additionally, alternative probe designs may be used, for example padlock probes, so long as the final amplicon comprises all or part of the target sequences engaged in a chromatin interaction event (e.g., promoter/enhancer).

In some embodiments, the methods described herein can be multiplexed. For example, following detection and imaging techniques, the sample (e.g., biological or tissue sample on substrate) may be chemically treated (e.g., bleached) and signal quenched from the first label and the procedures described above repeated for other target nucleic acid sequences engaged in chromatin interaction events. The procedures may be repeated for multiple rounds until prevented by molecular degradation or other inhibitory issue—each round utilizing a distinguishable label thereby creating a layered array of multiple chromatin interaction events across cell populations. Suitable commercially available techniques are available, for example, MACSima™ Imaging Platform or the Akoya Biosciences Phenoptics Multispectral Imaging platform.

In some embodiments, the amplification product generated by rolling circle amplification can be sequenced in situ by in situ sequencing techniques or other suitable technique.

In some embodiments, the amplification product comprises multiple copies of the one or more barcode sequences or a complement thereof, the sequence of the first nucleic acid strand or complement thereof, and the sequence of the second nucleic acid strand or complement thereof. In some embodiments, the amplification product is formed in situ in the sample. In some embodiments, the amplification product is formed using rolling circle amplification (RCA) of the circular probe, optionally wherein the RCA is a linear RCA, a branched RCA, a dendritic RCA, or any combination thereof. In some embodiments, the amplification product is formed using a Phi29 polymerase. In some embodiments, the amplification is performed at a temperature between about 20° C. and about 60° C., optionally between about 30° C. and about 40° C.

In some embodiments, the amplifying is achieved by performing rolling circle amplification (RCA). In other embodiments, a primer that hybridizes to the circular probe or circularized probe is added and used as such for amplification. In some embodiments, the RCA comprises a linear RCA, a branched RCA, a dendritic RCA, or any combination thereof.

In some embodiments, the amplification is performed at a temperature between or between about 20° C. and about 60° C. In some embodiments, the amplification is performed at a temperature between or between about 30° C. and about 40° C. In some aspects, the amplification step, such as the rolling circle amplification (RCA) is performed at a temperature between at or about 25° C. and at or about 50° C., such as at or about 25° C., 27° C., 29° C., 31° C., 33° C., 35° C., 37° C., 39° C., 41° C., 43° C., 45° C., 47° C., or 49° C.

In some embodiments, upon addition of a DNA polymerase in the presence of appropriate dNTP precursors and other cofactors, a primer is elongated to produce multiple copies of the circular template. This amplification step can utilize isothermal amplification or non-isothermal amplification. In some embodiments, after the formation of the hybridization complex and association of the amplification probe, the hybridization complex is rolling-circle amplified to generate a cDNA nanoball (i.e., amplicon) containing multiple copies of the cDNA. Techniques for rolling circle amplification (RCA) are known in the art such as linear RCA, a branched RCA, a dendritic RCA, or any combination thereof (See, e.g., Baner et al, Nucleic Acids Research, 26:5073-5078, 1998; Lizardi et al, Nature Genetics 19:226, 1998; Mohsen et al., Acc Chem Res. 2016 Nov. 15; 49(11): 2540-2550; Schweitzer et al. Proc. Natl Acad. Sci. USA 97:101 13-1 19, 2000; Faruqi et al, BMC Genomics 2:4, 2000; Nallur et al, Nucl. Acids Res. 29:e118, 2001; Dean et al. Genome Res. 11:1095-1099, 2001; Schweitzer et al, Nature Biotech. 20:359-365, 2002; U.S. Pat. Nos. 6,054, 274, 6,291,187, 6,323,009, 6,344,329 and 6,368,801). Exemplary polymerases for use in RCA comprise DNA polymerase such phi29 (φ29) polymerase, Klenow fragment, *Bacillus stearothermophilus* DNA polymerase (BST), T4 DNA polymerase, T7 DNA polymerase, or DNA polymerase I. In some aspects, DNA polymerases that have been engineered or mutated to have desirable characteristics can be employed. In some embodiments, the polymerase is phi29 DNA polymerase.

In some aspects, during the amplification step, modified nucleotides can be added to the reaction to incorporate the modified nucleotides in the amplification product (e.g., nanoball). Exemplary of the modified nucleotides comprise amine-modified nucleotides. In some aspects of the methods, for example, for anchoring or cross-linking of the generated amplification product (e.g., nanoball) to a scaffold, to cellular structures and/or to other amplification products (e.g., other nanoballs). In some aspects, the amplification products comprises a modified nucleotide, such as an amine-modified nucleotide. In some embodiments, the amine-modified nucleotide comprises an acrylic acid N-hydroxysuccinimide moiety modification. Examples of other amine-modified nucleotides comprise, but are not limited to, a 5-Aminoallyl-dUTP moiety modification, a 5-Propargylamino-dCTP moiety modification, a N6-6-Aminohexyl-dATP moiety modification, or a 7-Deaza-7-Propargylamino-dATP moiety modification.

In some aspects, the polynucleotides and/or amplification product (e.g., amplicon) can be anchored to a polymer matrix. For example, the polymer matrix can be a hydrogel. In some embodiments, one or more of the polynucleotide probe(s) can be modified to contain functional groups that can be used as an anchoring site to attach the polynucleotide probes and/or amplification product to a polymer matrix. Exemplary modification and polymer matrix that can be employed in accordance with the provided embodiments comprise those described in, for example, WO 2014/163886, WO 2017/079406, US 2016/0024555, US 2018/0251833 and US 2017/0219465. In some examples, the scaffold also contains modifications or functional groups that can react with or incorporate the modifications or functional groups of the probe set or amplification product.

In some examples, the scaffold can comprise oligonucleotides, polymers or chemical groups, to provide a matrix and/or support structures.

The amplification products may be immobilized within the matrix generally at the location of the nucleic acid being amplified, thereby creating a localized colony of amplicons. The amplification products may be immobilized within the matrix by steric factors. The amplification products may also be immobilized within the matrix by covalent or noncovalent bonding. In this manner, the amplification products may be considered to be attached to the matrix. By being immobilized to the matrix, such as by covalent bonding or cross-linking, the size and spatial relationship of the original amplicons is maintained. By being immobilized to the matrix, such as by covalent bonding or cross-linking, the amplification products are resistant to movement or unraveling under mechanical stress.

In some aspects, the amplification products are copolymerized and/or covalently attached to the surrounding matrix thereby preserving their spatial relationship and any information inherent thereto. For example, if the amplification products are those generated from DNA or RNA within a cell embedded in the matrix, the amplification products can also be functionalized to form covalent attachment to the matrix preserving their spatial information within the cell thereby providing a subcellular localization distribution pattern. In some embodiments, the provided methods involve embedding the one or more polynucleotide probe sets and/or the amplification products in the presence of hydrogel subunits to form one or more hydrogel-embedded amplification products. In some embodiments, the hydrogel-tissue chemistry described comprises covalently attaching nucleic acids to in situ synthesized hydrogel for tissue clearing, enzyme diffusion, and multiple-cycle sequencing while an existing hydrogel-tissue chemistry method cannot. In some embodiments, to enable amplification product embedding in the tissue-hydrogel setting, amine-modified nucleotides are comprised in the amplification step (e.g., RCA), functionalized with an acrylamide moiety using acrylic acid N-hydroxysuccinimide esters, and copolymerized with acrylamide monomers to form a hydrogel.

In some embodiments, sequence analysis can be performed by sequential fluorescence hybridization (e.g., sequencing by hybridization). Sequential fluorescence hybridization can involve sequential hybridization of detection probes comprising an oligonucleotide and a detectable label.

In some embodiments, sequencing can be performed by sequencing-by-synthesis (SBS). In some embodiments, a sequencing primer is complementary to sequences at or near the one or more barcode(s). In such embodiments, sequencing-by-synthesis can comprise reverse transcription and/or amplification in order to generate a template sequence from which a primer sequence can bind. Exemplary SBS methods comprise those described for example, but not limited to, US 2007/0166705, US 2006/0188901, U.S. Pat. No. 7,057,026, US 2006/0240439, US 2006/0281109, US20110059865, US 2005/0100900, US2008/0280773, US20090118128, US 2012/0270305, US 2013/0260372, and US 2013/0079232.

In some embodiments, sequencing can be performed using single molecule sequencing by ligation. Such techniques utilize DNA ligase to incorporate oligonucleotides and identify the incorporation of such oligonucleotides. The oligonucleotides typically have different labels that are correlated with the identity of a particular nucleotide in a sequence to which the oligonucleotides hybridize. Aspects and features involved in sequencing by ligation are described, for example, in Shendure et al. *Science* (2005), 309: 1728-1732, and in U.S. Pat. Nos. 5,599,675; 5,750,341; 6,969,488; 6,172,218; and 6,306,597.

In some embodiments, the detecting of the amplification product comprises labeling the amplification product with a fluorophore, an isotope, a mass tag, or a combination thereof. In some embodiments, the detecting of the amplification product comprises directly or indirectly hybridizing one or more probes to the amplification product (e.g., a detectably labeled probe), optionally wherein a fluorescently labeled probe is directly hybridized to the amplification product, or optionally wherein a fluorescently labeled probe is directly hybridized to an intermediate probe which is hybridized to the amplification product. In some embodiments, the amplification product is detected in situ in the sample.

In some embodiments, the barcodes are targeted by detectably labeled detection oligonucleotides, such as fluorescently labeled oligonucleotides. In some embodiments, one or more decoding schemes are used to decode the signals, such as fluorescence, for sequence determination. In any of the embodiments herein, barcodes can be analyzed (e.g., detected or sequenced) using any suitable methods or techniques, comprising those described herein, such as RNA sequential probing of targets (RNA SPOTs), sequential fluorescent in situ hybridization (seqFISH), single-molecule fluorescent in situ hybridization (smFISH), multiplexed error-robust fluorescence in situ hybridization (MERFISH), hybridization-based in situ sequencing (HybISS), in situ sequencing, targeted in situ sequencing, fluorescent in situ sequencing (FISSEQ), or spatially-resolved transcript amplicon readout mapping (STARmap). In some embodiments, the methods provided herein comprise analyzing the barcodes by sequential hybridization and detection with a plurality of labelled probes. Exemplary decoding schemes are described in Eng et al., "Transcriptome-scale Super-Resolved Imaging in Tissues by RNA SeqFISH+," *Nature* 568(7751):235-239 (2019); Chen et al., "Spatially resolved, highly multiplexed RNA profiling in single cells," *Science;* 348(6233):aaa6090 (2015); Gyllborg et al., Nucleic Acids Res (2020) 48(19):e112; U.S. Pat. No. 10,457,980 B2; US 2016/0369329 A1; WO 2018/026873 A1; and US 2017/0220733 A1, all of which are incorporated by reference in their entirety. In some embodiments, these assays enable signal amplification, combinatorial decoding, and error correction schemes at the same time.

In some embodiments, nucleic acid hybridization can be used for sequencing. These methods utilize labeled nucleic acid decoder probes that are complementary to at least a portion of a barcode sequence. Multiplex decoding can be performed with pools of many different probes with distinguishable labels. Non-limiting examples of nucleic acid hybridization sequencing are described for example in U.S. Pat. No. 8,460,865, and in Gunderson et al., *Genome Research* 14:870-877 (2004), the entire contents of each of which are incorporated herein by reference. In any of the preceding embodiments, the methods provided herein can include analyzing the barcodes by sequential hybridization and detection with a plurality of labelled probes (e.g., detection oligonucleotides).

In some embodiments, real-time monitoring of DNA polymerase activity can be used during sequencing. For example, nucleotide incorporations can be detected through fluorescence resonance energy transfer (FRET), as described for example in Levene et al., *Science* (2003), 299, 682-686, Lundquist et al., *Opt. Lett.* (2008), 33, 1026-1028, and term "perfectly et al., *Proc. Natl. Acad. Sci. USA* (2008), 105, 1176-1181.

In some aspects, the analysis and/or sequence determination can be carried out at room temperature for best preservation of tissue morphology with low background noise and error reduction. In some embodiments, the analysis and/or sequence determination comprises eliminating error accumulation as sequencing proceeds.

In some embodiments, the analysis and/or sequence determination involves washing to remove unbound polynucleotides, thereafter revealing a fluorescent product for imaging.

In some aspects, the detection (comprising imaging) is carried out using any of a number of different types of microscopy, e.g., confocal microscopy, two-photon microscopy, light-field microscopy, intact tissue expansion microscopy, and/or CLARITY™-optimized light sheet microscopy (COLM).

In some embodiments, fluorescence microscopy is used for detection and imaging of the detection probe. In some aspects, a fluorescence microscope is an optical microscope that uses fluorescence and phosphorescence instead of, or in addition to, reflection and absorption to study properties of organic or inorganic substances. In fluorescence microscopy, a sample is illuminated with light of a wavelength which excites fluorescence in the sample. The fluoresced light, which is usually at a longer wavelength than the illumination, is then imaged through a microscope objective. Two filters may be used in this technique; an illumination (or excitation) filter which ensures the illumination is near monochromatic and at the correct wavelength, and a second emission (or barrier) filter which ensures none of the excitation light source reaches the detector. Alternatively, these functions may both be accomplished by a single dichroic filter. The "fluorescence microscope" comprises any microscope that uses fluorescence to generate an image, whether it is a more simple set up like an epifluorescence microscope, or a more complicated design such as a confocal microscope, which uses optical sectioning to get better resolution of the fluorescent image.

In some embodiments, confocal microscopy is used for detection and imaging of the detection probe. Confocal microscopy uses point illumination and a pinhole in an optically conjugate plane in front of the detector to eliminate out-of-focus signal. As only light produced by fluorescence very close to the focal plane can be detected, the image's optical resolution, particularly in the sample depth direction, is much better than that of wide-field microscopes. However, as much of the light from sample fluorescence is blocked at the pinhole, this increased resolution is at the cost of decreased signal intensity—so long exposures are often required. As only one point in the sample is illuminated at a time, 2D or 3D imaging requires scanning over a regular raster (i.e., a rectangular pattern of parallel scanning lines) in the specimen. The achievable thickness of the focal plane is defined mostly by the wavelength of the used light divided by the numerical aperture of the objective lens, but also by the optical properties of the specimen. The thin optical sectioning possible makes these types of microscopes particularly good at 3D imaging and surface profiling of samples. CLARITY™-optimized light sheet microscopy (COLM) provides an alternative microscopy for fast 3D imaging of large clarified samples. COLM interrogates large immunostained tissues, permits increased speed of acquisition and results in a higher quality of generated data.

Other types of microscopy that can be employed comprise bright field microscopy, oblique illumination microscopy, dark field microscopy, phase contrast, differential interference contrast (DIC) microscopy, interference reflection microscopy (also known as reflected interference contrast, or RIC), single plane illumination microscopy (SPIM), super-resolution microscopy, laser microscopy, electron microscopy (EM), Transmission electron microscopy (TEM), Scanning electron microscopy (SEM), reflection electron microscopy (REM), Scanning transmission electron microscopy (STEM) and low-voltage electron microscopy (LVEM), scanning probe microscopy (SPM), atomic force microscopy (ATM), ballistic electron emission microscopy (BEEM), chemical force microscopy (CFM), conductive atomic force microscopy (C-AFM), electrochemical scanning tunneling microscope (ECSTM), electrostatic force microscopy (EFM), fluidic force microscope (FuidFM), force modulation microscopy (FMM), feature-oriented scanning probe microscopy (FOSPM), kelvin probe force microscopy (KPFM), magnetic force microscopy (MFM), magnetic resonance force microscopy (MRFM), near-field scanning optical microscopy (NSOM) (or SNOM, scanning near-field optical microscopy, SNOM, Piezoresponse Force Microscopy (PFM), PS™, photon scanning tunneling microscopy (PSTM), PTMS, photothermal microspectroscopy/microscopy (PTMS), SCM, scanning capacitance microscopy (SCM), SECM, scanning electrochemical microscopy (SECM), SGM, scanning gate microscopy (SGM), SHPM, scanning Hall probe microscopy (SHPM), SICM, scanning ion-conductance microscopy (SICM), SPSM spin polarized scanning tunneling microscopy (SPSM), SSRM, scanning spreading resistance microscopy (SSRM), SThM, scanning thermal microscopy (SThM), STM, scanning tunneling microscopy (STM), STP, scanning tunneling potentiometry (STP), SVM, scanning voltage microscopy (SVM), and synchrotron x-ray scanning tunneling microscopy (SXSTM), and intact tissue expansion microscopy (exM).

The probes described herein may be used for analyzing a sequence of an extension product (e.g., RCA product) associated with a target nucleic acid or target analyte. In some embodiments, the sequence to be analyzed is a nucleic acid barcode sequence. For example, the nucleic acid barcode sequence may correspond to an analyte or a portion (e.g., a nucleic acid sequence) thereof or a labelling agent for the analyte or portion thereof in the biological sample.

In some embodiments, the detection further comprises imaging the complex comprising the probe and a target nucleic acid or target analyte (e.g., or a product or derivative thereof), e.g., by optical imaging. For example, the one or more probes may be barcoded probes comprising one or more nucleic acid barcode sequences, which can be directly or indirectly bound by detectably-labeled detection probes (e.g., fluorescently labeled detection probes). A detectable signal or a series of signals such as fluorescence comprising a spatial pattern and/or a temporal pattern may be analyzed to reveal the presence/absence, distribution, location, amount, level, expression, or activity of the one or more analytes in the sample. In some embodiments, the one or more analytes (e.g., target sequences) are analyzed (e.g., by imaging) in situ in a tissue sample without migrating out of a cell of the tissue sample. In some embodiments, the one or more protein analytes are analyzed (e.g., by imaging) in situ in a tissue sample without migrating out of the tissue sample, e.g., onto a substrate. In some embodiments, the probe comprises the analyte-binding moiety (e.g., antibody) and the nucleic acid barcode sequence is not cleaved during the in situ analysis.

In some cases, the analysis is performed on one or more images captured, and may comprise processing the image(s) and/or quantifying signals observed. For example, the analysis may comprise processing information of one or more cell types, one or more types of biomarkers, a number or level of a biomarker, and/or a number or level of cells detected in a particular region of the sample. In some embodiments, the analysis comprises detecting a sequence e.g., a barcode present in the sample. In some embodiments, the analysis includes quantification of puncta (e.g., if amplification products are detected). In some cases, the analysis includes determining whether particular cells and/or signals are present that correlate with one or more biomarkers from a particular panel. In some embodiments, the obtained information may be compared to a positive and negative control, or to a threshold of a feature to determine if the sample exhibits a certain feature or phenotype. In some cases, the information may comprise signals from a cell, a region, and/or comprise readouts from multiple detectable labels. In some case, the analysis further includes displaying the information from the analysis or detection step. In some embodiments, software may be used to automate the processing, analysis, and/or display of data.

III. COMPOSITIONS AND KITS

In some embodiments, provided herein is a composition comprising a plurality of probes as described in Section II, such as: one or more first probes and second probes (e.g., chromatin accessing probes, detection probes), wherein the first probe hybridizes to a first nucleic acid strand in the first chromatin region and the second probe hybridizes to a second nucleic acid strand in the second chromatin region engaged in a chromatin interaction event; and, one or more bridging probes, wherein the ends of the first and/or second probes or the ends of the one or more bridging probes form a circular probe, wherein the circular probe comprises a sequence of the first nucleic acid strand or complement thereof and/or a sequence of the second nucleic acid strand or complement thereof.

Also provided herein are kits, for example comprising a probe or a library of probes (optionally comprising a detectable moiety, e.g., a signal producing tag) as described in Section II.

The various components of the kit may be present in separate containers or certain compatible components may be pre-combined into a single container. In some embodiments, the kits further contain instructions for using the components of the kit to practice the provided methods.

In some embodiments, the kits can contain reagents and/or consumables required for performing one or more steps of the provided methods. In some embodiments, the kits contain reagents for fixing, embedding, and/or permeabilizing the biological sample. In some embodiments, the kits contain reagents, such as enzymes and buffers for ligation and/or amplification, such as ligases and/or polymerases. In some aspects, the kit can also comprise any of the reagents described herein, e.g., wash buffer and ligation buffer. In some embodiments, the kits contain reagents for detection and/or sequencing, such as barcode detection probes or detectable labels. In some embodiments, the kits optionally contain other components, for example nucleic acid primers, enzymes and reagents, buffers, nucleotides, modified nucleotides, reagents for additional assays.

IV. TERMINOLOGY

Specific terminology is used throughout this disclosure to explain various aspects of the apparatus, systems, methods, and compositions that are described.

Having described some illustrative embodiments of the present disclosure, it should be apparent to those skilled in the art that the foregoing is merely illustrative and not limiting, having been presented by way of example only. Numerous modifications and other illustrative embodiments are within the scope of one of ordinary skill in the art and are contemplated as falling within the scope of the present disclosure. In particular, although many of the examples presented herein involve specific combinations of method acts or system elements, it should be understood that those acts and those elements may be combined in other ways to accomplish the same objectives.

As used herein, the term '_____', generally refers to . . . "or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. § 112, sixth paragraph.

As used herein, the singular forms "a," "an," and "the" include plural referents unless the context clearly dictates otherwise. For example, "a" or "an" means "at least one" or "one or more." It should also be understood that, unless a term is expressly defined in this patent using the sentence "

The term "about" or "approximately" as used herein refers to the usual error range for the respective value readily known to the skilled person in this technical field. Reference to "about" a value or parameter herein includes (and describes) embodiments that are directed to that value or parameter per se. For example, "about" can mean within 1 or more than 1 standard deviation, per the practice in the relevant field. Alternatively, "about" can mean a range of up to 20%, up to 10%, up to 5%, or up to 1% of a given value.

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range.

Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements. Similarly, use of a), b), etc., or i), ii), etc. does not by itself connote any priority, precedence, or order of steps in the claims. Similarly, the use of these terms in the specification does not by itself connote any required priority, precedence, or order.

(i) Barcode

A "barcode" is a label, or identifier, that conveys or is capable of conveying information (e.g., information about an analyte in a sample, a bead, and/or a capture probe). A barcode can be part of an analyte, or independent of an analyte. A barcode can be attached to an analyte. A particular barcode can be unique relative to other barcodes.

Barcodes can have a variety of different formats. For example, barcodes can include polynucleotide barcodes, random nucleic acid and/or amino acid sequences, and synthetic nucleic acid and/or amino acid sequences. A barcode can be attached to an analyte or to another moiety or structure in a reversible or irreversible manner. A barcode can be added to, for example, a fragment of a deoxyribonucleic acid (DNA) or ribonucleic acid (RNA) sample before or during sequencing of the sample. Barcodes can allow for identification and/or quantification of individual sequencing-reads (e.g., a barcode can be or can include a unique molecular identifier or "UMI").

Barcodes can spatially-resolve molecular components found in biological samples, for example, at single-cell resolution (e.g., a barcode can be or can include a "spatial barcode"). In some embodiments, a barcode includes both a UMI and a spatial barcode. In some embodiments, a barcode includes two or more sub-barcodes that together function as a single barcode. For example, a polynucleotide barcode can include two or more polynucleotide sequences (e.g., sub-barcodes) that are separated by one or more non-barcode sequences.

(ii) Nucleic Acid and Nucleotide

The terms "nucleic acid" and "nucleotide" are intended to be consistent with their use in the art and to include naturally-occurring species or functional analogs thereof. Particularly useful functional analogs of nucleic acids are capable of hybridizing to a nucleic acid in a sequence-specific fashion (e.g., capable of hybridizing to two nucleic acids such that ligation can occur between the two hybridized nucleic acids) or are capable of being used as a template for replication of a particular nucleotide sequence. Naturally-occurring nucleic acids generally have a backbone containing phosphodiester bonds. An analog structure can have an alternate backbone linkage including any of a variety of those known in the art. Naturally-occurring nucleic acids generally have a deoxyribose sugar (e.g., found in deoxyribonucleic acid (DNA)) or a ribose sugar (e.g. found in ribonucleic acid (RNA)).

A nucleic acid can contain nucleotides having any of a variety of analogs of these sugar moieties that are known in the art. A nucleic acid can include native or non-native nucleotides. In this regard, a native deoxyribonucleic acid can have one or more bases selected from the group consisting of adenine (A), thymine (T), cytosine (C), or guanine (G), and a ribonucleic acid can have one or more bases selected from the group consisting of uracil (U), adenine (A), cytosine (C), or guanine (G). Useful non-native bases that can be included in a nucleic acid or nucleotide are known in the art.

Examples of modified base moieties which can be used to modify nucleotides at any position on its structure include, but are not limited to: 5-fluorouracil, 5-bromouracil, 5-chlorouracil, 5-iodouracil, hypoxanthine, xanthine, acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, $N^-$6-sopentenyladenine, 1-methylguanine, 1-methylinosine, 2,2-dimethylguanine, 2-methyladenine, 2-methylguanine, 3-methylcytosine, 5-methyl cytosine, N6-adenine, 7-methylguanine, 5-methylaminomethyluracil, methoxyarninomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid, pseudouracil, queosine, 2-thiocytosine, 5-methyl-2-thiouracil, 2-thiouracil, 4-thiouracil, 5-methyluracil, uracil-5-oxyacetic acid methylester, uracil-S-oxyacetic acid, 5-methyl-2-thiouracil, 3-(3-amino-3-N-2-carboxypropyl) uracil, 2,6-diaminopurine and biotinylated analogs, amongst others.

Examples of modified sugar moieties which may be used to modify nucleotides at any position on its structure include, but are not limited to arabinose, 2-fluoroarabinose, xylose, and hexose, or a modified component of the phosphate backbone, such as phosphorothioate, a phosphorodithioate, a phosphoramidothioate, a phosphoramidate, a phosphordiamidate, a methylphosphonate, an alkyl phosphotriester, or a formacetal or analog thereof.

(iii) Probe and Target

A "probe" or a "target," when used in reference to a nucleic acid or sequence of a nucleic acids, is intended as a semantic identifier for the nucleic acid or sequence in the context of a method or composition, and does not limit the structure or function of the nucleic acid or sequence beyond what is expressly indicated.

(iv) Oligonucleotide and Polynucleotide

The terms "oligonucleotide" and "polynucleotide" are used interchangeably to refer to a single-stranded multimer of nucleotides from about 2 to about 500 nucleotides in length. Oligonucleotides can be synthetic, made enzymatically (e.g., via polymerization), or using a "split-pool" method. Oligonucleotides can include ribonucleotide monomers (i.e., can be oligoribonucleotides) and/or deoxyribonucleotide monomers (i.e., oligodeoxyribonucleotides). In some examples, oligonucleotides can include a combination of both deoxyribonucleotide monomers and ribonucleotide monomers in the oligonucleotide (e.g., random or ordered combination of deoxyribonucleotide monomers and ribonucleotide monomers). An oligonucleotide can be 4 to 10, 10 to 20, 21 to 30, 31 to 40, 41 to 50, 51 to 60, 61 to 70, 71 to 80, 80 to 100, 100 to 150, 150 to 200, 200 to 250, 250 to 300, 300 to 350, 350 to 400, or 400-500 nucleotides in length, for example. Oligonucleotides can include one or more functional moieties that are attached (e.g., covalently or non-covalently) to the multimer structure. For example, an oligonucleotide can include one or more detectable labels (e.g., a radioisotope or fluorophore).

(v) Hybridizing, Hybridize, Annealing, and Anneal

The terms "hybridizing," "hybridize," "annealing," and "anneal" are used interchangeably in this disclosure, and refer to the pairing of substantially complementary or complementary nucleic acid sequences within two different molecules. Pairing can be achieved by any process in which a nucleic acid sequence joins with a substantially or fully complementary sequence through base pairing to form a hybridization complex. For purposes of hybridization, two nucleic acid sequences are "substantially complementary" if at least 60% (e.g., at least 70%, at least 80%, or at least 90%) of their individual bases are complementary to one another.

(vi) Primer

A "primer" is a single-stranded nucleic acid sequence having a 3' end that can be used as a substrate for a nucleic acid polymerase in a nucleic acid extension reaction. RNA primers are formed of RNA nucleotides, and are used in RNA synthesis, while DNA primers are formed of DNA nucleotides and used in DNA synthesis. Primers can also include both RNA nucleotides and DNA nucleotides (e.g., in a random or designed pattern). Primers can also include other natural or synthetic nucleotides described herein that can have additional functionality. In some examples, DNA primers can be used to prime RNA synthesis and vice versa (e.g., RNA primers can be used to prime DNA synthesis). Primers can vary in length. For example, primers can be about 6 bases to about 120 bases. For example, primers can include up to about 25 bases. A primer, may in some cases, refer to a primer binding sequence.

(vii) Primer Extension

A "primer extension" refers to any method where two nucleic acid sequences become linked (e.g., hybridized) by an overlap of their respective terminal complementary nucleic acid sequences. Such linking can be followed by nucleic acid extension (e.g., an enzymatic extension) of one, or both termini using the other nucleic acid sequence as a template for extension. Enzymatic extension can be performed by an enzyme including, but not limited to, a polymerase and/or a reverse transcriptase.

(viii) Ligation

In some embodiments, provided herein is a probe or probe set capable of DNA-templated ligation, such as from a cDNA molecule. See, e.g., U.S. Pat. No. 8,551,710, which is hereby incorporated by reference in its entirety. In some embodiments, provided herein is a probe or probe set capable of RNA-templated ligation. See, e.g., U.S. Pat. Pub. 2020/0224244 which is hereby incorporated by reference in its entirety. In some embodiments, the probe set is a SNAIL probe set. See, e.g., U.S. Pat. Pub. 20190055594, which is hereby incorporated by reference in its entirety.

In some embodiments, the ligation herein is a proximity ligation of ligating two (or more) nucleic acid sequences that are in proximity with each other, e.g., through enzymatic means (e.g., a ligase). In some embodiments, proximity ligation can include a "gap-filling" step that involves incorporation of one or more nucleic acids by a polymerase, based on the nucleic acid sequence of a template nucleic acid molecule, spanning a distance between the two nucleic acid molecules of interest (see, e.g., U.S. Pat. No. 7,264,929, the entire contents of which are incorporated herein by reference). A wide variety of different methods can be used for proximity ligating nucleic acid molecules, including (but not limited to) "sticky-end" and "blunt-end" ligations. Additionally, single-stranded ligation can be used to perform proximity ligation on a single-stranded nucleic acid molecule. Sticky-end proximity ligations involve the hybridization of complementary single-stranded sequences between the two nucleic acid molecules to be joined, prior to the ligation event itself. Blunt-end proximity ligations generally do not include hybridization of complementary regions from each nucleic acid molecule because both nucleic acid molecules lack a single-stranded overhang at the site of ligation.

In some embodiments, provided herein is a multiplexed proximity ligation assay. See, e.g., U.S. Pat. Pub. 20140194311 which is hereby incorporated by reference in its entirety. In some embodiments, provided herein is a probe or probe set capable of proximity ligation. In some embodiments, a circular probe can be indirectly hybridized to the target nucleic acid. In some embodiments, the circular construct is formed from a probe set capable of proximity ligation, for instance a proximity ligation in situ hybridization (PLISH) probe set. See, e.g., U.S. Pat. Pub. 2020/0224243 which is hereby incorporated by reference in its entirety. In some embodiments, the probe set may comprise two or more probe oligonucleotides, each comprising a region that is complementary to each other. For detection of analytes using oligonucleotides in proximity, see, e.g., Soderberg et al., Methods. (2008), 45(3): 227-32, and U.S. Patent Application Publication No. 2002/0051986, the entire contents of which are incorporated herein by reference.

In some embodiments, the ligation involves chemical ligation. In some embodiments, the ligation involves template dependent ligation. In some embodiments, the ligation involves template independent ligation. In some embodiments, the ligation involves enzymatic ligation.

In some embodiments, the enzymatic ligation involves use of a ligase. In some aspects, the ligase used herein comprises an enzyme that is commonly used to join polynucleotides together or to join the ends of a single polynucleotide. An RNA ligase, a DNA ligase, or another variety of ligase can be used to ligate two nucleotide sequences together. Ligases comprise ATP-dependent double-strand polynucleotide ligases, NAD-i-dependent double-strand DNA or RNA ligases and single-strand polynucleotide ligases, for example any of the ligases described in EC 6.5.1.1 (ATP-dependent ligases), EC 6.5.1.2 (NAD+-dependent ligases), EC 6.5.1.3 (RNA ligases). Specific examples of ligases comprise bacterial ligases such as *E. coli* DNA ligase, Tth DNA ligase, *Thermococcus* sp. (strain 9° N) DNA ligase (9° N™ DNA ligase, New England Biolabs), Taq DNA ligase, Ampligase™ (Epicentre Biotechnologies) and phage ligases such as T3 DNA ligase, T4 DNA ligase and T7 DNA ligase and mutants thereof. In some embodiments, the ligase is a T4 RNA ligase. In some embodiments, the ligase is a splintR ligase. In some embodiments, the ligase is a single stranded DNA ligase. In some embodiments, the ligase is a T4 DNA ligase. In some embodiments, the ligase is a ligase that has an DNA-splinted DNA ligase activity. In some embodiments, the ligase is a ligase that has an RNA-splinted DNA ligase activity.

In some embodiments, the ligation herein is a direct ligation. In some embodiments, the ligation herein is an indirect ligation. "Direct ligation" means that the ends of the polynucleotides hybridize immediately adjacently to one another to form a substrate for a ligase enzyme resulting in their ligation to each other (intramolecular ligation). Alternatively, "indirect" means that the ends of the polynucleotides hybridize non-adjacently to one another, i.e., separated by one or more intervening nucleotides or "gaps". In some embodiments, said ends are not ligated directly to each other, but instead occurs either via the intermediacy of one or more intervening (so-called "gap" or "gap-filling" (oligo) nucleotides) or by the extension of the 3' end of a probe to "fill" the "gap" corresponding to said intervening nucleotides (intermolecular ligation). In some cases, the gap of one or more nucleotides between the hybridized ends of the polynucleotides may be "filled" by one or more "gap" (oligo)nucleotide(s) which are complementary to a splint, padlock probe, or target nucleic acid. The gap may be a gap of 1 to 60 nucleotides or a gap of 1 to 40 nucleotides or a gap of 3 to 40 nucleotides. In specific embodiments, the gap may be a gap of about 1, 2, 3, 4, 5, 6, 7, 8, 9 or 10 or more nucleotides, of any integer (or range of integers) of nucleotides in between the indicated values. In some embodiments, the gap between said terminal regions may be filled by a gap oligonucleotide or by extending the 3' end of a polynucleotide. In some cases, ligation involves ligating the ends of the probe to at least one gap (oligo)nucleotide, such that the gap (oligo)nucleotide becomes incorporated into the resulting polynucleotide. In some embodiments, the ligation herein is preceded by gap filling. In other embodiments, the ligation herein does not require gap filling.

In some embodiments, ligation of the polynucleotides produces polynucleotides with melting temperature higher than that of unligated polynucleotides. Thus, in some aspects, ligation stabilizes the hybridization complex containing the ligated polynucleotides prior to subsequent steps, comprising amplification and detection.

In some aspects, a high fidelity ligase, such as a thermostable DNA ligase (e.g., a Taq DNA ligase), is used. Thermostable DNA ligases are active at elevated temperatures, allowing further discrimination by incubating the ligation at a temperature near the melting temperature ($T_m$) of the DNA strands. This selectively reduces the concentration of annealed mismatched substrates (expected to have a slightly lower $T_m$ around the mismatch) over annealed fully base-paired substrates. Thus, high-fidelity ligation can be achieved through a combination of the intrinsic selectivity of the ligase active site and balanced conditions to reduce the incidence of annealed mismatched dsDNA.

(ix) Nucleic Acid Extension

A "nucleic acid extension" generally involves incorporation of one or more nucleic acids (e.g., A, G, C, T, U, nucleotide analogs, or derivatives thereof) into a molecule (such as, but not limited to, a nucleic acid sequence) in a template-dependent manner, such that consecutive nucleic acids are incorporated by an enzyme (such as a polymerase or reverse transcriptase), thereby generating a newly synthesized nucleic acid molecule. For example, a primer that hybridizes to a complementary nucleic acid sequence can be used to synthesize a new nucleic acid molecule by using the complementary nucleic acid sequence as a template for nucleic acid synthesis. Similarly, a 3' polyadenylated tail of an mRNA transcript that hybridizes to a poly (dT) sequence (e.g., capture domain) can be used as a template for single-strand synthesis of a corresponding cDNA molecule.

(x) PCR Amplification

A "PCR amplification" refers to the use of a polymerase chain reaction (PCR) to generate copies of genetic material, including DNA and RNA sequences. Suitable reagents and conditions for implementing PCR are described, for example, in U.S. Pat. Nos. 4,683,202, 4,683,195, 4,800,159, 4,965,188, and 5,512,462, the entire contents of each of which are incorporated herein by reference. In a typical PCR amplification, the reaction mixture includes the genetic material to be amplified, an enzyme, one or more primers that are employed in a primer extension reaction, and reagents for the reaction. The oligonucleotide primers are of sufficient length to provide for hybridization to complementary genetic material under annealing conditions. The length of the primers generally depends on the length of the amplification domains, but will typically be at least 4 bases, at least 5 bases, at least 6 bases, at least 8 bases, at least 9 bases, at least 10 base pairs (bp), at least 11 bp, at least 12 bp, at least 13 bp, at least 14 bp, at least 15 bp, at least 16 bp, at least 17 bp, at least 18 bp, at least 19 bp, at least 20 bp, at least 25 bp, at least 30 bp, at least 35 bp, and can be as long as 40 bp or longer, where the length of the primers will generally range from 18 to 50 bp. The genetic material can be contacted with a single primer or a set of two primers (forward and reverse primers), depending upon whether primer extension, linear or exponential amplification of the genetic material is desired.

In some embodiments, the PCR amplification process uses a DNA polymerase enzyme. The DNA polymerase activity can be provided by one or more distinct DNA polymerase enzymes. In certain embodiments, the DNA polymerase enzyme is from a bacterium, e.g., the DNA polymerase enzyme is a bacterial DNA polymerase enzyme. For instance, the DNA polymerase can be from a bacterium of the genus *Escherichia, Bacillus, Thermophilus*, or *Pyrococcus*.

Suitable examples of DNA polymerases that can be used include, but are not limited to: *E. coli* DNA polymerase I, Bsu DNA polymerase, Bst DNA polymerase, Taq DNA polymerase, VENT™ DNA polymerase, DEEPVENT™ DNA polymerase, LongAmp® Taq DNA polymerase, LongAmp® Hot Start Taq DNA polymerase, Crimson LongAmp® Taq DNA polymerase, Crimson Taq DNA polymerase, OneTaq® DNA polymerase, OneTaq® QuickLoad® DNA polymerase, Hemo KlenTaq® DNA polymerase, REDTaq® DNA polymerase, Phusion® DNA polymerase, Phusion® High-Fidelity DNA polymerase, Platinum Pfx DNA polymerase, AccuPrime Pfx DNA polymerase, Phi29 DNA polymerase, Klenow fragment, Pwo DNA polymerase, Pfu DNA polymerase, T4 DNA polymerase and T7 DNA polymerase enzymes.

The term "DNA polymerase" includes not only naturally-occurring enzymes but also all modified derivatives thereof, including also derivatives of naturally-occurring DNA polymerase enzymes. For instance, in some embodiments, the DNA polymerase can have been modified to remove 5'-3' exonuclease activity. Sequence-modified derivatives or mutants of DNA polymerase enzymes that can be used include, but are not limited to, mutants that retain at least some of the functional, e.g. DNA polymerase activity of the wild-type sequence. Mutations can affect the activity profile of the enzymes, e.g. enhance or reduce the rate of polymerization, under different reaction conditions, e.g. temperature, template concentration, primer concentration, etc. Mutations or sequence-modifications can also affect the exonuclease activity and/or thermostability of the enzyme.

In some embodiments, PCR amplification can include reactions such as, but not limited to, a strand-displacement amplification reaction, a rolling circle amplification reaction, a ligase chain reaction, a transcription-mediated amplification reaction, an isothermal amplification reaction, and/or a loop-mediated amplification reaction.

In some embodiments, PCR amplification uses a single primer that is complementary to the 3' tag of target DNA fragments. In some embodiments, PCR amplification uses a first and a second primer, where at least a 3' end portion of the first primer is complementary to at least a portion of the 3' tag of the target nucleic acid fragments, and where at least a 3' end portion of the second primer exhibits the sequence of at least a portion of the 5' tag of the target nucleic acid fragments. In some embodiments, a 5' end portion of the first primer is non-complementary to the 3' tag of the target nucleic acid fragments, and a 5' end portion of the second primer does not exhibit the sequence of at least a portion of the 5' tag of the target nucleic acid fragments. In some embodiments, the first primer includes a first universal sequence and/or the second primer includes a second universal sequence.

In some embodiments (e.g., when the PCR amplification amplifies captured DNA), the PCR amplification products can be ligated to additional sequences using a DNA ligase enzyme. The DNA ligase activity can be provided by one or more distinct DNA ligase enzymes. In some embodiments, the DNA ligase enzyme is from a bacterium, e.g., the DNA ligase enzyme is a bacterial DNA ligase enzyme. In some embodiments, the DNA ligase enzyme is from a virus (e.g., a bacteriophage). For instance, the DNA ligase can be T4 DNA ligase. Other enzymes appropriate for the ligation step include, but are not limited to, Tth DNA ligase, Taq DNA ligase, *Thermococcus* sp. (strain 9oN) DNA ligase (9oN™ DNA ligase, available from New England Biolabs, Ipswich, Mass.), and Ampligase™ (available from Epicentre Biotechnologies, Madison, Wis.). Derivatives, e.g. sequence-modified derivatives, and/or mutants thereof, can also be used.

In some embodiments, genetic material is amplified by reverse transcription polymerase chain reaction (RT-PCR). The desired reverse transcriptase activity can be provided by one or more distinct reverse transcriptase enzymes, suitable examples of which include, but are not limited to: M-MLV, MuLV, AMV, HIV, ArrayScript™, MultiScribe™ ThermoScript™, and SuperScript® I, II, III, and IV enzymes. "Reverse transcriptase" includes not only naturally occurring enzymes, but all such modified derivatives thereof, including also derivatives of naturally-occurring reverse transcriptase enzymes.

In addition, reverse transcription can be performed using sequence-modified derivatives or mutants of M-MLV, MuLV, AMV, and HIV reverse transcriptase enzymes, including mutants that retain at least some of the functional, e.g. reverse transcriptase, activity of the wild-type sequence. The reverse transcriptase enzyme can be provided as part of a composition that includes other components, e.g. stabilizing components that enhance or improve the activity of the reverse transcriptase enzyme, such as RNase inhibitor(s), inhibitors of DNA-dependent DNA synthesis, e.g. actinomycin D. Many sequence-modified derivative or mutants of reverse transcriptase enzymes, e.g. M-MLV, and compositions including unmodified and modified enzymes are commercially available, e.g. ArrayScript™, MultiScribe™ ThermoScript™, and SuperScript® I, II, III, and IV enzymes.

Certain reverse transcriptase enzymes (e.g. Avian Myeloblastosis Virus (AMV) Reverse Transcriptase and Moloney Murine Leukemia Virus (M-MuLV, MMLV) Reverse Transcriptase) can synthesize a complementary DNA strand using both RNA (cDNA synthesis) and single-stranded DNA (ssDNA) as a template. Thus, in some embodiments, the reverse transcription reaction can use an enzyme (reverse transcriptase) that is capable of using both RNA and ssDNA as the template for an extension reaction, e.g. an AMV or MMLV reverse transcriptase.

In some embodiments, the quantification of RNA and/or DNA is carried out by real-time PCR (also known as quantitative PCR or qPCR), using techniques well known in the art, such as but not limited to "TAQMAN™" or "SYBR®", or on capillaries ("LightCycler® Capillaries"). In some embodiments, the quantification of genetic material is determined by optical absorbance and with real-time PCR. In some embodiments, the quantification of genetic material is determined by digital PCR. In some embodiments, the genes analyzed can be compared to a reference nucleic acid extract (DNA and RNA) corresponding to the expression (mRNA) and quantity (DNA) in order to compare expression levels of the target nucleic acids.

(xi) Label, Detectable Label, and Optical Label

The terms "detectable label," "optical label," and "label" are used interchangeably herein to refer to a directly or indirectly detectable moiety that is associated with (e.g., conjugated to) a molecule to be detected, e.g., a probe for in situ assay, a capture probe or analyte. The detectable label can be directly detectable by itself (e.g., radioisotope labels or fluorescent labels) or, in the case of an enzymatic label, can be indirectly detectable, e.g., by catalyzing chemical alterations of a substrate compound or composition, which substrate compound or composition is directly detectable. Detectable labels can be suitable for small scale detection and/or suitable for high-throughput screening. As such, suitable detectable labels include, but are not limited to, radioisotopes, fluorophores, chemiluminescent compounds, bioluminescent compounds, and dyes.

The detectable label can be qualitatively detected (e.g., optically or spectrally), or it can be quantified. Qualitative detection generally includes a detection method in which the existence or presence of the detectable label is confirmed, whereas quantifiable detection generally includes a detection method having a quantifiable (e.g., numerically reportable) value such as an intensity, duration, polarization, and/or other properties. In some embodiments, the detectable label is bound to a feature or to a capture probe associated with a feature. For example, detectably labeled features can include a fluorescent, a colorimetric, or a chemiluminescent label attached to a bead (see, for example, Rajeswari et al., *J. Microbiol Methods* 139:22-28, 2017, and Forcucci et al., *J. Biomed Opt.* 10:105010, 2015, the entire contents of each of which are incorporated herein by reference).

In some embodiments, a plurality of detectable labels can be attached to a feature, capture probe, or composition to be detected. For example, detectable labels can be incorporated during nucleic acid polymerization or amplification (e.g., Cy5®-labelled nucleotides, such as Cy5®-dCTP). Any suitable detectable label can be used. In some embodiments, the detectable label is a fluorophore. For example, the fluorophore can be from a group that includes: 7-AAD (7-Aminoactinomycin D), Acridine Orange (+DNA), Acridine Orange (+RNA), Alexa Fluor® 350, Alexa Fluor® 430, Alexa Fluor® 488, Alexa Fluor® 532, Alexa Fluor® 546, Alexa Fluor® 555, Alexa Fluor® 568, Alexa Fluor® 594, Alexa Fluor® 633, Alexa Fluor® 647, Alexa Fluor® 660, Alexa Fluor® 680, Alexa Fluor® 700, Alexa Fluor® 750, Allophycocyanin (APC), AMCA/AMCA-X, 7-Aminoactinomycin D (7-AAD), 7-Amino-4-methylcoumarin, 6-Aminoquinoline, Aniline Blue, ANS, APC-Cy7, ATTO-TAG™ CBQCA, ATTO-TAG™ FQ, Auramine O-Feulgen, BCECF (high pH), BFP (Blue Fluorescent Protein), BFP/GFP FRET, BOBO™-1/BO-PRO™-1, BOBO™-3/BO-PRO™-3, BODIPY® FL, BODIPY® TMR, BODIPY® TR-X, BODIPY® 530/550, BODIPY® 558/568, BODIPY® 564/570, BODIPY® 581/591, BODIPY® 630/650-X, BODIPY® 650-665-X, BTC, Calcein, Calcein Blue, Calcium Crimson™, Calcium Green-1™, Calcium Orange™, Calcofluor® White, 5-Carboxyfluoroscein (5-FAM), 5-Carboxynaphthofluoroscein, 6-Carboxyrhodamine 6G, 5-Carboxytetramethylrhodamine (5-TAMRA), Carboxy-X-rhodamine (5-ROX), Cascade Blue®, Cascade Yellow™, CCF2 (GeneBLAzer™), CFP (Cyan Fluorescent Protein), CFP/YFP FRET, Chromomycin A3, Cl-NERF (low pH), CPM, 6-CR 6G, CTC Formazan, Cy2®, Cy3®, Cy3.5®, Cy5®, Cy5.5®, Cy7®, Cychrome (PE-Cy5), Dansylamine, Dansyl cadaverine, Dansylchloride, DAPI, Dapoxyl, DCFH, DHR, DiA (4-Di-16-ASP), DiD (DiC18 (5)), DIDS, DiI (DiC18(3)), DiO (DiOC18(3)), DiR (DilC18 (7)), Di-4 ANEPPS, Di-8 ANEPPS, DM-NERF (4.5-6.5 pH), DsRed (Red Fluorescent Protein), EBFP, ECFP, EGFP, ELF®-97 alcohol, Eosin, Erythrosin, Ethidium bromide, Ethidium homodimer-1 (EthD-1), Europium (III) Chloride, 5-FAM (5-Carboxyfluorescein), Fast Blue, Fluorescein-dT phosphoramidite, FITC, Fluo-3, Fluo-4, FluorX®, Fluoro-Gold™ (high pH), Fluoro-Gold™ (low pH), Fluoro-Jade, FM® 1-43, Fura-2 (high calcium), Fura-2/BCECF, Fura Red™ (high calcium), Fura Red™/Fluo-3, GeneBLAzer™ (CCF2), GFP Red Shifted (rsGFP), GFP Wild Type, GFP/BFP FRET, GFP/DsRed FRET, Hoechst 33342 & 33258, 7-Hydroxy-4-methylcoumarin (pH 9), 1,5 IAEDANS, Indo-1 (high calcium), Indo-1 (low calcium), Indodicarbocyanine, Indotricarbocyanine, JC-1, 6-JOE, JOJO™-1/JO-PRO™-1, LDS 751 (+DNA), LDS 751 (+RNA), LOLO™-1/LO-PRO™-1, *Lucifer* Yellow, LysoSensor™ Blue (pH 5), LysoSensor™ Green (pH 5), LysoSensor™ Yellow/Blue (pH 4.2), LysoTracker® Green, LysoTracker® Red, LysoTracker® Yellow, Mag-Fura-2, Mag-Indo-1, Magnesium Green™, Marina Blue®, 4-Methylumbelliferone, Mithramycin, MitoTracker® Green, MitoTracker® Orange, MitoTracker® Red, NBD (amine), Nile Red, Oregon Green® 488, Oregon Green® 500, Oregon Green® 514, Pacific Blue, PBF1, PE (R-phycoerythrin), PE-Cy5, PE-Cy7, PE-Texas Red, PerCP (Peridinin chlorphyll protein), PerCP-Cy5.5 (TruRed), PharRed (APC-Cy7), C-phycocyanin, R-phycocyanin, R-phycoerythrin (PE), PI (Propidium Iodide), PKH26, PKH67, POPO™-1/PO-PRO™-1, POPO™-3/PO-PRO™-3, Propidium Iodide (PI), PyMPO, Pyrene, Pyronin Y, Quantam Red (PE-Cy5), Quinacrine Mustard, R670 (PE-Cy5), Red 613 (PE-Texas Red), Red Fluorescent Protein (DsRed), Resorufin, RH 414, Rhod-2, Rhodamine B, Rhodamine Green™, Rhodamine Red™, Rhodamine Phalloidin, Rhodamine 110, Rhodamine 123, 5-ROX (carboxy-X-rhodamine), S65A, S65C, S65L, S65T, SBFI, SITS, SNAFL®-1 (high pH), SNAFL®-2, SNARF®-1 (high pH), SNARF®-1 (low pH), Sodium Green™, SpectrumAqua®, SpectrumGreen® #1, SpectrumGreen® #2, SpectrumOrange®, SpectrumRed, SYTO 11, SYTO® 13, SYTO® 17, SYTO® 45, SYTOX® Blue, SYTOX® Green, SYTOX® Orange, 5-TAMRA (5-Carboxytetramethylrhodamine), Tetramethylrhodamine (TRITC), Texas Red®/Texas Red®-X, Texas Red®-X (NHS Ester), Thiadicarbocyanine, Thiazole Orange, TOTO®-1/TO-PRO®-1, TOTO®-3/TO-PRO®-3, TO-PRO-5, Tricolor (PE-Cy5), TRITC (Tetramethylrhodamine), TruRed (PerCP-Cy5.5), WW 781, X-Rhodamine (XRITC), Y66F, Y66H, Y66W, YFP (Yellow Fluorescent Protein), YOYO®-1/YO-PRO®-1, YOYO®-3/YO-PRO®-3, 6-FAM (Fluorescein), 6-FAM (NHS Ester), 6-FAM (Azide), HEX, TAMRA (NHS Ester), Yakima Yellow, MAX, TET, TEX615, ATTO 488, ATTO 532, ATTO 550, ATTO 565, ATTO Rho101, ATTO 590, ATTO 633, ATTO 647N, TYE 563, TYE 665, TYE 705, 5' IRDye® 700, 5' IRDye® 800, 5' IRDye® 800CW (NHS Ester), WellRED D4 Dye, WellRED D3 Dye, WellRED D2 Dye, Lightcycler® 640 (NHS Ester), and Dy 750 (NHS Ester).

As mentioned above, in some embodiments, a detectable label is or includes a luminescent or chemiluminescent moiety. Common luminescent/chemiluminescent moieties include, but are not limited to, peroxidases such as horseradish peroxidase (HRP), soybean peroxidase (SP), alkaline phosphatase, and luciferase. These protein moieties can catalyze chemiluminescent reactions given the appropriate substrates (e.g., an oxidizing reagent plus a chemiluminescent compound. A number of compound families are known to provide chemiluminescence under a variety of conditions. Non-limiting examples of chemiluminescent compound families include 2,3-dihydro-1,4-phthalazinedione luminol, 5-amino-6,7,8-trimethoxy- and the dimethylamino[ca]benz analog. These compounds can luminesce in the presence of alkaline hydrogen peroxide or calcium hypochlorite and base. Other examples of chemiluminescent compound families include, e.g., 2,4,5-triphenylimidazoles, para-dimethylamino and -methoxy substituents, oxalates such as oxalyl active esters, p-nitrophenyl, N-alkyl acridinum esters, luciferins, lucigenins, or acridinium esters. In some embodiments, a detectable label is or includes a metal-based or mass-based label. For example, small cluster metal ions, metals, or semiconductors may act as a mass code. In some examples, the metals can be selected from Groups 3-15 of the periodic table, e.g., Y, La, Ag, Au, Pt, Ni, Pd, Rh, Ir, Co, Cu, Bi, or a combination thereof.

(xii) Subject

As used herein, the term "subject", generally refers to an animal, such as a mammal (e.g., human) or avian (e.g., bird), or other organism, such as a plant. For example, the subject can be a vertebrate, a mammal, a rodent (e.g., a mouse), a primate, a simian or a human. Animals may include, but are not limited to, farm animals, sport animals, and pets. A subject can be a healthy or asymptomatic individual, an individual that has or is suspected of having a disease (e.g., cancer) or a pre-disposition to the disease, and/or an individual that is in need of therapy or suspected of needing therapy. A subject can be a patient. A subject can be a microorganism or microbe (e.g., bacteria, fungi, archaea, viruses).

V. EXEMPLARY EMBODIMENTS

Among the provided embodiments are:

Embodiment 1. A method for spatial analysis of chromatin interaction events in situ, the method comprising:
 a) obtaining a biological sample;
 b) hybridizing a first set of probes comprising at least two unique oligonucleotide sequences to a sense or antisense strand of at least two primary target nucleic acid sequences, wherein said at least two primary target nucleic acid sequences are engaged in a chromatin interaction event;
 c) hybridizing a second set of probes comprising at least two unique oligonucleotide sequences to a sense or antisense strand of said at least two primary target nucleic acid sequences;
 d) hybridizing a third set of probes to said second set of probes, wherein said second set of probes are spatially proximate to one another due to being hybridized to the at least two primary target nucleic acid sequences engaged in the chromatin interaction event and wherein said third set of probes bridge the ends of said second set of probes;
 e) extending the third set of probes to form a circularized nucleic acid comprising at least a portion of the at least two primary target nucleic acid sequences engaged in a chromatin interaction event;
 f) amplifying said circular nucleic acid to generate a population of amplicons comprising signal producing tags detectable in situ; and
 g) detecting said population of tagged amplicons in situ by said signal producing tags.

Embodiment 2. The method of Embodiment 1, further comprising the step of preparing a carrier substrate comprising said biological sample.

Embodiment 3. The method of Embodiment 2, wherein said carrier substrate is a slide having a biological sample thereon.

Embodiment 4. The method of Embodiment 1, wherein said biological sample is fixed by a fixative.

Embodiment 5. The method of Embodiment 4, wherein said biological sample is not fixed.

Embodiment 6. The method of any of Embodiments 1-5, further comprising the step of cross-linking chromatin DNA within said biological sample to chromatin associated factors with a cross-linking agent.

Embodiment 7. The method of Embodiment 6, wherein said cross-linking agent is selected from the group comprising formaldehyde, UV radiation, glutaraldehyde, bis(imido esters), bis(succinimidyl esters), diisocyanates, diacid chlorides, 1-Ethyl-3-(3-dimethylaminopropyl)carbodiimide, mitomycin C, nitrogen mustard, melphalan, 1,3-butadiene diepoxide, cis diaminedichloroplatinum(II), cyclophosphamide, disuccinimidylglutarate, and dithiobis-succinimidyl propionate.

Embodiment 8. The method of any of Embodiments 1-7, wherein said at least two primary target nucleic acid sequences comprise regulatory elements.

Embodiment 9. The method of Embodiment 8, wherein said regulatory elements are selected from the group comprising promoters, enhancers, silencers or insulators.

Embodiment 10. The method of Embodiment 9, wherein one of said first set of probes and one of said second set of probes hybridize to the target promoter DNA sequence and wherein one of said first set of probes and one of said second set of probes hybridize to the target enhancer DNA sequence.

Embodiment 11. The method of any of Embodiments 1-10, wherein said first set of probes comprise peptide nucleic acid probes.

Embodiment 12. The method of any of Embodiments 1-11, wherein said second set of probes comprise detection probes comprising 3' and 5' overhangs.

Embodiment 13. The method of any of Embodiments 1-12, wherein said third set of probes comprise complementary sequences to said 3' and 5' overhangs of said second set of probes and hybridize to the same to form said bridge.

Embodiment 14. The method of any of Embodiments 1-13, wherein step e) comprises use of DNA polymerase to extend the third set of probes.

Embodiment 15. The method of any of Embodiments 1-14, wherein said amplifying step is carried out by rolling circle amplification.

Embodiment 16. The method of any of Embodiments 1-14, wherein said amplifying step further comprises chemically labeling said amplicon.

Embodiment 17. The method of Embodiment 16, wherein said amplifying step further comprises chemically labeling said amplicon with fluorescently labeled probes.

Embodiment 18. The method of any of Embodiments 1-17, wherein said detection step comprises fluorescence microscopy.

Embodiment 19. The method of any of Embodiments 1-17, wherein said detection step comprises fluorescence in situ hybridization.

Embodiment 20. The method of any of Embodiments 1-19, wherein said chromatin associated factors comprise proteins, DNA, RNA, small molecules, and metabolites.

Embodiment 21. The method of Embodiment 20, wherein said chromatin associated factors comprise transcription factors.

Embodiment 22. The method of any of Embodiments 1-21, further comprising the steps of: quenching the signal generated from said signal producing tags; and repeating steps b)-g) wherein said first and second sets of probes each comprise at least two unique oligonucleotide sequences that hybridize to a sense or antisense strand of at least two secondary target nucleic acid sequences engaged in a chromatin interaction event.

Embodiment 23. The method of any of Embodiments 1-21 further comprising the steps of: quenching the signal from said signal producing tags; and repeating steps b)-g) for a number of successive rounds wherein each successive round comprises a first and second set of probes with different oligonucleotide sequences than the first and second set of probes used in other rounds and wherein the first and second set of probes hybridize to different target nucleic acid sequences than the target nucleic acid sequences in other rounds.

Embodiment 24. A method for spatial analysis of chromatin interaction events in situ, the method comprising: obtaining a biological sample; hybridizing a first oligonucleotide set comprising at least two unique oligonucleotide sequences to a first strand of at least two target nucleic acid sequences, wherein said at least two target nucleic acid sequences are engaged in a chromatin interaction event; hybridizing a second oligonucleotide set to said first oligonucleotide set, wherein said first oligonucleotides are proximate to one another due to being hybridized to at least two target nucleic acid sequences engaged in a chromatin interaction event and wherein said second oligonucleotides bridge the ends of said first oligonucleotides; extending the second oligonucleotides to form a circular oligonucleotide comprising at least a portion of the at least two target nucleic acid sequences engaged in a chromatin interaction event; amplifying said circular oligonucleotide to generate a population of amplicons detectable in situ; and detecting said amplicon in situ.

Embodiment 25. The method of Embodiment 24, further comprising the step of preparing a carrier substrate comprising said biological sample.

Embodiment 26. The method of Embodiment 25, wherein said carrier substrate is a slide having a biological sample thereon.

Embodiment 27. The method of any of Embodiments 24-26, wherein said biological sample is fixed by a fixative.

Embodiment 28. The method of any of Embodiments 24-26, wherein said biological sample is not fixed.

Embodiment 29. The method of Embodiment 24, cross-linking chromatin within a tissue sample to chromatin associated factors by a cross-linking agent.

Embodiment 30. The method of Embodiment 29, wherein said cross-linking agent is selected from the group comprising formaldehyde, UV radiation, glutaraldehyde, bis(imido esters), bis(succinimidyl esters), diisocyanates, diacid chlorides, 1-Ethyl-3-(3-dimethylaminopropyl)carbodiimide, mitomycin C, nitrogen mustard, melphalan, 1,3-butadiene diepoxide, cis diaminedichloroplatinum(II), cyclophosphamide, disuccinimidylglutarate, and dithiobis-succinimidyl propionate.

Embodiment 31. The method of any of Embodiments 24-30, wherein said at least two primary target nucleic acid sequences comprise regulatory elements.

Embodiment 32. The method of Embodiment 31, wherein said regulatory elements are selected from the group comprising promoters, enhancers, silencers or insulators.

Embodiment 33. The method of Embodiment 32, wherein one of said first oligonucleotides hybridizes to the target promoter DNA sequence and one of said first oligonucleotides hybridizes to the target enhancer DNA sequence.

Embodiment 34. The method of any of Embodiments 24-33, wherein said first oligonucleotides comprise detection probes comprising 3' and 5' overhangs.

Embodiment 35. The method of any of Embodiments 24-34, wherein said second oligonucleotides comprise complementary sequences to said 3' and 5' overhangs of said first oligonucleotides and hybridize to the same to form said bridge.

Embodiment 36. The method of any of Embodiments 24-35, wherein said amplifying step is carried out by rolling circle amplification.

Embodiment 37. The method of any of Embodiments 24-36, wherein said amplifying step further comprises chemically labeling said amplicon.

Embodiment 38. The method of any of Embodiments 24-37, wherein said amplifying step further comprises chemically labeling said amplicon with fluorescently labeled probes.

Embodiment 39. The method of any of Embodiments 24-38, wherein said detecting step comprises fluorescence microscopy.

Embodiment 40. The method of any of Embodiments 24-39, wherein said detecting step comprises fluorescence in situ hybridization.

Embodiment 41. The method of any of Embodiments 24-40, wherein said chromatin associated factors comprise proteins, DNA, RNA, small molecules, and metabolites.

Embodiment 42. The method of Embodiment 41, wherein said chromatin associated factors comprise transcription factors.

Embodiment 43. The method of any of Embodiments 24-42, wherein a DNA polymerase is used to extend the second oligonucleotides.

Embodiment 44. A method for spatial analysis of chromatin interaction events in situ, the method comprising:
a) obtaining a biological sample;
b) hybridizing a plurality of probes to a plurality of primary target nucleic acid sequences in situ engaged in a chromatin interaction events, wherein said plurality of probes comprise at least detection probes that hybridize to circularizing probes;
c) optionally hybridizing a second set of probes comprising at least two unique oligonucleotide sequences to a sense or antisense strand of said at least two primary target nucleic acid sequences;
d) extending the circularizing probes to form circularized nucleic acids comprising at least a portion of the primary target nucleic acid sequences engaged in a chromatin interaction event;
e) amplifying said circular nucleic acids to generate one or more populations of amplicons, each said population of amplicons comprising a signal producing tag detectable in situ; and
f) detecting said populations of tagged amplicons in situ by said signal producing tags.

Embodiment 45. The method of Embodiment 44, wherein said signal producing tags are unique to one or more populations of amplicons and capable of distinguishing one population from another.

Embodiment 46. The method of Embodiment 44 or 45, further comprising the step of sequencing said one or more populations of amplicons by in situ sequencing.

Embodiment 47. The method of any of Embodiments 44-46, further comprising the step of preparing a carrier substrate comprising said biological sample.

Embodiment 48. The method of Embodiment 47, wherein said carrier substrate is a slide having a biological sample thereon.

Embodiment 49. The method of any of Embodiments 44-48, wherein said biological sample is fixed by a fixative.

Embodiment 50. The method of any of Embodiments 44-48, wherein said biological sample is not fixed.

Embodiment 51. The method of any of Embodiments 44-50, further comprising the step of cross-linking chromatin within said biological sample to chromatin associated factors with a cross-linking agent;

Embodiment 52. The method of Embodiment 51, wherein said cross-linking agent is selected from the group comprising formaldehyde, UV radiation, glutaraldehyde, bis(imido esters), bis(succinimidyl esters), diisocyanates, diacid chlorides, 1-Ethyl-3-(3-dimethylaminopropyl)carbodiimide, mitomycin C, nitrogen mustard, melphalan, 1,3-butadiene diepoxide, cis diaminedichloroplatinum(II), cyclophosphamide, disuccinimidylglutarate, and dithiobis-succinimidyl propionate.

Embodiment 53. The method of any of Embodiments 44-52, wherein said primary target nucleic acid sequences comprise regulatory elements.

Embodiment 54. The method of any of Embodiments 44-53, wherein said regulatory elements are selected from the group comprising promoters, enhancers, silencers or insulators.

Embodiment 55. The method of any of Embodiments 44-54, wherein said primary target nucleic acid sequences comprise genomic DNA.

Embodiment 56. The method of any of Embodiments 44-55, wherein said amplifying step is carried out by rolling circle amplification.

Embodiment 57. The method of any of Embodiments 44-56, wherein said amplifying step further comprises chemically labeling said amplicon.

Embodiment 58. The method of any of Embodiments 44-57, wherein said amplifying step further comprises chemically labeling said amplicon with fluorescently labeled probes.

Embodiment 59. The method of any of Embodiments 44-58, wherein said detecting step comprises fluorescence microscopy.

Embodiment 60. The method of any of Embodiments 44-59, wherein said detecting step comprises fluorescence in situ hybridization.

Embodiment 61. The method of any of Embodiments 44-60, wherein said chromatin associated factors are selected from the group comprising proteins, DNA, RNA, small molecules, or metabolites.

Embodiment 62. The method of Embodiment 61, wherein said chromatin associated factors comprise transcription factors.

Embodiment 63. The method of Embodiment 44, wherein a DNA polymerase is used to extend the circularizing probes.

EXAMPLES

The following example is included for illustrative purposes only and is not intended to limit the scope of the present disclosure.

Example 1: Mapping Chromatin Interactions in a Mouse Cortex In Situ

The three-dimensional conformation of DNA within a cell's nucleus plays an important role in the regulation of expression of several genomic regions, including promoters and enhancers. This example demonstrates a method for determining the spatial context of chromatin interactions in situ in the mouse cortex. In particular, this example demonstrates that by using a modified version of Hi-C (Belton et al., 2012; Lieberman-Aiden et al., 2009), a tool that can help study these interactions, to obtain a spatial context as previously described and as claimed, topology of the genomes can be mapped.

Synj1 is a gene whose aberrant expression levels have been observed in Parkinson's disease. Hmox2 is a gene involved in iron metabolism. It has been previously established that brain iron metabolism experiences dysfunction during Parkinson's disease (Jiang, Wang, Rogers, & Xie, 2017). It has also been shown through Hi-C experiments that Synj1 and Hmox2 are genomic regions that are not only co-expressed, but also interact with each other regularly within the mouse cortex (Babaei et al., 2015). The assay described above are used to see the spatial distribution of the interactive patterns of the two genes within the mouse cortex tissue to increase understanding of the pathways and mechanisms involved in Parkinson's disease.

| Gene | Transcript | Probe sequence | SEQ ID NO. |
|---|---|---|---|
| Synj1 | NM_001045515.1 | ACCAAAGTGTGCAAACTGCC | 1 |
| Hmox2 | NM_010442.2 | GAACCCAGTCTATGCCCCAC | 2 |

Similarly, Dyrk1a produces a kinase that phosphorylates both amyloid precursor protein (APP) and tau. Dyrk1a has been found to be upregulated in the post-mortem brains of Alzheimer's patients (Velazquez et al., 2019). Sidt1 is a gene that encodes for transmembrane family proteins and is believed to have potential role in neurodegenerative disorders such as Alzheimer's and Parkinson's disease (Hwang et al., 2010). Dyrk1a and Sidt1 are two genes which are co-expressed and physically interact with each other in the three-dimensional conformation of the genome.

| Gene | Transcript | Probe sequence | SEQ ID NO. |
|---|---|---|---|
| Dyrk1a | NM_007890.2 | AGCCTGAATCGAGCAGAACC | 3 |
| Sidt1 | NM_198034.3 | CCCAGCATGTAGGAGGCAAA | 4 |

Example 2: Mapping Chromatin Interactions in a Human Cell Line In Situ

The three-dimensional conformation of DNA within a cell's nucleus plays an important role in the regulation of expression of several genomic regions, including promoters and enhancers. This example demonstrates a method for mapping chromatin interactions in the Human Aortic Smooth Muscle Cell (HASMC) line.

CD52 is a gene that is expressed in both normal as well as malignant immune cells, and is believed to be involved in the migration and activation of T-cells (Toh, Kyaw, Tipping, & Bobik, 2013). Despite its alleged importance in the immune system, it's biological role and mechanism are still unknown in other cells. Through previous Hi-C experiments, it has been seen that the expression of the CD52 promoter is influenced by its interactions with genomic regions known as enhancers. The interaction of CD52 with its enhancer (chr1: 26615350-26617509) has been observed in human cell lines, such as HASMC, and is conditionally expressed. Using the assays described above are useful to see the distribution of the interaction across different cell types and what spatial influences determines this expression.

| Genomic region | Transcript | Probe sequence | SEQ ID NO. |
|---|---|---|---|
| Promoter: CD52_26644410 | NM_001803 | GTCTCAGCCTTAGCCCTGTG | 5 |
| Interacting enhancer: chr1: 26615350-26617509 | — | GCCTCTTCTTAGACGACCTG TGACGAACCC | 6 |

Similarly, the assays described above are used to compare such an interaction with another interaction that is ubiquitously present throughout the tissue and is highly conserved (De Bie et al., 2006). COMMD6 gene produces NF-kappa-B (responsible for controls transcription of DNA, cytokine production and cell survival)-inhibiting proteins and studying the pathways they are involved in can lead to the identification of novel candidate genes for several metabolic disorders.

| Genomic region | Transcript | Probe sequence | SEQ ID NO. |
|---|---|---|---|
| Promoter: COMMD6_76123575 | NM_001287394 | TCGTCTTTCCAA CTCTGCGT | 7 |
| Interacting enhancer: chr13: 76119844-76120980 | — | CACCCCCTGAAG TTATGGGGCGAC | 8 |

CITATIONS

1. Ali et al. (2014). Rolling circle amplification: A versatile tool for chemical biology, materials science and medicine. *Chemical Society Reviews. Royal Society of Chemistry.* https://doi.org/10.1039/c3cs60439j
2. Babaei et al. (2015). Hi-C Chromatin Interaction Networks Predict Co-expression in the Mouse Cortex. *PLOS Computational Biology,* 11(5), e1004221. https://doi.org/10.1371/journal.pcbi.1004221
3. Belton et al. (2012). Hi-C: A comprehensive technique to capture the conformation of genomes. *Methods,* 58(3), 268-276. https://doi.org/10.1016/j.ymeth.2012.05.001
4. Bienko et al. (2013). A versatile genome-scale PCR-based pipeline for high-definition DNA FISH. *Nature Methods,* 10(2), 122-124. https://doi.org/10.1038/nmeth.2306
5. Broude et al. (1999). PNA Openers as a Tool for Direct Quantification of Specific Targets in Duplex DNA, Journal of Biomolecular Structure and Dynamics, 17(2), 237-244. https://doi.org/10.1080/07391102.1999. Ser. No. 10/508,356
6. De Bie et al. (2006). Characterization of COMMD protein-protein interactions in NF-κB signalling. *Biochemical Journal,* 398(1), 63-71. https://doi.org/10.1042/BJ20051664
7. Hwang et al. (2010). Glycoproteomics in neurodegenerative diseases. *Mass Spectrometry Reviews,* 29(1), 79-125. https://doi.org/10.1002/mas.20221
8. Jiang et al. (2017, May 1). Brain Iron Metabolism Dysfunction in Parkinson's Disease. *Molecular Neurobiology.* Humana Press Inc. https://doi.org/10.1007/s2035-016-9879-1
9. Ke et al. (2013). In situ sequencing for RNA analysis in preserved tissue and cells. *Nature Methods,* 10(9), 857-860. https://doi.org/0.1038/nmeth.2563
10. Klaesson et al. (2018). Improved efficiency of in situ protein analysis by proximity ligation using UnFold probes. *Scientific Reports,* 8(1), 5400. https://doi.org/10.1038/s41598-018-23582-1
11. Kuhn, H. (2002). Rolling-circle amplification under topological constraints. *Nucleic Acids Research,* 30(2), 574-580. https://doi.org/10.1093/nar/30.2.574
12. Lieberman-Aiden et al. (2009). Comprehensive mapping of long-range interactions reveals folding principles of the human genome. *Science,* 326(5950), 289-293. https://doi.org/10.1126/science.1181369
13. Sahlen et al. (2015). Genome-wide mapping of promoter-anchored interactions with close to single enhancer resolution. Genome Biology, 16(1). https://doe.org/10.1186/s13059-015-0727-9
14. Stougaard et al. (2011). Strategies for highly sensitive biomarker detection by Rolling Circle Amplification of signals from nucleic acid composed sensors. *Integrative Biology,* 3(10), 982. https://doi.org/10.1039/clib00049g
15. Toh et al. (2013). Immune regulation by CD52-expressing CD4 T cells. *Cellular and Molecular Immunology,* 10(5),379-382. https://doi.org/10.1038/cmi.2013.35
16. Velazquez et al. (2019). Chronic Dyrk1 Inhibition Delays the Onset of AD-Like Pathology in 3×Tg-AD Mice. *Molecular Neurobiology,* 56(12), 8364-8375. https://doi.org/10.1007/s12035-019-01684-9
17. Yaroslavsky et al. (2013). Fluorescence imaging of single-copy DNA sequences within the human genome using PNA-directed padlock probe assembly, Chemistry & Biology, 20(3), 445-453. https://doi.org/10.1016/j.chembiol.2013.02.012

The present invention is not intended to be limited in scope to the particular disclosed embodiments, which are provided, for example, to illustrate various aspects of the invention. Various modifications to the compositions and methods described will become apparent from the description and teachings herein. Such variations may be practiced without departing from the true scope and spirit of the disclosure and are intended to fall within the scope of the present disclosure.

The invention claimed is:

1. A method, comprising:
  (a) contacting a sample with a first chromatin accessing probe and a second chromatin accessing probe simultaneously or sequentially in either order, wherein:
  the sample comprises a first chromatin region and a second chromatin region, wherein the first chromatin region and the second chromatin region are separated by a genomic distance of at least 0.5 kilobases (kb), and wherein the first and second chromatin regions interact with each other in a cell and are in the same chromosome in the cell, and
  the first chromatin accessing probe hybridizes to the complementary strand of a first nucleic acid strand in the first chromatin region and the second chromatin accessing probe hybridizes to the complementary strand of a second nucleic acid strand in the second chromatin region,
  thereby allowing access for binding to the first and second nucleic acid strands;
  (b) contacting the sample with a first detection probe and a second detection probe simultaneously or sequentially in either order, wherein:
  the first detection probe hybridizes to the first nucleic acid strand and the second detection probe hybridizes to the second nucleic acid strand;
  (c) contacting the sample with a first bridging probe that bridges the 3' end of the first detection probe and the 5' end of the second detection probe, and a second bridging probe that bridges the 3' end of the second detection probe and the 5' end of the first detection probe;
  (d) circularizing the first and second bridging probes using the first and second detection probes as templates to form a circular probe, wherein the circular probe comprises a sequence of the first nucleic acid strand and a sequence of the second nucleic acid strand;
  (e) generating a rolling circle amplification (RCA) product of the circular probe in situ in the sample; and
  (f) detecting the RCA product.

2. The method of claim 1, wherein the first and second chromatin accessing probes are peptide nucleic acid (PNA) probes or locked nucleic acid (LNA) probes.

3. The method of claim 2, wherein the melting temperature ($T_m$) of the hybridization between the first or second nucleic acid strand and the corresponding complementary strand is lower than the $T_m$ of the hybridization between the first or second chromatin accessing probe and the corresponding complementary strand.

4. The method of claim 1, wherein the interaction between the first and second chromatin regions in the cell is mediated by one or more chromatin associated factors.

5. The method of claim 1, further comprising treating the sample with a cross-linking agent prior to the contacting step, wherein a nucleic acid in the first and/or second chromatin regions is cross-linked to one another and/or to one or more chromatin associated factors by the cross-linking agent.

6. The method of claim 1, wherein the sample is contacted with the first and/or second chromatin accessing probes at a probe concentration of at least 100 nM, 200 nM, 500 nM, 1 μM, 2 μM, or more than 2 μM.

7. The method of claim 1, wherein the sample is contacted with the first and/or second chromatin accessing probes at a temperature of at least 40° C., 45° C., 50° C., or more than 50° C.

8. The method of claim 1, wherein the sample is incubated with the first and/or second chromatin accessing probes for at least 30 minutes, 1 hours, 2 hours, 5 hours, or more than 5 hours.

9. The method of claim 1, wherein the first chromatin accessing probe comprises one or more barcode sequences corresponding to a nucleic acid sequence of interest in the first chromatin region.

10. The method of claim 1, wherein the second chromatin accessing probe comprises one or more barcode sequences corresponding to a nucleic acid sequence of interest in the second chromatin region.

11. The method of claim 1, wherein the first detection probe comprises one or more barcode sequences corresponding to a nucleic acid sequence of interest in the first chromatin region.

12. The method of claim 1, wherein the second detection probe comprises one or more barcode sequences corresponding to a nucleic acid sequence of interest in the second chromatin region.

13. The method of claim 1, wherein the circular probe comprises one or more barcode sequences corresponding to a nucleic acid sequence of interest in the first chromatin region and/or one or more barcode sequences corresponding to a nucleic acid sequence of interest in the second chromatin region.

14. The method of claim 1, wherein the RCA product is detected in situ in the sample.

15. The method of claim 1, wherein the detecting comprises imaging the sample using fluorescent microscopy.

16. The method of claim 1, wherein the genomic distance between the first and second chromatin regions is at least 5 kb.

17. The method of claim 1, wherein the genomic distance between the first and second chromatin regions is at least 50 kb.

18. The method of claim 1, wherein the first and second chromatin regions comprise a promoter, an enhancer, a silencer, an insulator, and/or a locus control region (LCR).

19. The method of claim 1, wherein the interaction between the first and second chromatin regions in the cell is mediated by a transcription factor, an activator, a repressor, a chromatin-remodeler, a polymerase, a replication factor, a DNA repair factor, a histone, a histone-modifying enzyme, and/or a DNA-modifying enzyme.

20. The method of claim 1, wherein the genomic distance between the first and second chromatin regions is at least 1 kb.

* * * * *